(12) United States Patent
De Brabander et al.

(10) Patent No.: US 7,838,691 B2
(45) Date of Patent: Nov. 23, 2010

(54) PALMEROLIDES: METHODS OF PREPARATION AND DERIVATIVES THEREOF

(75) Inventors: Jef K. De Brabander, Lewisville, TX (US); Xin Jiang, Dallas, TX (US); Bo Liu, Sichuan (CN)

(73) Assignee: Board of Regents, of the University of Texas System, Austin, TX (US)

( * ) Notice: Subject to any disclaimer, the term of this patent is extended or adjusted under 35 U.S.C. 154(b) by 147 days.

(21) Appl. No.: 12/098,001

(22) Filed: Apr. 4, 2008

(65) Prior Publication Data

US 2008/0249162 A1 Oct. 9, 2008

Related U.S. Application Data

(60) Provisional application No. 60/910,358, filed on Apr. 5, 2007.

(51) Int. Cl.
C07D 313/00 (2006.01)
(52) U.S. Cl. .................................................. 549/346
(58) Field of Classification Search ................. 549/346
See application file for complete search history.

(56) References Cited

U.S. PATENT DOCUMENTS

| 5,552,548 | A | 9/1996 | Quallich | |
|---|---|---|---|---|
| 7,625,885 | B2 * | 12/2009 | Baker et al. .................. | 514/175 |
| 2005/0009765 | A1 | 1/2005 | Yu et al. | |
| 2005/0187286 | A1 | 8/2005 | Baker et al. | |

FOREIGN PATENT DOCUMENTS

WO    WO 97/41097 A2    9/1996
WO    WO 2007/035734 A2    3/2007

OTHER PUBLICATIONS

Diyabalanage et al. J. Am. Chem. Soc., 2006, 128, 5630-5631.*
Urbina et al. Biol Res 39: 289-296, 2006.*
Wolff, Burger's Medicinal Chemistry and Drug Discovery, vol. 1, Principles and Practice, John Wiley & Sons, New York. 1997.*
Chin et al. Drug Discovery From Natural Sources, The AAPS Journal 2006, 8(2), Article 28.*
Cragg et al. Natural products in Drug Discovery and Development, J. Natural Products, 1997, 60, 52-60.*
Burger's Medical Chemistry and Drug Chemistry 5$^{th}$ ed. pp. 172-178 & 949-982, (1995).
Thushara Diyabalanage et al., "Palmerolide A, a Cytotoxic Macrolide from the Antarctic Tunicate Synoicum adareanum", J. Am. Chem. Soc. 2006, 128, 5630-5631.
Thomas Voets et al., "TRPM6 Forms the Mg2+ Influx Channel Involved in Intestinal and Renal Mg2+ Adsorption", The Journal of Biological Chemistry vol. 279, No. 1, Issue of Jan. 2, 2004, pp. 19-25.
W. Clark Still et al., "Rapid Chromatographic Technique for Preparative Separations with Moderate Resolution", J. Org. Chem. vol. 43, No. 14, 1978, 2923-2925.
Shin-ichi Shirokawa et al., "Remote Asymmetric Induction with Vinylketene Silyl N, O-Acetal", J. Am. Chem. Soc. 2004, 126, 13604-13605.
James A. Marshall et al., "Diastereoselective Additions of Chiral Vinylzinc Reagents to α-Chiral Aldehydes", Organic Letters, 2004, vol. 6, No. 3, pp. 445-448.
Merek Urbansky et al., "Synthesis of Enantiopure 2-C-Methy-D-erythritol 4-Phosphate and 2,4-Cyclodiphosphate from D-Arabitol", Organic Letters, vol. 6, No. 1, 2004, 135-138.
Peter G.M. Wuts et al., "Preparation of Halomethaneboronates", Journal of Organometallic Chemistry, 234 (1982) 137-141.
Marinella Govoni et al., "A Chemical Switch for the Modulation of the functional Activity of Higher Homologues of Histamine on the Human Histamine H3 Receptor: Effect of Various Substitutions at the Primary Amino function", J. Med. Chem. 2006, 49, 2549-2557.

* cited by examiner

*Primary Examiner*—D. Margaret Seaman
*Assistant Examiner*—Nizal S Chandrakumar
(74) *Attorney, Agent, or Firm*—Stephen A. Bent; Foley & Lardner LLP

(57) ABSTRACT

Organic compounds having Formulas I and II are provided where the variables have the values described herein.

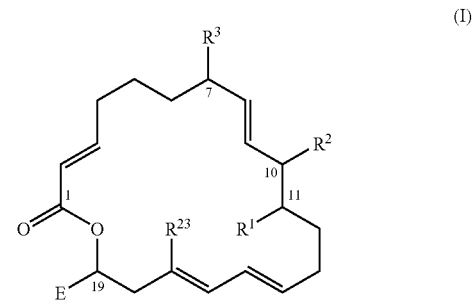

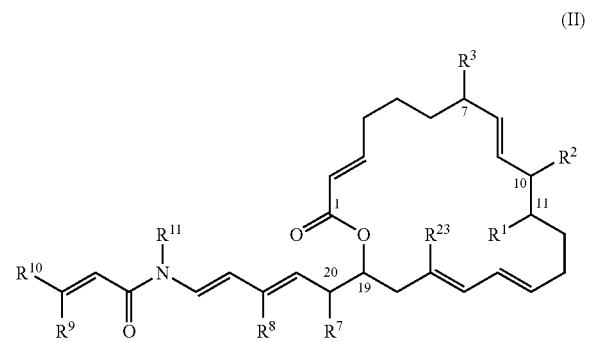

Pharmaceutical formulations include the organic compounds or pharmaceutically acceptable salts thereof and a pharmaceutically acceptable carrier can be prepared. Methods of preparing the compounds includes deprotecting protected precursor compounds. Methods of treating cancer or inhibiting ATPase include administering the organic compounds to a subject in need thereof.

2 Claims, 7 Drawing Sheets

PALMEROLIDES: METHODS OF PREPARATION AND DERIVATIVES THEREOF

CROSS-REFERENCE TO RELATED APPLICATION

This application claims priority to U.S. Provisional Application No. 60/910,358, filed on Apr. 5, 2007, the entire contents of which are incorporated herein by reference for any and all purposes.

GOVERNMENT RIGHTS

The United States Government has rights in this invention pursuant to Contract Number CA90349 between the National Institutes of Health and the University of Texas Southwest.

FIELD OF THE INVENTION

The present invention is generally related to compounds for the treatment of cancer, their preparation, and derivatives thereof. In some embodiments, the compounds are generally related to a class of compounds called palmerolides, their preparation, isomers thereof, and derivatives thereof.

BACKGROUND OF THE INVENTION

An Antarctic marine tunicate, *Synoicum adareanum*, is the source of a material, called "palmerolide A," which was characterized as a differential cytotoxin, with an activity profile that correlated to V-ATPase inhibitors. *J. Am. Chem. Soc.* 2006, 128, 5630. Subsequent in vitro studies confirmed that palmerolide A indeed is a potent inhibitor of ATPases, in particular, bovine brain V-ATPase ($IC_{50}$~2 nM), and is a selective cytotoxin toward several cancer cell lines including melanoma, colon cancer, and renal cancer. Id.; U.S. Published Application No. 2005-0187286, the only portions of which are incorporated by reference, are those describing the inhibitory effects of Palmerolide A; and *J. Biol. Chem.* 2004, 279, 19755.

Palmerolide A was obtained from an organism found in one of the most remote areas of the world. Access from natural sources is severely limited by this fact and by the effective prohibition, via international treaty, of commercial exploitation in the Antarctic. A total synthesis is needed, therefore, to realize the promising antitumor properties of palmerolides.

SUMMARY OF THE INVENTION

In one aspect, a compound is provided selected from a compound of Formula I, a tautomer thereof, or a pharmaceutically acceptable salt of either:

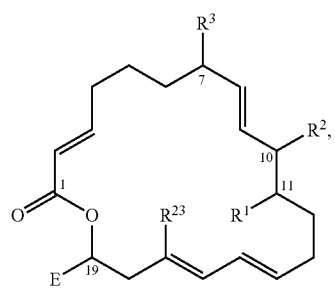

(I)

wherein E is selected from substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkylalkenyl, substituted or unsubstituted cycloalkylalkynyl, substituted or unsubstituted aralkyl, substituted or unsubstituted aralkenyl, substituted or unsubstituted aralkynyl, substituted or unsubstituted heteroaralkyl, substituted or unsubstituted heteroaralkenyl, substituted or unsubstituted heteroaralkynyl, substituted or unsubstituted heterocyclylalkyl, substituted or unsubstituted heterocyclylalkenyl, substituted or unsubstituted heterocyclylalkynyl, substituted or unsubstituted eneamines, or substituted or unsubstituted dienamines; $R^1$ is selected from $OC(O)NR^{12}R^{13}$ or $OR^{18}$; $R^2$ is $OR^{14}$; $R^3$ is selected from $OR^{14}$ or =O; $R^{12}$, and $R^{13}$ are at each occurrence independently selected from H, OH, substituted or unsubstituted $C_{1-8}$ alkyl, substituted or unsubstituted aryl, substituted or unsubstituted aralkyl, substituted or unsubstituted heterocyclyl, substituted or unsubstituted heterocyclylalkyl, substituted or unsubstituted cycloalkyl, or substituted or unsubstituted cycloalkylalkyl; $R^{14}$ at each occurrence is independently selected from H, substituted or unsubstituted $C_{1-8}$ alkyl, or a protecting group; $R^{18}$ at each occurrence is selected from H or a protecting group; and $R^{23}$ is selected from H, F, $CH_3$, or $CF_3$.

In one embodiment, E is selected from

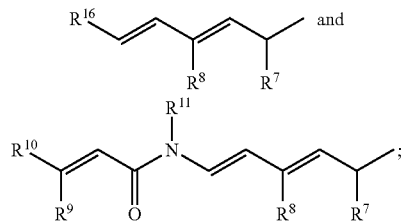

$R^7$ and $R^8$ are independently selected from H, F, or substituted or unsubstituted $C_{1-3}$ alkyl; $R^9$ and $R^{10}$ are independently selected from H, CN, F, $OR^{14}$, substituted or unsubstituted $C_{1-8}$ alkyl, substituted or unsubstituted cycloalkyl, substituted or unsubstituted or cycloalkylalkyl, substituted or unsubstituted aryl, substituted or unsubstituted aralkyl, substituted or unsubstituted heterocyclyl, or substituted or unsubstituted heterocyclylalkyl; $R^{11}$ is selected from H or substituted or unsubstituted $C_{1-3}$ alkyl; $R^{16}$ is selected from carboxylate, carboxylic ester, $NR^{11}R^{17}$, or $NR^{11}C(O)R^{17}$; $R^{17}$ is selected from H, OH, $OR^{14}$, substituted or unsubstituted $C_{1-8}$ alkyl, substituted or unsubstituted $C_{1-8}$ alkenyl, substituted or unsubstituted $C_{1-8}$ alkynyl, substituted or unsubstituted aryl, substituted or unsubstituted aralkyl, substituted or unsubstituted heterocyclyl, substituted or unsubstituted heterocyclylalkyl, substituted or unsubstituted cycloalkyl, or substituted or unsubstituted cycloalkylalkyl.

In one embodiment, E is

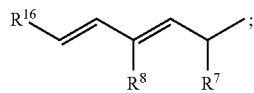

wherein $R^7$ and $R^8$ are independently selected from H or substituted or unsubstituted $C_{1-3}$ alkyl; $R^{17}$ is selected from H, $OR^4$, $-C\equiv CR^{22}$, $-CR^{24}=CR^{21}R^{26}$; and $R^{22}$, $R^{24}$, $R^2$, and $R^{26}$ are independently selected from H, substituted or unsubstituted $C_{1-8}$ alkyl, substituted or unsubstituted $C_{1-8}$ alkenyl, substituted or unsubstituted $C_{1-8}$ alkynyl, substituted or unsubstituted cycloalkyl, substituted or unsubstituted aryl, substituted or unsubstituted aralkyl, substituted or unsubstituted heteroaryl, substituted or unsubstituted heteroaralkyl, substituted or unsubstituted heterocyclyl, or substituted or unsubstituted heterocyclylalkyl. In some embodiments, $R^7$ and $R^8$ are independently selected from the group consisting H or methyl; $R^{16}$ is selected from carboxylate, carboxylic ester, or $NR^{11}C(O)R^{17}$; $R^{11}$ is H; $R^{17}$ is selected from —C≡$CR^{22}$ or $CR^{24}$=$CR^{25}R^{26}$; and $R^{22}R^{24}$, $R^{25}$, and $R^{26}$ are independently selected from H, methyl, ethyl, propyl, iso-propyl, butyl, sec-butyl, tert-butyl, substituted phenyl, or substituted benzyl.

In another embodiment E is

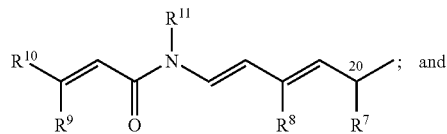
; and $R^2$ and $R^3$ are independently $OR^{14}$; $R^7$, $R^8$, $R^9$, and $R^{10}$ are independently selected from H or substituted or unsubstituted $C_{1-3}$ alkyl; $R^{12}$ and $R^{13}$ are independently selected from H or substituted or unsubstituted $C_{1-3}$ alkyl; $R^{14}$ at each occurrence is independently selected from H or a protecting group; and $R^{23}$ is methyl.

In another embodiment, the compound of Formula I has stereochemical configurations at carbon atoms numbered 7, 10, 11, 19, and 20 selected from RRRRR, RRRRS, RRRSR, RRSRR, RSRRR, SRRRR, RRRSS, RRSRS, RRSSR, RSRRS, RSRSR, RSSRR, SRRRS, SRRSR, SRSRR, SSRRR, RRSSS, RSRSS, RSSRS, RSSSR, SRRSS, SRSRS, SRSSR, SSRRS, SSRSR, SSSRR, RSSSS, SRSSS, SSRSS, SSSRS, SSSSR, or SSSSS. For example, RSRSR is R at C-7, S at C-10, R at C-11, S at C-19, and R at C-20.

In some embodiments, the compound of Formula I is selected from a compound of Formula II, a tautomer thereof, or a pharmaceutically acceptable salt of either:

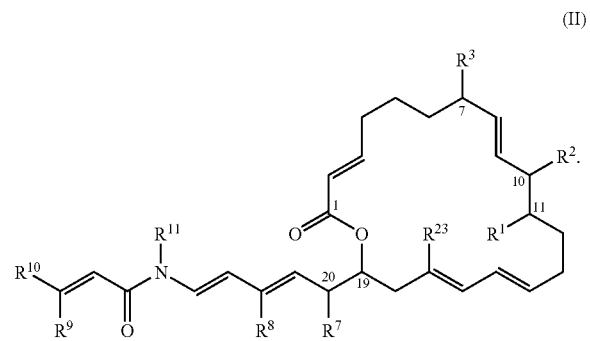
(II)

In other embodiments, the compound of Formula II is a compound of Formula IIA:

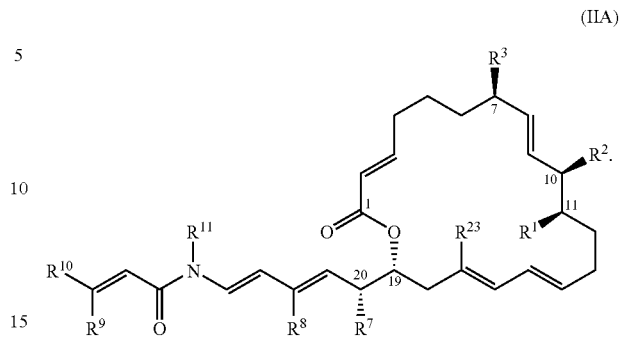
(IIA)

In other embodiments, the compound of Formula II is a compound of Formula IIB:

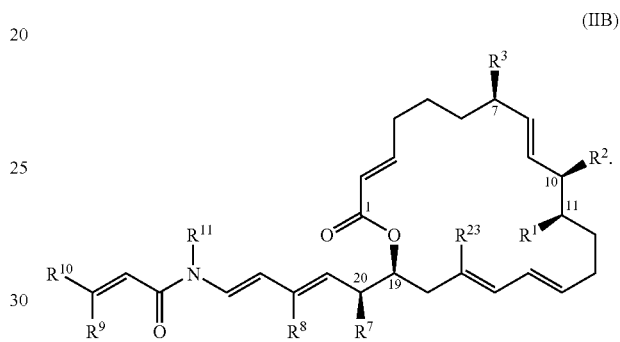
(IIB)

In other embodiments, the compound of Formula II is a compound of Formula ent-IIB:

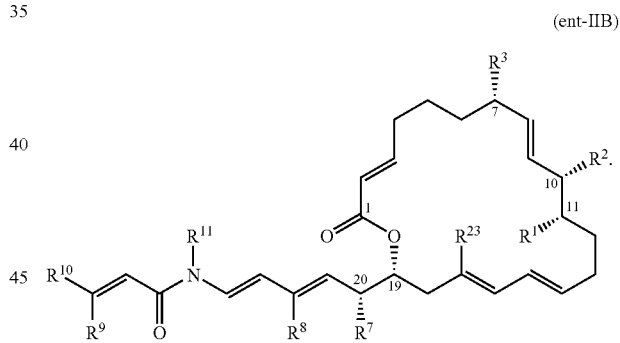
(ent-IIB)

In still other embodiments, the compound of Formula I is selected from a compound of Formula III, a tautomer thereof, or a pharmaceutically acceptable salt of either:

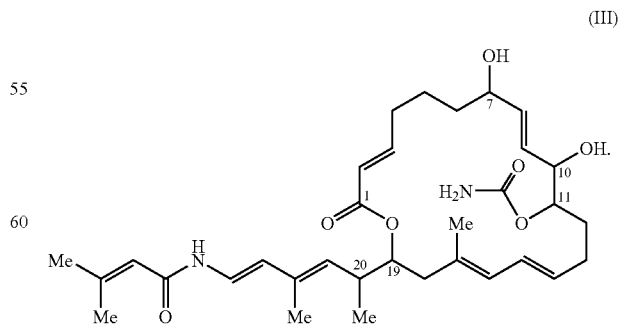
(III)

In other embodiments, the compound of Formula III has stereochemical configurations of carbon atoms numbered 7, 10, 11, 19, and 20 selected from RRRRR, RRRRS, RRRSR, RRSRR, RSRRR, SRRRR, RRRSS, RRSRS, RRSSR, RSRRS, RSRSR, RSSRR, SRRRS, SRRSR, SRSRR, SSRRR, RRSSS, RSRSS, RSSRS, RSSSR, SRRSS, SRSRS, SRSSR, SSRRS, SSRSR, SSSRR, RSSSS, SRSSS, SSRSS, SSSRS, SSSSR, or SSSSS.

In other embodiments, the compound of Formula III is selected from a compound of Formula IIIB, a tautomer thereof, or a pharmaceutically acceptable salt of either:

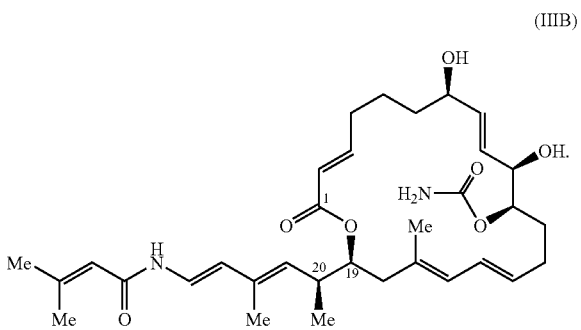

(IIIB)

In other embodiments, the compound of Formula III is selected from a compound of Formula ent-IIIB, a tautomer thereof, or a pharmaceutically acceptable salt of either:

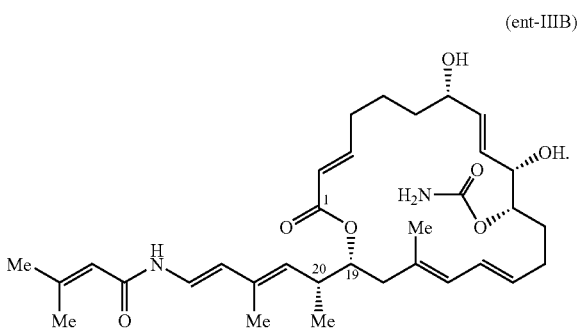

(ent-IIIB)

In another aspect, a pharmaceutical composition is provided having (i) a therapeutically effective amount of the compound of Formula I, a tautomer of the compound of Formula I, a pharmaceutically acceptable salt of the compound of Formula I, a pharmaceutically acceptable salt of the tautomer of the compound of Formula I, a prodrug of the compound of Formula I, or a mixture of any two or more thereof, and (ii) a pharmaceutically acceptable carrier.

In some embodiments, the pharmaceutically acceptable carrier is a diluent, an excipient, a wetting agent, a buffering agent, a suspending agent, a lubricating agent, an adjuvant, a vehicle, a delivery system, an emulsifier, a disintegrant, an absorbent, a preservative, a surfactant, a colorant, a flavorant, a sweetener, or a mixture of any two or more thereof.

In another aspect, a process for preparing the compound of Formula II is provided, comprising deprotecting the compound of Formula IV:

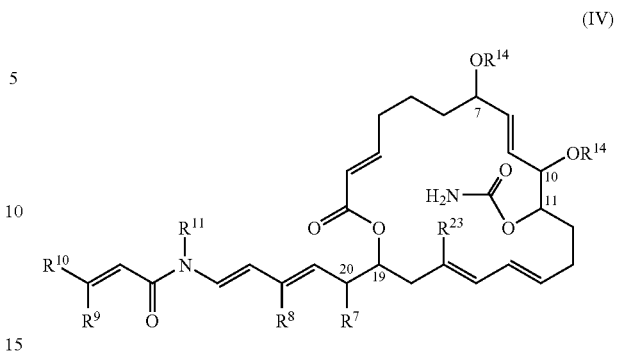

(IV)

wherein at least one of the $R^{14}$ groups is a protecting group. In some such embodiments, the protecting group is trimethylsilyl, triethylsilyl, tripropylsilyl, triisopropylsilyl, tributylsilyl, tert-butyldimethylsilyl, or tert-butyldiphenylsilyl. In other such embodiments, the deprotecting step comprises reacting the compound of Formula III with a source of fluoride ion. In some such embodiments, the source of fluoride ion is a tetraalkylammonium fluoride such as, but not limited to, tetramethylammonium fluoride, tetraethyl ammonium fluoride, tetrapropylammonium fluoride, or tetrabutylammonium fluoride; cesium fluoride; HF; or a mixture of any two or more thereof.

In other embodiments, the stereochemical configuration of the compound of Formula IV at the carbon atoms numbered 7, 10, 11, 19, and 20 is selected from RRRRR, RRRRS, RRRSR, RRSRR, RSRRR, SRRRR, RRRSS, RRSRS, RRSSR, RSRRS, RSRSR, RSSRR, SRRRS, SRRSR, SRSRR, SSRRR, RRSSS, RSRSS, RSSRS, RSSSR, SRRSS, SRSRS, SRSSR, SSRRS, SSRSR, SSSRR, RSSSS, SRSSS, SSRSS, SSSRS, SSSSR, or SSSSS.

In other embodiments, process further comprises preparing the compound of Formula IV comprising reacting a compound of Formula V with $X_3C(O)NCO$

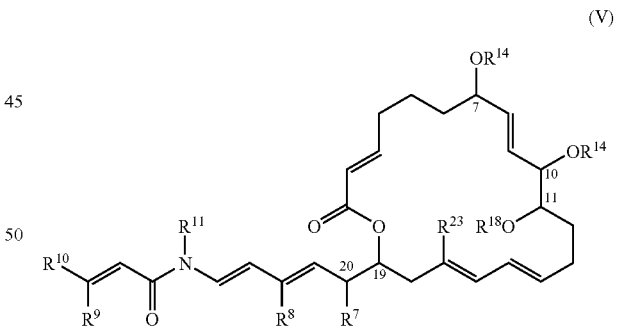

(V)

wherein X is halogen. In some such embodiments, $R^{18}$ is H, trimethylsilyl, triethylsilyl, tripropylsilyl, triisopropylsilyl, tributylsilyl, tert-butyldimethylsilyl, or tert-butyldiphenylsilyl.

In some embodiments, the stereochemical configuration of the compound of Formula V at the carbon atoms numbered 7, 10, 11, 19, and 20 is selected from RRRRR, RRRRS, RRRSR, RRSRR, RSRRR, SRRRR, RRRSS, RRSRS, RRSSR, RSRRS, RSRSR, RSSRR, SRRRS, SRRSR, SRSRR, SSRRR, RRSSS, RSRSS, RSSRS, RSSSR, SRRSS, SRSRS, SRSSR, SSRRS, SSRSR, SSSRR, RSSSS, SRSSS, SSRSS, SSSRS, SSSSR, or SSSSS.

In some embodiments, the compound of Formula I is selected from a compound of Formula VI, a tautomer thereof, or a pharmaceutically acceptable salt of either:

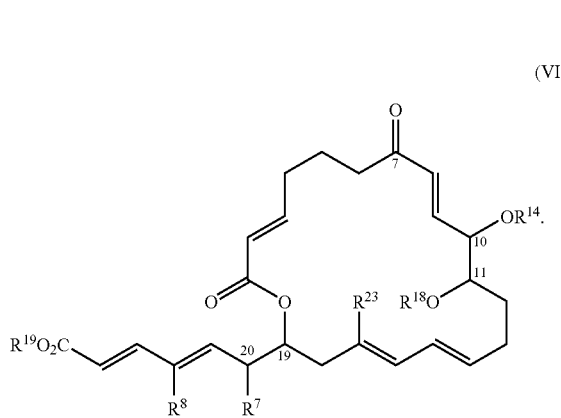

(VI)

wherein $R^{19}$ is H or a substituted or unsubstituted $C_{1-4}$ alkyl. In some such embodiments, $R^{14}$ and $R^{18}$ are independently H, trimethylsilyl, triethylsilyl, tripropylsilyl, triisopropylsilyl, tributylsilyl, tert-butyldimethylsilyl, or tert-butyldiphenylsilyl; and $R^{19}$ is methyl or ethyl. In some embodiments, the stereochemical configuration of the compound of Formula VI at the carbon atoms numbered 10, 11, 19, and 20 is selected from RRRR, RRRS, RRSR, RSRR, SRRR, RRSS, RSRS, RSSR, SRRS, SRSR, SSRR, RSSS, SRSS, SSRS, SSSR, or SSSS.

In some embodiments of the above process, the process further comprises preparing a compound of Formula VIIC or VIID, comprising reducing a compound of Formula VI with a stereospecific reducing agent,

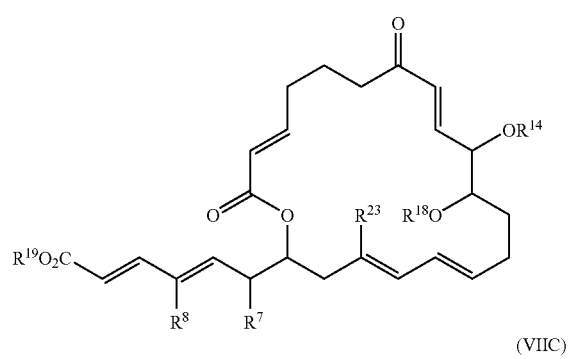

(VI)

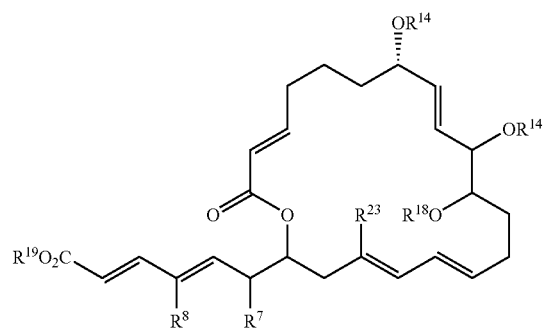

(VIIC)

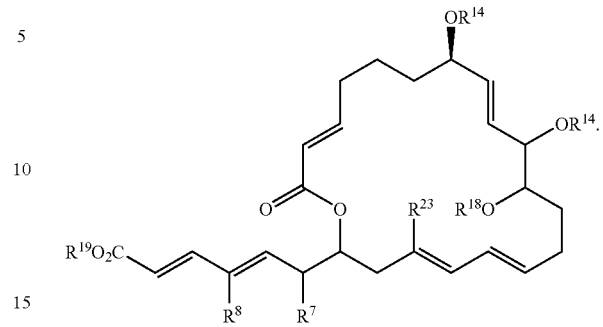

(VIID)

In some embodiments, the stereospecific reducing agent is (S)-2-methyl-CBS-oxazaborolidine or (R)-2-methyl-CBS-oxazaborolidine.

In another aspect, a compound of Formula VIII, a tautomer thereof, or a pharmaceutically acceptable salt of either is provided:

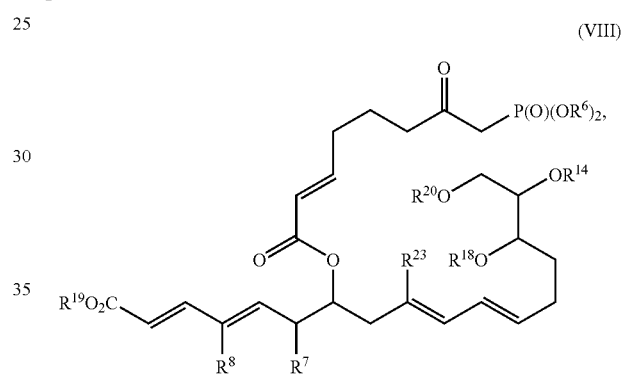

(VIII)

wherein $R^7$ and $R^8$ are independently H, F, substituted or unsubstituted $C_{1-3}$ alkyl; $R^6$ and $R^{19}$ are independently H or a substituted or unsubstituted $C_{1-4}$ alkyl; and $R^{14}$, $R^{18}$, and $R^{20}$ are independently H or a protecting group. In one embodiment, $R^{14}$, $R^{18}$, and $R^{20}$ are each independently H, trimethylsilyl, triethylsilyl, tripropylsilyl, triisopropylsilyl, tributylsilyl, tert-butyldimethylsilyl, or tert-butyldiphenylsilyl; $R^{19}$ is methyl or ethyl; and $R^6$ is methyl or ethyl.

In one embodiment, the process comprises preparing the compound of Formula VI, comprising cyclizing a compound of Formula VIII:

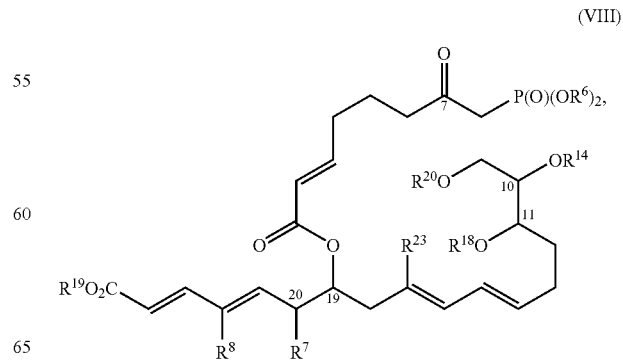

(VIII)

wherein $R^7$ and $R^8$ are independently H, F, substituted or unsubstituted $C_{1-3}$ alkyl; $R^6$ and $R^{19}$ are independently H or a substituted or unsubstituted $C_{1-4}$ alkyl; and $R^{14}$, $R^{18}$, and $R^{20}$ are independently H or a protecting group. In another embodiment, $R^{20}$ is H and the cyclizing step comprises a selective oxidation, followed by addition of a base. In yet other embodiments, the cyclizing step comprises a Horner-Wadsworth-Emmons-mediated cyclization. In other embodiments, the stereochemical configuration of the compound of Formula VI at the carbon atoms numbered 10, 11, 19, and 20 is selected from RRRR, RRRS, RRSR, RSRR, SRRR, RRSS, RSRS, RSSR, SRRS, SRSR, SSRR, RSSS, SRSS, SSRS, SSSR, or SSSS.

In other embodiments, the process comprises coupling a compound of Formula IX and a compound of Formula X:

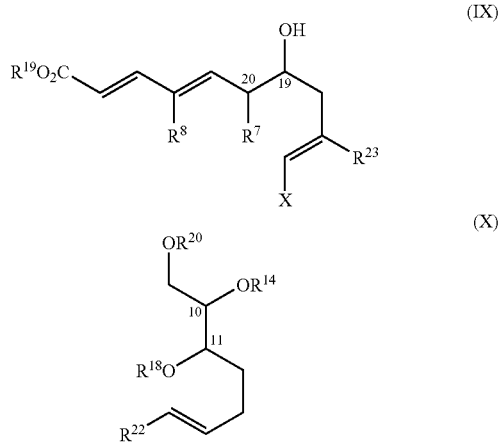

wherein X is F, Cl, Br, or I, and $R^{22}$ is a boron-based group or a trialkyltin group. In some embodiments, $R^{14}$, $R^{18}$, and $R^{20}$ are each independently H, trimethylsilyl, triethylsilyl, tripropylsilyl, triisopropylsilyl, tributylsilyl, tert-butyldimethylsilyl, or tert-butyldiphenylsilyl; $R^{19}$ is methyl or ethyl. In other embodiments, $R^{22}$ is pinacolboronate, catecholboronate, 9-borabicyclononyl, dicyclohexylborane, or trialkyltin. In yet other embodiments, the coupling step is a Suzuki coupling or a Stille coupling. In yet other embodiments, the stereochemical configuration of the compound of Formula IX at the carbon atoms numbered 19 and 20 is selected from RR, RS, SR, or SS. In yet other embodiments, the stereochemical configuration of the compound of Formula X at the carbon atoms numbered 10 and 11 is selected from RR, RS, SR, or SS.

In another aspect, a method for treating a subject suffering from cancer is provided, comprising administering the compound of claim 1 to the subject.

In another aspect, a method of inhibiting ATPase is provided, comprising administering the compound of claim 1 to a subject in need of an ATPase inhibitor. In some embodiments, the ATPase is V-ATPase.

Conditions: (a) $Ph_3PCHCO_2Me$, PhMe, reflux (99%); (b) TIPSOTf, 2,6-lutidine, $CH_2Cl_2$, 0° C.; (c) Pd/C, H$_2$, EtOH, rt (95%, 2 steps); (d) TESCl, imidazole, DMF, rt (93%); (e) DIBAL, $CH_2Cl_2$, −78° C. (93%); (f) $CrCl_2$, LiI, THF, rt (84%).

Figure 4:
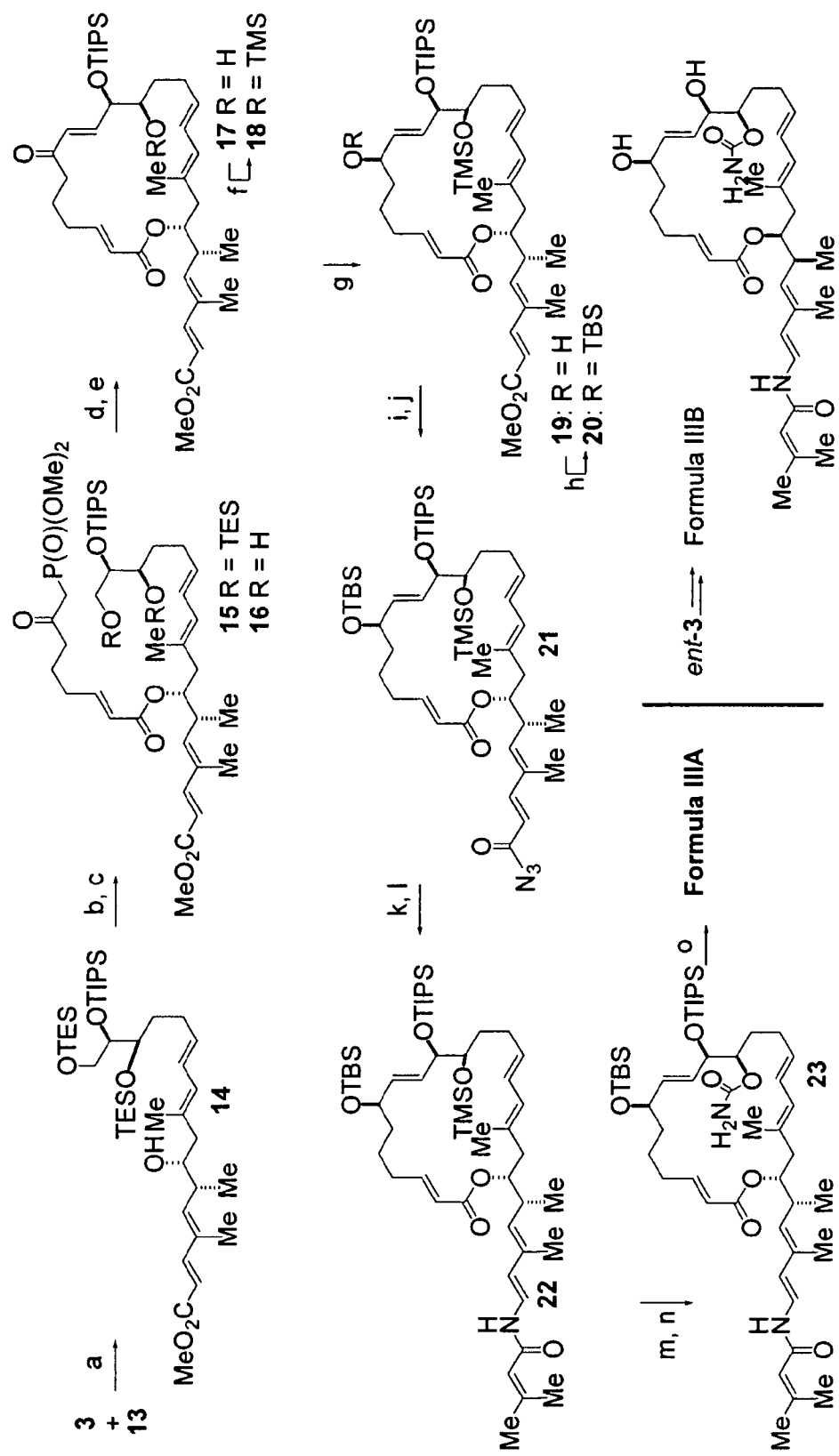

FIG. 4 is a scheme outlining steps in the preparation of a compound of Formula IIIA and IIIB, according to various embodiments. FIG. 4 conditions: (a) cat. $Pd(Ph_3)_4$, $Tl2CO_3$, THF/$H_2O$, rt (76%); (b) 2,2,4,6-$Cl_3$BzCl, $NEt_3$, DMAP, PhMe, rt (69%), (c) PPTS, MeOH, 0° C. (95%), (d) PhI(OAc)$_2$, TEMPO, $CH_2Cl_2H_2O$, rt; (e) $K_2CO_3$, 18-crown-6, PhMe, 60° C. (70%, 2 steps) (f) TMSCl, $Et_3N$, cat. DMAP, $CH_2Cl_2$, rt (91%); (g) (S)—CBS BH$_3$ THF, −40° C. (95%); (h) TBSOTf, 2,6-lutidine, $CH_2Cl_2$, −78° C. (94%); (i) $(Bu_3Sn)_2O$, PhMe, 80° C. (81%); (j) $(PhO)_2P(O)N_3$, $NEt_3$, benzene, rt (92%); (k) benzene, reflux; (l) 2-Me-1-propenylmagnesium bromide, −78° C. (76%, 2 steps); (m) HF.py, py, THF, rt (95%); (n) $Cl_3C(O)NCO$, $CH_2Cl_2$, 0° C.; $Al_2O_3$, rt (95%); (o) TBAF, THF, 0° C. (40%).

Figure 5:
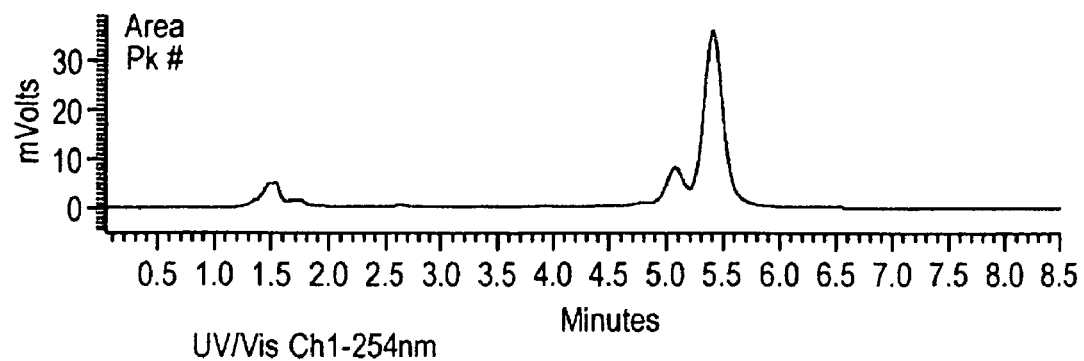

FIG. 5 is the HPLC chromatogram (with UV-VIS detection) of Synthetic Palmerolide A on a Phenomenex® LUNA SILICA 250×4.6 mm (5μ) column at a flow rate of 2 mL/min using 10% MeOH in $CH_2Cl_2$ as the mobile phase.

Figure 6:
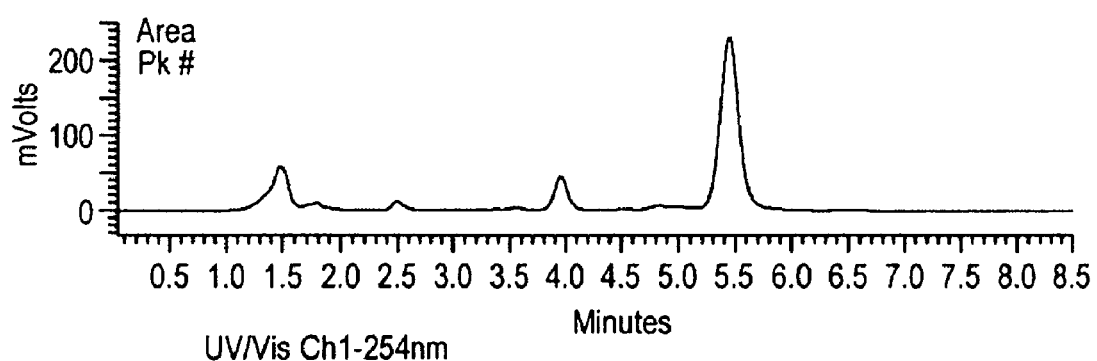

FIG. 6 is the HPLC chromatogram (with UV-VIS detection) of Synthetic Palmerolide A on a Phenomenex® LUNA SILICA 250×4.6 mm (5μ) column at a flow rate of 2 mL/min using on: 10% MeOH in $CH_2Cl_2$ as the mobile phase.

Figure 7:
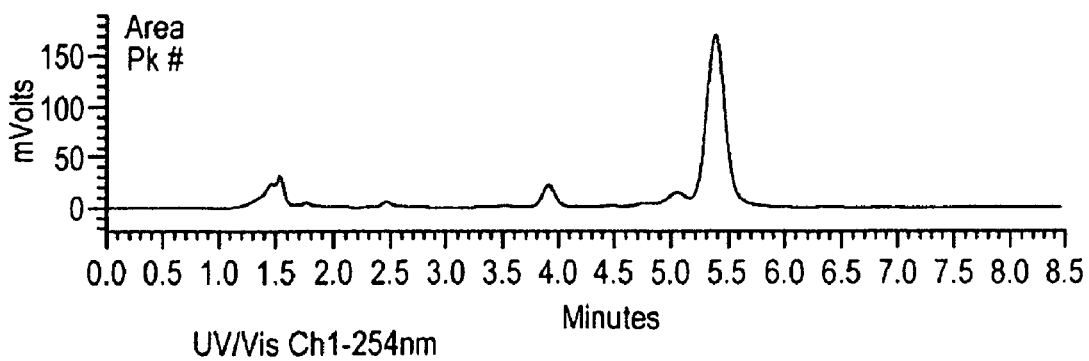

FIG. 7 is the HPLC chromatogram (with UV-VIS detection) of Synthetic Palmerolide A on a Phenomenex® LUNA SILICA 250×4.6 mm (5μ) column at a flow rate of 2 mL/min using on: 10% MeOH in $CH_2Cl_2$ as the mobile phase.

Figure 8:
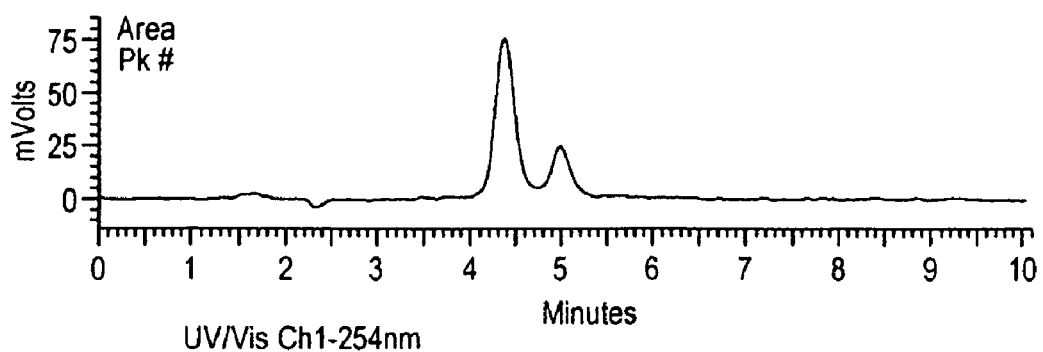

FIG. 8 is the HPLC chromatogram (with UV-VIS detection) of Synthetic Palmerolide A on a Phenomenex® LUNA SILICA 250×4.6 mm (5μ) column at a flow rate of 2 mL/min using on: 2.5% MeOH in EtOAc as the mobile phase.

Figure 9:
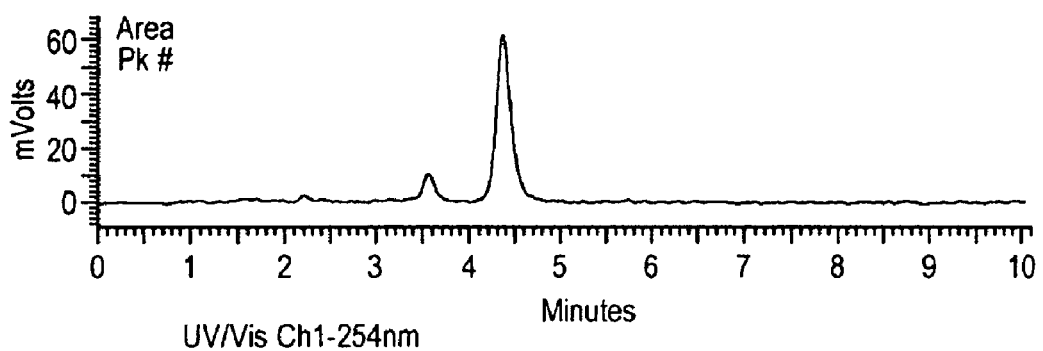

FIG. 9 is the HPLC chromatogram (with UV-VIS detection) of Synthetic Palmerolide A on a Phenomenex® LUNA SILICA 250×4.6 mm (5μ) column at a flow rate of 2 mL/min using on: 2.5% MeOH in EtOAc as the mobile phase.

Figure 10:
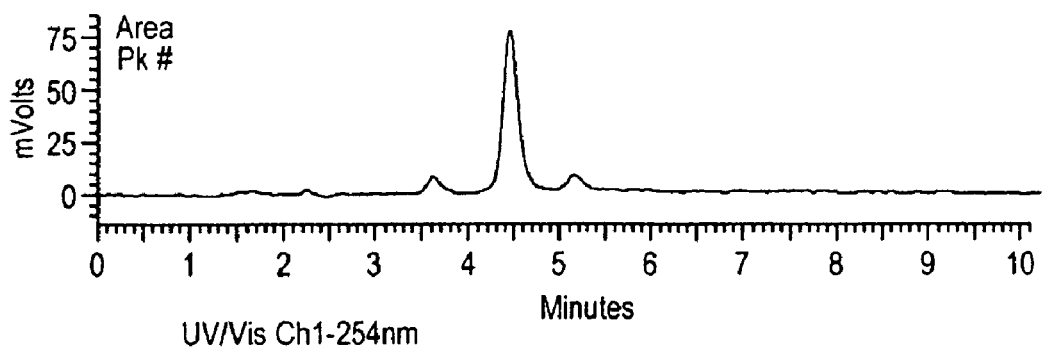

FIG. 10 is the HPLC chromatogram (with UV-VIS detection) of Synthetic Palmerolide A on a Phenomenex® LUNA SILICA 250×4.6 mm (5μ) column at a flow rate of 2 mL/min using on: 2.5% MeOH in EtOAc as the mobile phase.

Figure 11:
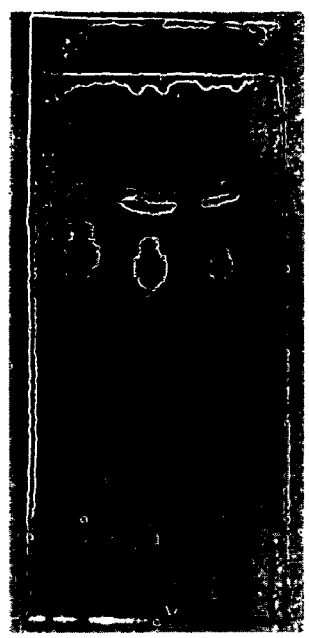

FIG. 11 is a photograph of a TLC (Thin Layer Chromatography) Plate eluted with $CH_2Cl_2$/MeOH (5:1) and showing as the left spot: natural Palmerolide A; as the middle spot: co-spot of natural and synthetic Palmerolide A; and as the right spot: synthetic Palmerolide A.

Figure 12:
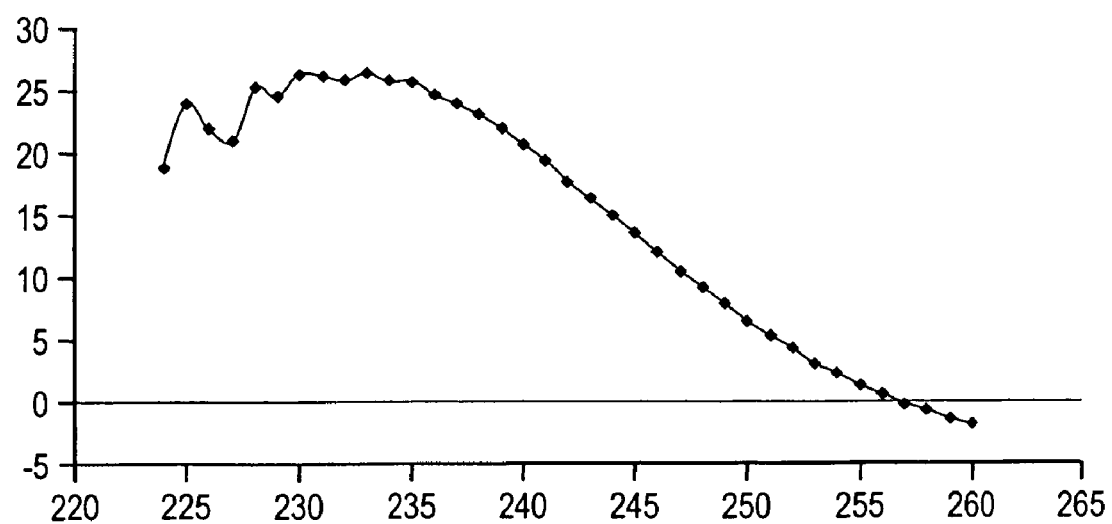

FIG. 12 is a Circular Dichroism (CD) Spectrum of synthetic palmerolide A, c=0.0017 M in CHCl$_3$; cell length=1 mm.

Figure 13:
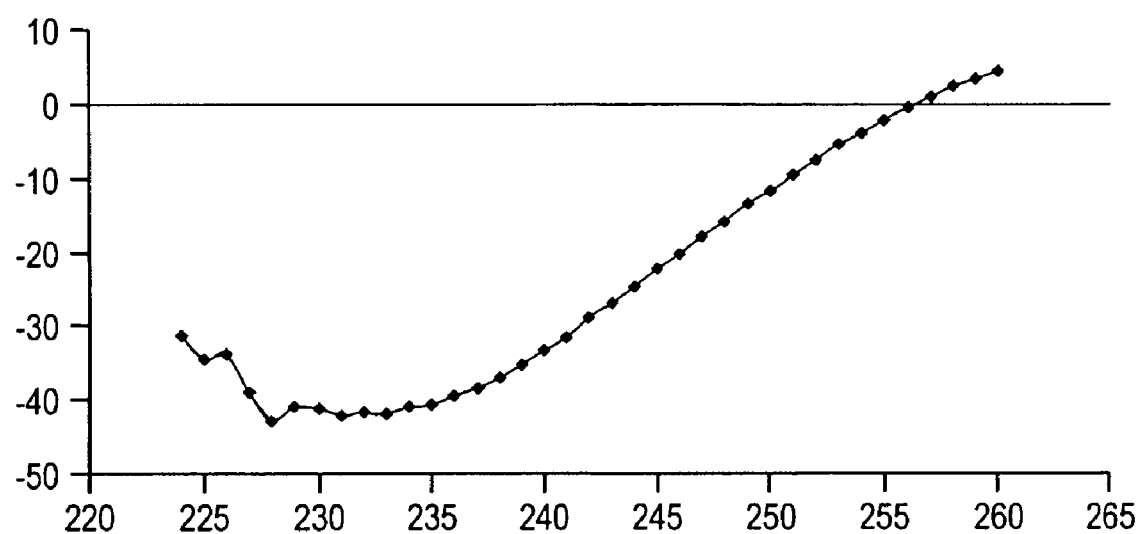

FIG. 13 is a CD Spectrum of natural palmerolide A, c=0.0025 M in CHCl$_3$; cell length=1 mm.

DETAILED DESCRIPTION OF THE INVENTION

Given the lack of Palmerolide A in natural abundance, synthetic efforts have been undertaken to prepare this material, related palmerolides, palmerolide derivatives, and other compounds containing the macrocyclic portion of the palmerolides. These synthetic efforts resulted in the total synthesis of a number of palmerolide compounds including those of Formula IIIA and ent-IIIB. Spectral investigations including nuclear magnetic resonance and circular dichroism identified Palmerolide A as that of the compound of Formula ent-IIIB.

The structures of Formula IIIA and ent-IIIB are:

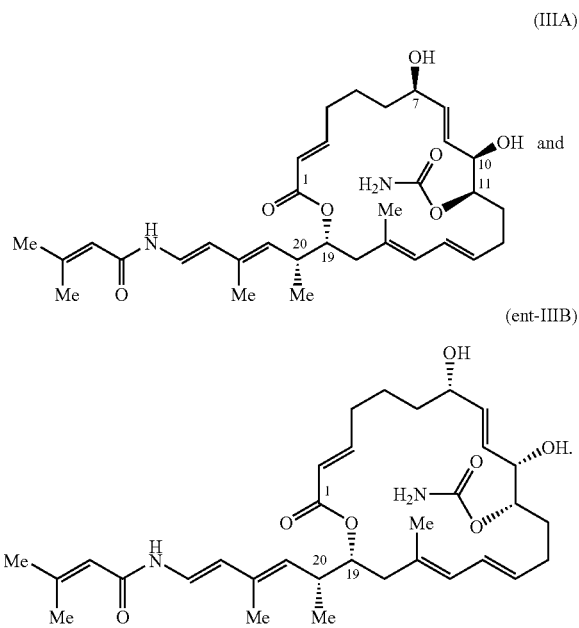

The synthetic procedures embodied herein may be used to prepare a large variety of palmerolides, palmerolide derivatives, and other compounds having similar macrocyclic structures. A synthetic procedure, according to one embodiment, is described below.

An Exemplary Synthetic Procedure

Figure 1:
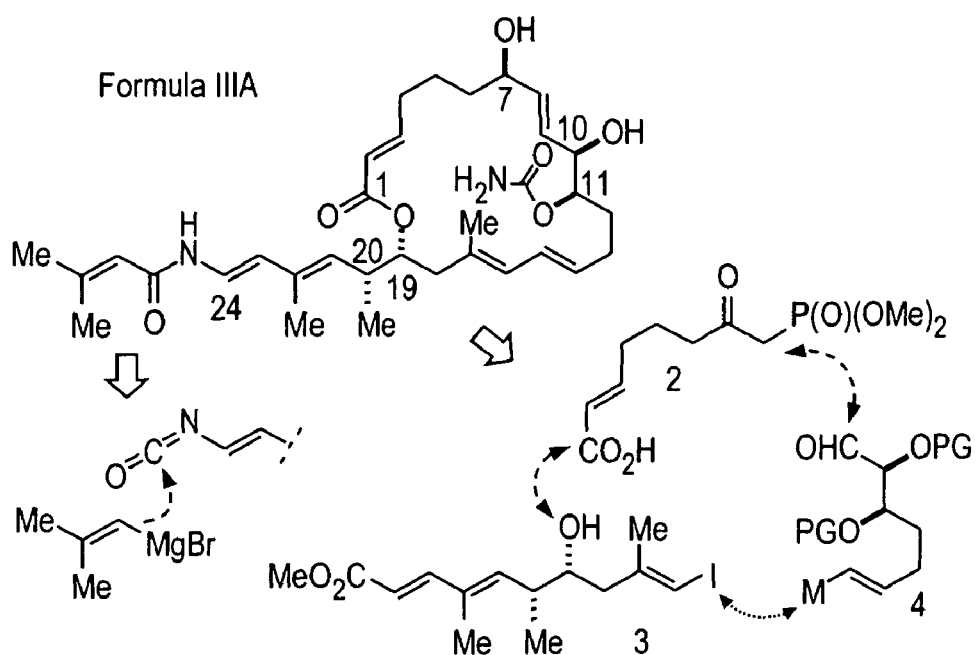
FIG. 1 is a scheme outlining the preparation of a compound of Formula IIIA, according to one embodiment.

In accordance with one embodiment, FIGS. 1-4 set out an overall synthetic route to Palmerolide A (ent-IIIB), the enantiomer of the C19,20-bis-epimer of Formula IIIA. Palmerolides can be prepared from fragments such as 2-4 via cross-coupling of 3 and 4, followed by an esterification with enoic acid 2, a fragment with a keto-phosphonate positioned to induce macrocyclization via Horner-Wadsworth-Emmons olefination (FIG. 1). A Curtius rearrangement followed by isocyanate-trapping with 2-Me-propenylmagnesium bromide can be used to install the sensitive N-acyl dienamine functionality at the final stages.

Figure 2:
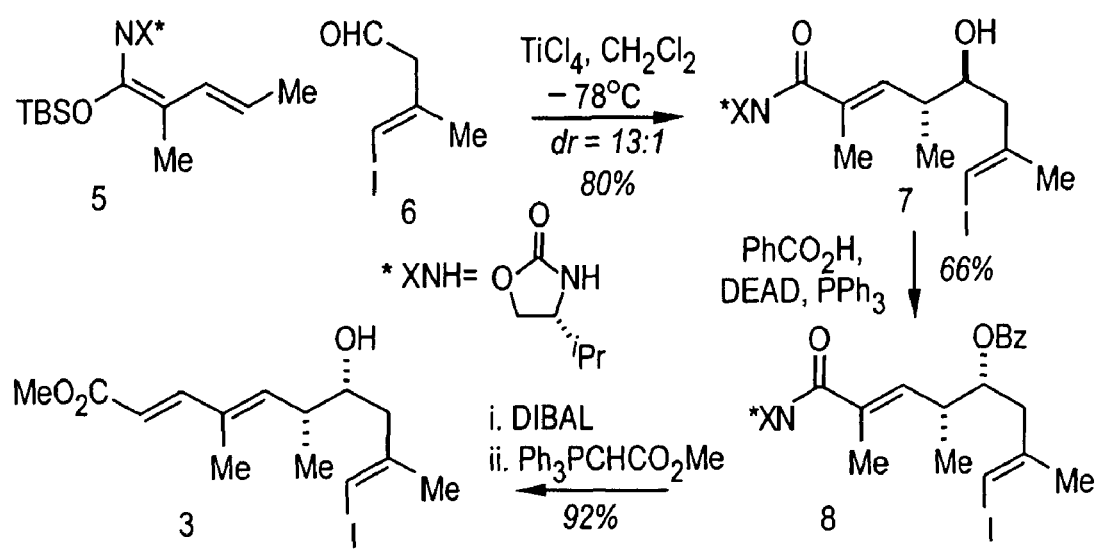
FIG. 2 is a scheme outlining steps in the preparation of a compound of Formula IIIA, according to one embodiment.
Figure 3:
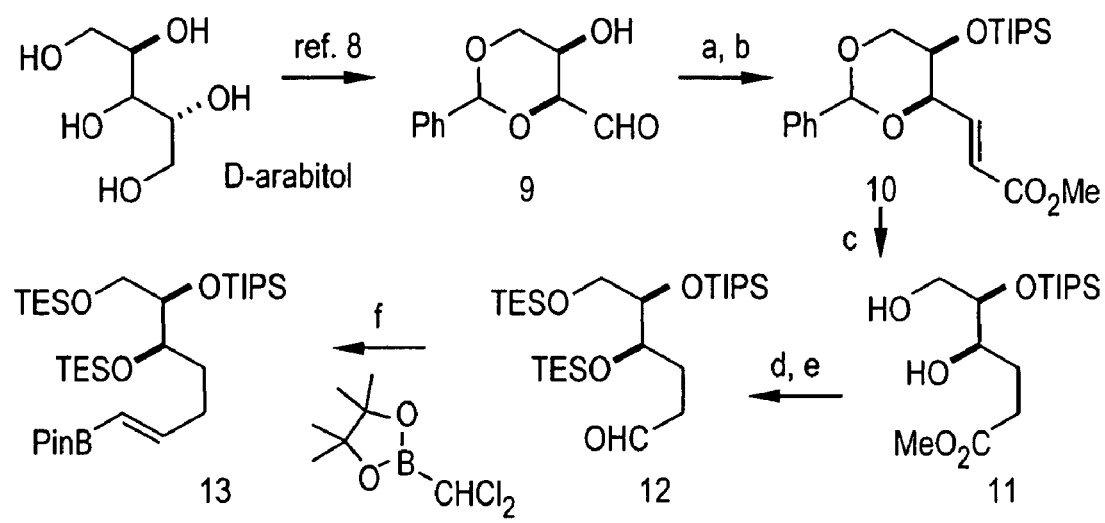
FIG. 3 is a scheme outlining steps in the preparation of a compound of Formula IIIA, according to one embodiment.

The synthesis of fragment 3 can be initiated by a vinylogous Mukaiyama aldol addition of vinylketene silyl N,O-acetal 5 to aldehyde 6 according to Kobayashi et al. to furnish alcohol 7 in excellent yield and diastereoselectivity (FIG. 2). A Mitsunobu inversion can then be used to provide the desired syn-isomer 8. Simultaneous reductive cleavage of the auxiliary and the benzoate provided an aldehyde that was homologated with $PPh_3CHCO_2Me$. Cross-coupling partner 3 thus was obtained, in 49% overall yield, from 5.

The synthetic equivalent of fragment 4, alkenylborane 13, can be derived from D-arabitol. Benzylidene acetal formation and oxidative α-diol cleavage to yield aldehyde 9 (see FIG. 3). Silylation, Wittig homologation, and hydrogenation can provide diol 11. Bis-silylether formation and ester reduction can be used to provide aldehyde 12-a material that can be condensed with pinacol dichloromethylboronate ($CrCl_2$, LiI) to yield vinylboronate 13.

Suzuki coupling of vinyl iodide 3 and vinylboronate 13 then can be performed with catalytic $Pd(PPh_3)_4$ and thallium carbonate as the base (FIG. 4). The coupled diene 14 can then be obtained was esterified with fragment 2, which was prepared in 5 steps from δ-valerolactone. Stirring the corresponding ester 15 in acidic MeOH then provided diol 16. Selective oxidation of the primary alcohol followed by Horner-Wadsworth-Emmons mediated macrocyclization can yield macrolactone 17 (70%). The steps of silylation (→18), CBS-reduction (→19, dr=4:1), and protection furnished TBS-ether 20 can then follow. Ester hydrolysis (($Bu_3Sn)_2O$, 81%) can set the stage for a Curtius rearrangement via azide 21.

Addition of 2-propenylmagnesium bromide to the isocyanate generated from heating acyl azide 21 yielded 22 (76%). Selective trimethylsilyl ether deprotection enabled introduction of the carbamate at C11 (23, 95%)—an operation that was followed by fluoride-mediated deprotection to afford target structure IIIA.

Confirmation of the stereochemical assignment of synthetic IIIA was founded on: (1) Mosher ester analysis of C7-alcohol 19; (2) C10, C11 stereochemistry from D-arabitol; and (3) X-ray analysis of fragment 7 (C19,20 stereochemistry). The absolute stereochemistry of 7 was confirmed by crystallographic analysis. The natural absolute configuration at C7 and C10 was ascertained by Mosher ester analysis. *J. Am. Chem. Soc.* 2006, 128, 5630. The relative C10-C11 and C19-C20 stereochemistry of natural palmerolide A is assigned by J-based H—H and C—H coupling constant analysis, and NOE-difference spectroscopy. *J. Am. Chem. Soc.* 2006, 128, 5630. Interpretation of ROESY data of the earlier structure proposed by Baker et al. parlaying stereochemistry from C11 to C19 was not convincing (*J. Am. Chem. Soc.* 2006, 128, 5630), thus the synthesis of the C19, 20-bis-epimer of IIIA, i.e. compound IIIB, was conducted.

Diastereomer IIIB was synthesized following the chemistry outlined in FIG. 4, but starting with the enantiomer of vinyl iodide 3, ent-3. The enantiomer of IIIB, ent-IIIB, can also be prepared by the appropriate enantiomeric selection of starting materials.

The described exemplary synthetic procedure illustrates that the procedures used can be utilized to prepare a broad range of materials having a macrocycle such as that found in the described palmerolides. By the appropriate selection of regioisomer and stereoisomer/enantiomer starting materials, the full range of palmerolide stereoisomers can be prepared.

DEFINITIONS

The following terms are used throughout as defined below.

"Palmerolide" is used here to refer generally to a macrocyclic polyketide lactone, having a structure of Formula II:

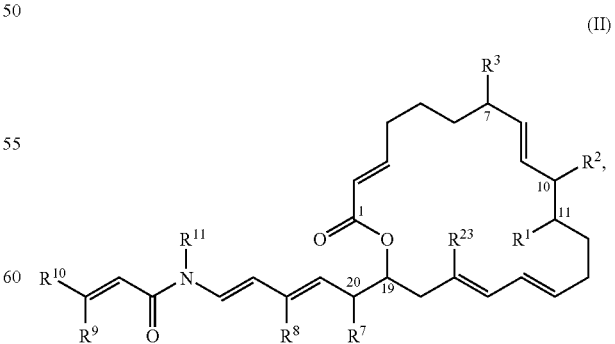

where $R^1$, $R^2$, $R^3$, $R^7$, $R^8$, $R^9$, $R^{10}$, $R^{11}$, and $R^{23}$ are as described vide infra. Palmerolide A is a particular species of palmerolide and is a compound of Formula ent-IIIB:

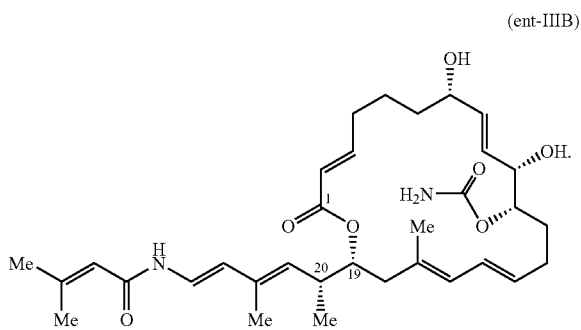

(ent-IIIB)

For the purposes of this disclosure and unless otherwise specified, "a" or "an" means "one or more."

Generally, reference to a certain element is meant to include all isotopes of that element. For example, if an R group is defined to include hydrogen or H, it also includes deuterium and tritium. Accordingly, isotopically labeled compounds are within the scope of the invention.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; ethers; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with substituted or unsubstituted alkyl, alkenyl, and alkynyl groups as defined below.

Alkyl groups include straight chain and branched alkyl groups having from 1 to about 20 carbon atoms, and typically from 1 to 12 carbons or, in some embodiments, from 1 to 8, 1 to 6, or 1 to 4 carbon atoms. Alkyl groups further include cycloalkyl groups as defined below. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, tert-butyl, neopentyl, isopentyl, and 2,2-dimethylpropyl groups. Representative substituted alkyl groups can be substituted one or more times with substituents such as those listed above.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include mono-, bicyclic and polycyclic ring systems, such as, for example bridged cycloalkyl groups as described below, and fused rings, such as, but not limited to, decalinyl, and the like. In some embodiments, polycyclic cycloalkyl groups have three rings. Substituted cycloalkyl groups can be substituted one or more times with, non-hydrogen and non-carbon groups as defined above. However, substituted cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups, which can be substituted with substituents such as those listed above. Cycloalkyl groups can also be bridged cycloalkyl groups in which two or more hydrogen atoms are replaced by an alkylene bridge, wherein the bridge can contain 2 to 6 carbon atoms if two hydrogen atoms are located on the same carbon atom, or 1 to 5 carbon atoms, if the two hydrogen atoms are located on adjacent carbon atoms, or 2 to 4 carbon atoms if the two hydrogen atoms are located on carbon atoms separated by 1 or 2 carbon atoms. Bridged cycloalkyl groups can be bicyclic, such as, for example bicyclo[2.1.1]hexane, or tricyclic, such as, for example, adamantyl. Representative bridged cycloalkyl groups include bicyclo[2.1.1]hexyl, bicyclo[2.2.1]heptyl, bicyclo[3.2.1]octyl, bicyclo[2.2.2]octyl, bicyclo[3.2.2]nonyl, bicyclo[3.3.1]nonyl, bicyclo[3.3.2]decanyl, adamantyl, noradamantyl, bornyl, or norbornyl groups. Substituted bridged cycloalkyl groups can be substituted one or more times with non-hydrogen and non-carbon groups as defined above. Representative substituted bridged cycloalkyl groups can be mono-substituted or substituted more than once, such as, but not limited to, mono-, di- or tri-substituted adamantyl groups, which can be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 20 carbon atoms, 4 to 16 carbon atoms, and typically 4 to 10 carbon atoms. Substituted cycloalkylalkyl groups can be substituted at the alkyl, the cycloalkyl or both the alkyl and cycloalkyl portions of the group. Representative substituted cycloalkylalkyl groups can be mono-substituted or substituted more than once, such as, but not limited to, mono-, di- or tri-substituted with substituents such as those listed above.

Alkenyl groups include straight and branched chain and cycloalkyl groups as defined above, except that at least one double bond exists between two carbon atoms. Thus, alkenyl groups have from 2 to about 20 carbon atoms, and typically from 2 to 12 carbons or, in some embodiments, from 2 to 8, 2 to 6, or 2 to 4 carbon atoms. In some embodiments, alkenyl groups include cycloalkenyl groups having from 4 to 20 carbon atoms, 5 to 20 carbon atoms, 5 to 10 carbon atoms, or even 5, 6, 7, or 8 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), CH=CHCH=CH$_2$, C(CH$_2$CH$_3$)=CH$_2$, cyclohexenyl, cyclopentenyl, cyclohexadienyl, butadienyl, pentadienyl, and hexadienyl, among others. Representative substituted alkenyl groups can be mono-substituted or substituted more than once, such as, but not limited to, mono-, di- or tri-substituted with substituents such as those listed above.

Cycloalkenylalkyl groups are alkyl groups as defined above in which a hydrogen or carbon bond of the alkyl group is replaced with a bond to a cycloalkenyl group as defined above. Substituted cycloalkylalkenyl groups can be substituted at the alkyl, the cycloalkenyl or both the alkyl and cycloalkenyl portions of the group. Representative substituted cycloalkenylalkyl groups can be substituted one or more times with substituents such as those listed above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8, 2 to 6, or 2 to 4 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others. Representative substituted alkynyl groups can be mono-substituted or substituted more than once, such as, but not limited to, mono-, di- or tri-substituted with substituents such as those listed above.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups can be mono-substituted or substituted more than once. For example, monosubstituted aryl groups include, but are not limited to, 2-, 3-, 4-, 5-, or 6-substituted phenyl or naphthyl groups, which can be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 20 carbon atoms, 7 to 14 carbon atoms or 7 to 10 carbon atoms. Substituted aralkyl groups can be substituted at the alkyl, the aryl or both the alkyl and aryl portions of the group. Representative aralkyl groups include but are not limited to benzyl and phenethyl groups and fused (cycloalkylaryl)alkyl groups such as 4-ethyl-indanyl. Representative substituted aralkyl groups can be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, heterocyclyl groups include 3 to 20 ring members, whereas other such groups have 3 to 6, 3 to 10, 3 to 12, or 3 to 15 ring members. Heterocyclyl groups encompass unsaturated, partially saturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups can be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridyl, pyridazinyl, pyrimidinyl, pyrazinyl, thiophenyl, benzothiophenyl, furanyl, benzofuranyl, indolyl, azaindolyl (pyrrolopyridyl), indazolyl, benzimidazolyl, imidazopyridyl (azabenzimidazolyl), pyrazolopyridyl, triazolopyridyl, benzotriazolyl, benzoxazolyl, benzothiazolyl, benzothiadiazolyl, imidazopyridyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups. Although the phrase "heteroaryl groups" includes fused ring compounds such as indolyl and 2,3-dihydro indolyl, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups can be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups can be substituted at the alkyl, the heterocyclyl or both the alkyl and heterocyclyl portions of the group. Representative heterocyclyl alkyl groups include, but are not limited to, 4-ethyl-morpholinyl, 4-propylmorpholinyl, furan-2-yl methyl, furan-3-yl methyl, pyridine-3-yl methyl, tetrahydrofuran-2-yl ethyl, and indol- 2-yl propyl. Representative substituted heterocyclylalkyl groups can be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups can be substituted at the alkyl, the heteroaryl or both the alkyl and heteroaryl portions of the group. Representative substituted heteroaralkyl groups can be substituted one or more times with substituents such as those listed above.

Groups described herein having two or more points of attachment (i.e., divalent, trivalent, or polyvalent) within the compound of the invention are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the invention are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups can be substituted one or more times with substituents such as those listed above.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups can be substituted one or more times with substituents such as those listed above.

The term "carboxylate" as used herein refers to a —COOH group.

The term "carboxylic ester" as used herein refers to —COOR$^{19}$ groups. R$^{19}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{11}$R$^{17}$, and —NR$^{11}$C(O)R$^{17}$ groups, respectively. R$^{11}$ and R$^{17}$ are at each occurrence independently H, OH, OR$^{14}$, SR$^{15}$, substituted or unsubstituted C$_{1-8}$ alkyl, substituted or unsubstituted C$_{1-8}$ alkenyl, substituted or unsubstituted C$_{1-8}$ alkynyl, substituted or unsubstituted aryl, substituted or unsubstituted aralkyl, substituted or unsubstituted heterocyclyl, substituted or unsubstituted heterocyclylalkyl, substituted or unsubstituted cycloalkyl, and substituted or unsubstituted cycloalkylalkyl as defined herein.

The term "amine" (or "amino") as used herein refers to —NHR$^{11}$ and —NR$^{11}$R$^{17}$ groups, wherein R$^{11}$ and R$^{17}$ are independently selected from H, OH, OR$^{14}$, SR$^{15}$, substituted or unsubstituted C$_{1-8}$ alkyl, substituted or unsubstituted C$_{1-8}$ alkenyl, substituted or unsubstituted C$_{1-8}$ alkynyl, substituted or unsubstituted aryl, substituted or unsubstituted aralkyl, substituted or unsubstituted heterocyclyl, substituted or unsubstituted heterocyclylalkyl, substituted or unsubstituted cycloalkyl, and substituted or unsubstituted cycloalkylalkyl as defined herein. In some embodiments, the amine is NH$_2$, methylamino, dimethylamino, ethylamino, diethylamino, propylamino, isopropylamino, phenylamino, or benzylamino.

The term "thiol" refers to —SH groups, while sulfides include —SR$^{15}$ groups, sulfoxides include —S(O)R$^{15}$ groups, sulfones include —SO$_2$R$^{15}$ groups, and sulfonyls include —SO$_2$OR$^{15}$. R$^{15}$ is at each occurrence H, substituted or unsubstituted C$_{1-8}$ alkyl, or a protecting group.

The term "enamine" refers to —C(R$^7$)=C(R$^8$)NR$^{11}$R$^{17}$ and —NR$^{11}$C(R$^7$)=C(R$^8$)R$^{8'}$, wherein R$^7$, R$^8$, and R$^{8'}$ are at each occurrence independently H, CN, F, Cl, Br, I, OR$^{14}$, SR$^{15}$, C$_{1-8}$ alkyl, cycloalkyl, cycloalkylalkyl, aryl, aralkyl, heterocyclyl, or heterocyclylalkyl as defined herein; R$^{11}$, and R$^{17}$ are at each occurrence as defined above; and R$^{14}$ and R$^{15}$ are at each occurrence independently selected from the group consisting of H, substituted or unsubstituted C$_{1-8}$ alkyl, and a protecting group; The term "dienamine" refers to —C(R$^7$)=C(R$^8$)C(R$^{8'}$)=C(R$^{8''}$)NR$^{11}$R$^{17}$; where R$^7$, R$^8$, R$^{8'}$, R$^{11}$, and R$^{17}$ are as defined above.

With respect to hydroxyl groups, amine groups, carboxy groups, and sulfhydryl groups, the qualifier "protected" denotes forms of these functionalities that are kept from undesirable reaction by means of protecting groups. Protecting groups are known in the art and can be added or removed using well-known procedures illustrated, for example, in "Protective Groups" in ORGANIC SYNTHESIS 3$^{rd}$ ed. (John Wiley & Sons, New York). Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylhiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate.

N-Protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Typical N-protecting groups are formyl, acetyl, benzoyl, pivaloyl, t-butylacetyl, phenylsulfonyl, benzyl, 9-fluorenylmethyloxycarbonyl (Fmoc), t-butyloxycarbonyl (Boc) and benzyloxycarbonyl (Cbz).

Representative carboxy protecting groups are $C_1$ to $C_8$ alkyl (e.g., methyl, ethyl or tertiary butyl and the like); haloalkyl; alkenyl; cycloalkyl and substituted derivatives thereof such as cyclohexyl, cyclopentyl and the like; cycloalkylalkyl and substituted derivatives thereof such as cyclohexylmethyl, cyclopentylmethyl and the like; arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxy)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(alkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl)methyl and the like.

The phrase "orthogonal protecting groups" refers to two, or more, compatible protecting groups which, in the presence of each other, can be differentially removed or, if not differentially, removed, can be differentially reprotected. In one embodiment, it can be desirable to remove all of the protecting groups in one step such as at completion of the synthesis.

Compounds of the invention can exhibit the phenomena of tautomerism, conformational isomerism, geometric isomerism and/or optical isomerism. As the formula drawings within the specification and claims can represent only one of the possible tautomeric, conformational isomeric, optical isomeric or geometric isomeric forms, it should be understood that the invention encompasses any tautomeric, conformational isomeric, optical isomeric and/or geometric isomeric forms of the compounds having one or more of the utilities described herein, as well as mixtures of these various different forms.

"Tautomers" refers to isomeric forms of a compound that are in equilibrium with each other. The concentrations of the isomeric forms will depend on the environment the compound is found in and can be different depending upon, for example, whether the compound is a solid or is in an organic or aqueous solution.

As readily understood by one skilled in the art, a wide variety of functional groups and other structures can exhibit tautomerism, and all tautomers of compounds as described herein are within the scope of the present invention.

Stereoisomers of compounds (also known as optical isomers) include all chiral, diastereomeric, and racemic forms of a structure, unless the specific stereochemistry is expressly indicated. Thus, compounds used in the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these are all within the scope of the invention.

"A Pharmaceutically acceptable carrier" refers to a carrier such as, but not limited to, a diluent, an excipients, a wetting agent, a buffering agent, a suspending agent, a lubricating agent, an adjuvant, a vehicle, a delivery system, an emulsifier, a disintegrant, an absorbent, a preservative, a surfactant, a colorant, a flavorant, a sweetener, or a mixture of any two or more thereof. pharmaceutically acceptable excipients and carriers are generally known to those skilled in the art and are thus included in the instant invention. Such materials are described, for example, in "Remingtons Pharmaceutical Sciences" Mack Pub. Co., New Jersey (1991), which is incorporated herein by reference.

"Prodrug" refers to a derivative of the inventive compounds that undergoes biotransformation, such as by metabolism, before exhibiting a pharmacological effect. Prodrugs can be formulated with the objective of improved chemical stability, improved patient acceptance and compliance, improved bioavailability, prolonged duration of action, improved organ selectivity, improved formulation (e.g., increased hydrosolubility), and/or decreased side effects (e.g., toxicity). Prodrug can be readily prepared from the inventive compounds using methods known in the art, such as those described in 1 BURGER'S MEDICINAL CHEMISTRY AND DRUG CHEMISTRY 5$^{th}$ ed., pages 172-178 and 949-982 (1995)

DESCRIPTION

In one aspect, the present invention contemplates compounds of Formula I, as well as tautomers of such compounds and pharmaceutically acceptable salts of such compound and tautomers, respectively. The compound of Formula I has the structure:

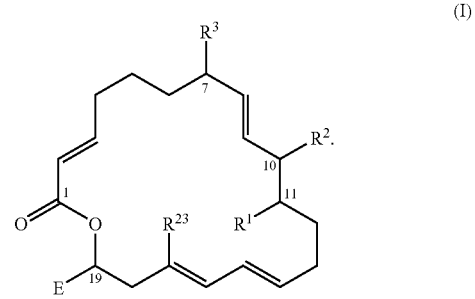

(I)

E may be a group such as, but not limited to substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkylalkenyl, substituted or unsubstituted cycloalkylalkynyl, substituted or unsubstituted aralkyl, substituted or unsubstituted aralkenyl, substituted or unsubstituted aralkynyl, substituted or unsubstituted heteroaralkyl, substituted or unsubstituted heteroaralkenyl, substituted or unsubstituted heteroaralkynyl, substituted or unsubstituted heterocyclylalkyl, substituted or unsubstituted heterocyclylalkenyl, substituted or unsubstituted heterocyclylalkynyl, substituted or unsubstituted eneamines, or substituted or unsubstituted dienamines. $R^1$ may be a group such as, but not limited to $OC(O)NR^{12}R^{13}$ or $OR^{18}$. $R^2$ may be a group such as, but not limited to F, Cl, Br, I, $NR^4R^5$, $OR^{14}$, or $SR^{15}$. $R^3$ may be a group such as, but not limited to F, Cl, Br, I, $NR^4R^5$, $OR^{14}$, $SR^{15}$, or =O. $R^4$, $R^5$, $R^{12}$, and $R^{13}$ may be, independently, a group such as, but not limited to H, OH, substituted or unsubstituted $C_{1-8}$ alkyl, substituted or unsubstituted aryl, substituted or unsubstituted aralkyl, substituted or unsubstituted heterocyclyl, substituted or unsubstituted heterocyclylalkyl, substituted or unsubstituted cycloalkyl, or substituted or unsubstituted cycloalkylalkyl. $R^{14}$ and $R^{15}$ at each occurrence may independently be a group such as, but not limited to H, substituted or unsubstituted $C_{1-8}$ alkyl, or a protecting group. $R^{18}$ at each occurrence may be a group such as, but not limited to H or a protecting group. $R^{23}$ may be a group such as, but not limited to H, CN, F, Cl, Br, I, $OR^{14}$, $SR^{15}$, or substituted or unsubstituted $C_{1-8}$ alkyl.

In some embodiments of the compound of Formula I, E is selected from a group such as

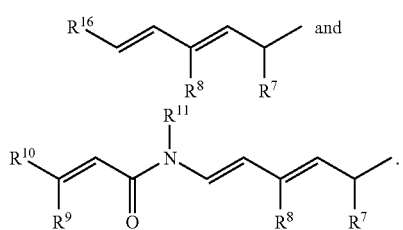

Each of $R^7$, $R^8$, $R^9$, and $R^{10}$ may be independently a group such as, but not limited to H, CN, F, Cl, Br, I, $OR^{14}$, $SR^{15}$, substituted or unsubstituted $C_{1-8}$ alkyl, substituted or unsubstituted cycloalkyl, substituted or unsubstituted or cycloalkylalkyl substituted or unsubstituted aryl, substituted or unsubstituted aralkyl, substituted or unsubstituted heterocyclyl, or substituted or unsubstituted heterocyclylalkyl. $R^{11}$ may be a group such as, but not limited to H, OH, substituted or unsubstituted $C_{1-8}$ alkyl, substituted or unsubstituted aryl, substituted or unsubstituted aralkyl, substituted or unsubstituted heterocyclyl, substituted or unsubstituted heterocyclylalkyl, substituted or unsubstituted cycloalkyl, or substituted or unsubstituted cycloalkylalkyl. $R^{16}$ may be a group such as, but not limited to substituted or unsubstituted $C_{1-8}$ alkyl, substituted or unsubstituted aryl, substituted or unsubstituted aralkyl, substituted or unsubstituted heterocyclyl, substituted or unsubstituted heterocyclylalkyl, substituted or unsubstituted cycloalkyl, substituted or unsubstituted cycloalkylalkyl, carboxylate, carboxylic ester, amine, $NR^{11}R^{17}$, or $NR^{11}C(O)R^{17}$. $R^{17}$ may be a group such as, but not limited to H, OH, $OR^{14}$, $SR^{15}$, substituted or unsubstituted $C_{1-8}$ alkyl, substituted or unsubstituted $C_{1-8}$ alkenyl, substituted or unsubstituted $C_{1-8}$ alkynyl, substituted or unsubstituted aryl, substituted or unsubstituted aralkyl, substituted or unsubstituted heterocyclyl, substituted or unsubstituted heterocyclylalkyl, substituted or unsubstituted cycloalkyl, or substituted or unsubstituted cycloalkylalkyl.

In some embodiments of the compound of Formula I, E is a group of formula

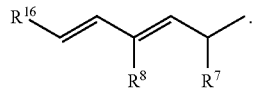

In such embodiments, $R^7$ and $R^8$ are independently a group such as, but not limited to H, $OR^{14}$, or substituted or unsubstituted $C_{1-3}$ alkyl; $R^{16}$ may be a group such as, but not limited to carboxylate, carboxylic ester, amine, $NR^{17}R^{17}$, and $NR^{11}C(O)R^{17}$; $R^{11}$ may be a group such as, but not limited to H and substituted or unsubstituted $C_{1-3}$ alkyl; $R^{17}$ may be a group such as, but not limited to H, OH, $OR^{14}$, $SR^{15}$, —C≡$CR^{22}$, or —$CR^{24}$=$CR^{25}R^{26}$; and $R^{22}$, $R^{24}R^{25}$, and $R^{26}$ may be independently a group such as, but not limited to H, substituted or unsubstituted $C_{1-8}$ alkyl, substituted or unsubstituted $C_{1-8}$ alkenyl, substituted or unsubstituted $C_{1-8}$ alkynyl, substituted or unsubstituted cycloalkyl, substituted or unsubstituted aryl, substituted or unsubstituted aralkyl, substituted or unsubstituted heteroaryl, substituted or unsubstituted heteroaralkyl, substituted or unsubstituted heterocyclyl, or substituted or unsubstituted heterocyclylalkyl.

Alternatively, $R^7$ and $R^8$ may be independently H, methyl or ethyl; $R^{16}$ may be carboxylate, carboxylic ester, or $NR^{11}C(O)R^{17}$; $R^{11}$ may be H; $R^{17}$ may be —C≡$CR^{22}$, or —$CR^{24}$=$CR^{25}R^{26}$; and $R^{22}$, $R^{24}$, $R^{25}$, and $R^{26}$ may be, independently, H, methyl, ethyl, propyl, iso-propyl, butyl, sec-butyl, tert-butyl, substituted phenyl, or substituted benzyl.

In some embodiments of the compound of Formula I, E is a group of formula

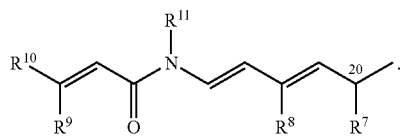

In such embodiments, $R^2$ and $R^3$ may be independently a group such as, but not limited to $OR^{14}$; $R^7$, $R^8$, $R^9$, and $R^{10}$ may be, independently, a group such as, but not limited to H, $OR^{14}$, or substituted or unsubstituted $C_{1-3}$ alkyl; $R^{11}$, $R^{12}$, and $R^{13}$ may be independently a group such as, but not limited to H or substituted or unsubstituted $C_{1-3}$ alkyl; $R^{14}$ at each occurrence may be independently a group such as, but not limited to H or a protecting group; and $R^{23}$ may be a group such as, but not limited to methyl or ethyl.

The compound of Formula I has at least four stereocenters located at the carbon atoms labeled 7, 10, 11, and 19. Thus, the possible stereoisomers for the respective carbon atoms are RRRR, RRRS, RRSR, RSRR, SRRR, RRSS, RSRS, RSSR, SRRS, SRSR, SSRR, RSSS, SRSS, SSRS, SSSR, and SSSS. Depending upon the substitutents, other stereocenters may be introduced.

In another aspect, the compound of Formula I is represented by the compound of Formula II. Such description of the compound of Formula II also includes tautomer of the compound and pharmaceutically acceptable salts of the compound or the tautomer. The compound of Formula II has the structure:

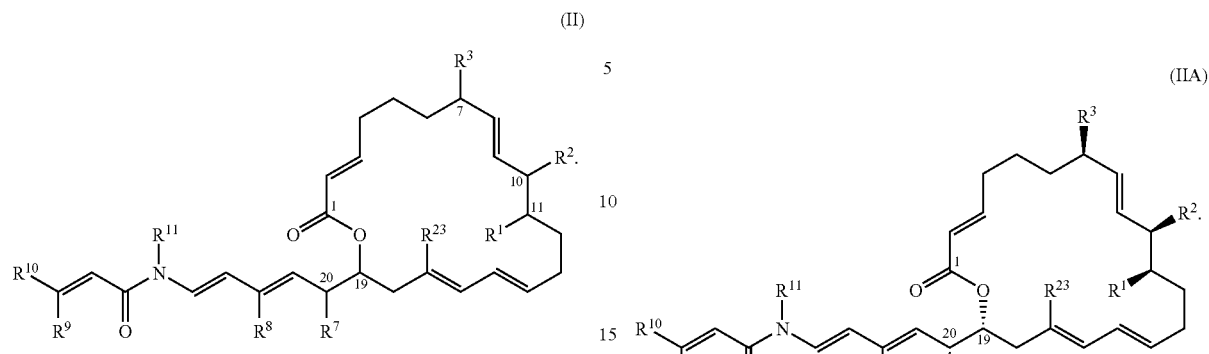

(II)

The compound of Formula II has at least five stereocenters. The five stereocenters are located at the carbon atoms labeled 7, 10, 11, 19, and 20. At each stereocenter the labeled carbon atom can be an R or S isomer. Table 1 lists the possible stereocenter combinations.

TABLE 1

Stereoisomers of the Compound of Formula II:

| C-7 | C-10 | C-11 | C-19 | C-20 |
|-----|------|------|------|------|
| R | R | R | R | R |
| R | R | R | R | S |
| R | R | R | S | R |
| R | R | S | R | R |
| R | S | R | R | R |
| S | R | R | R | R |
| R | R | R | S | S |
| R | R | S | R | S |
| R | R | S | S | R |
| R | S | R | R | S |
| R | S | R | S | R |
| R | S | S | R | R |
| S | R | R | R | S |
| S | R | R | S | R |
| S | R | S | R | R |
| S | S | R | R | R |
| R | R | S | S | S |
| R | S | R | S | S |
| R | S | S | R | S |
| R | S | S | S | R |
| S | R | R | S | S |
| S | R | S | R | S |
| S | R | S | S | R |
| S | S | R | R | S |
| S | S | R | S | R |
| S | S | S | R | R |
| R | S | S | S | S |
| S | R | S | S | S |
| S | S | R | S | S |
| S | S | S | R | S |
| S | S | S | S | R |
| S | S | S | S | S |

In some embodiments, the compound of Formula II has the stereochemical orientation of Formula IIA:

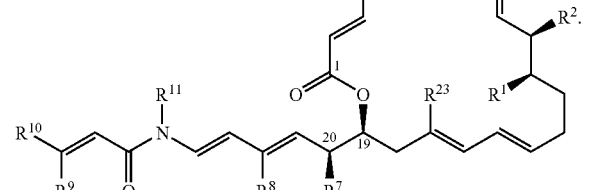

(IIA)

In some embodiments, the compound of Formula II has the stereochemical orientation of Formula IIB:

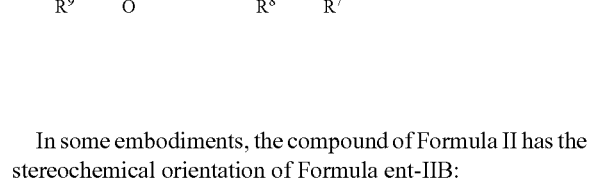

(IIB)

In some embodiments, the compound of Formula II has the stereochemical orientation of Formula ent-IIB:

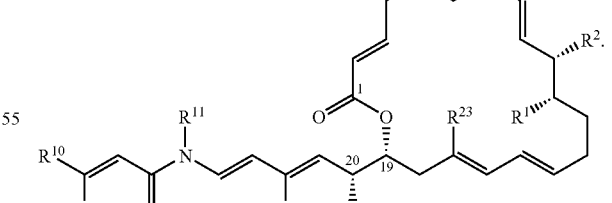

(ent-IIB)

In some embodiments, the compound of Formula II is represented by the compound of Formula III, a tautomer of the compound, a pharmaceutically acceptable salt of the compound, or a pharmaceutically acceptable salt of the tautomer.

The compound of Formula III has the structure:

(III)

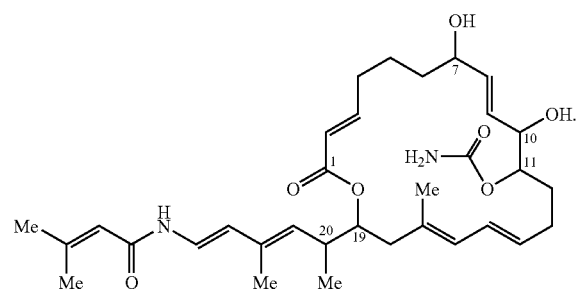

The compound of Formula III can also have a variety of stereochemical representations as correspondingly shown in Table 1. For example, in some embodiments, the compound of Formula III is represented by the compound of Formula IIIB or ent-IIIB:

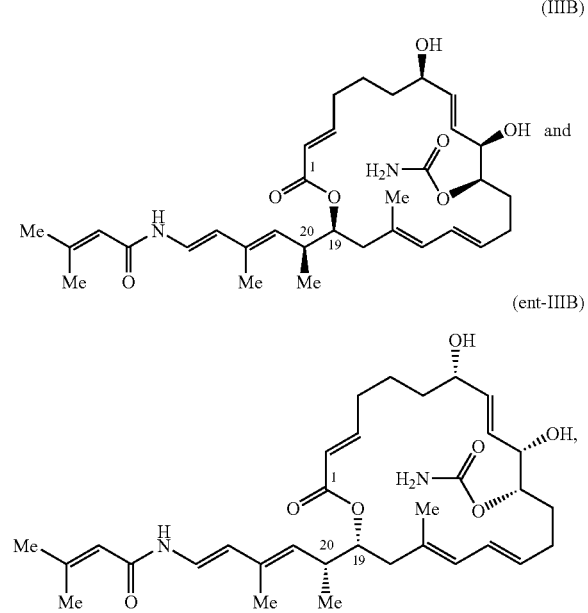

(IIIB)

and (ent-IIIB)

respectively.

In another aspect, processes of preparing the embodied compounds are also provided. In some embodiments, the process comprises deprotection of a precursor, such as the compound of Formula IV.

(IV)

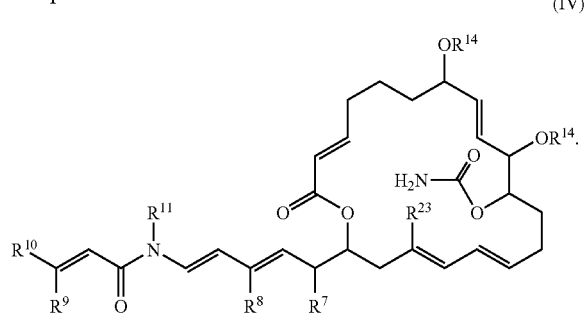

In such embodiments, the $R^{14}$ groups may be a protecting group for the corresponding oxygen atom. Such protecting groups include, but are not limited to trimethylsilyl, triethylsilyl, tripropylsilyl, triisopropylsilyl, tributylsilyl, tert-butyldimethylsilyl, or tert-butyldiphenylsilyl. Where both $R^{14}$ are individually protecting groups at each occurrence, the groups can be orthogonal protecting groups. Deprotection to yield an alcohol group is known to those of skill in the art, and can include, but is not limited to the use of a source of fluoride ion. Such sources of fluoride ion include, but are not limited to, tetralkylammonium fluoride, cesium fluoride, HF, or a mixture of any two or more thereof. Tetraalkylammonium fluorides are known to those of skill in the art and can include, but are not limited to, tetramethylammonium fluoride, tetraethyl ammonium fluoride, tetrapropylammonium fluoride, and/or tetrabutylammonium fluoride. The compound of Formula IV can have any of the stereochemical orientations described in Table 1, including those represented by Formulas IVA, IVB, and ent-IVB. The compounds of Formulas IVA, IVB, and ent-IVB are, respectively:

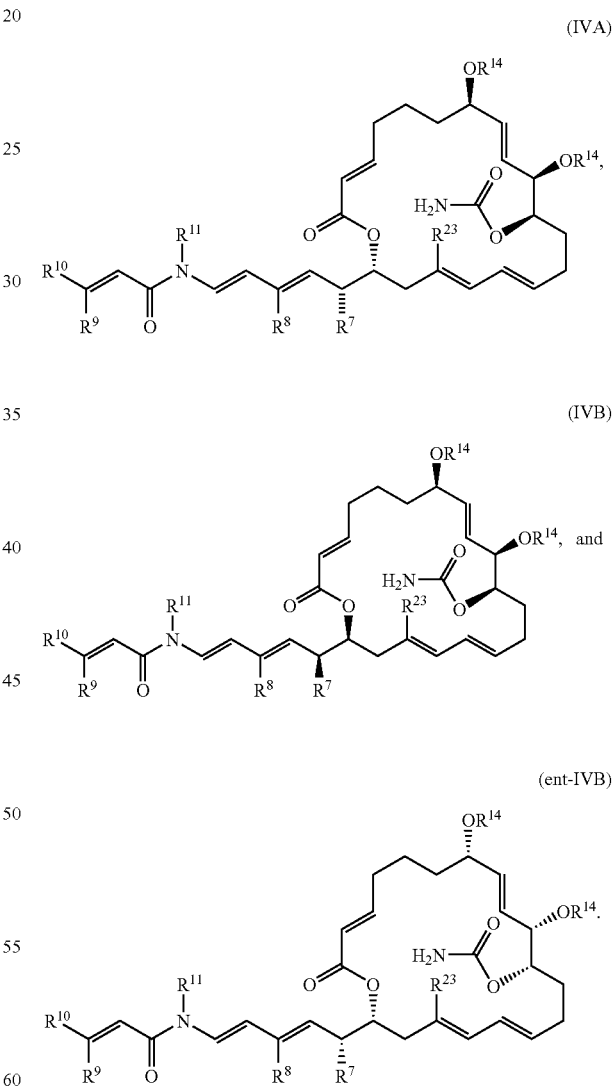

(IVA)

(IVB)

and (ent-IVB)

In other embodiments, the processes of preparing the embodied compounds include preparing the compound of Formula IV by reacting a compound of Formula V with $X_3C(O)NCO$, where X is a halogen. The compound of Formula V can be structurally represented as:

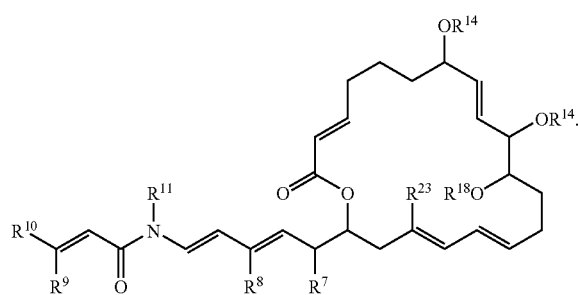

(V)

In such embodiments, $R^{18}$ is H, or a protecting group. In some embodiments, the protecting group is selected from, but is not limited to, trimethylsilyl, triethylsilyl, tripropylsilyl, triisopropylsilyl, tributylsilyl, tert-butyldimethylsilyl, or tert-butyldiphenylsilyl. Where $R^{14}$ and/or $R^{18}$ are each individually a protecting group at each occurrence, they can be orthogonal protecting groups. Stereochemical isomers of the compound of Formula V include those isomers as described in Table I. For example, the compounds Formula V can have the structures represented by the compounds of Formulas VA, VB, and ent-VB, but they are not so limited. The compounds of Formulas VA, VB, and ent-VB are structurally represented by, respectively:

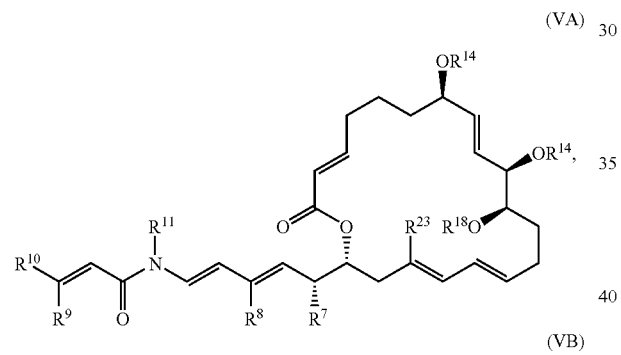

(VA)

(VB)

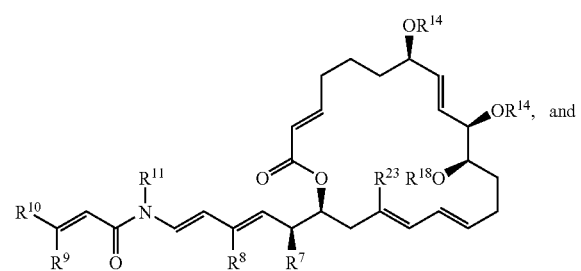

(ent-VB)

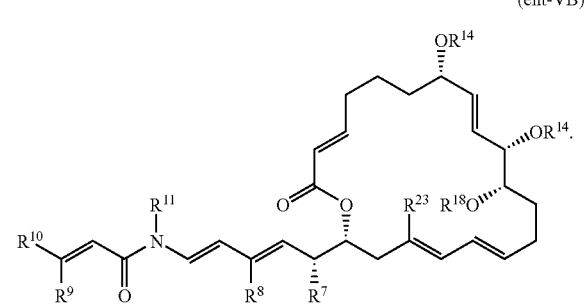

In some embodiments, the processes of preparing the compounds embodied herein include preparing a compound of Formula VIIC or VIID via the reduction of a compound of Formula VI with a stereospecific reducing agent. The compounds of Formula VI, VIIC, and VIID are respectively:

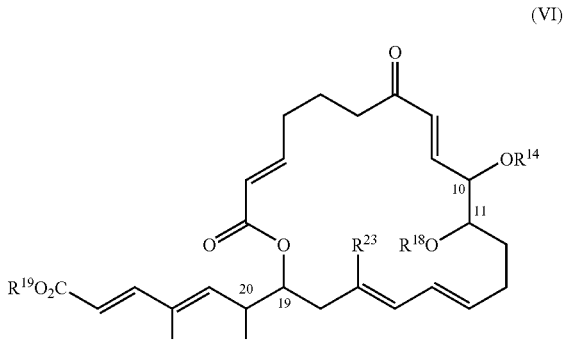

(VI)

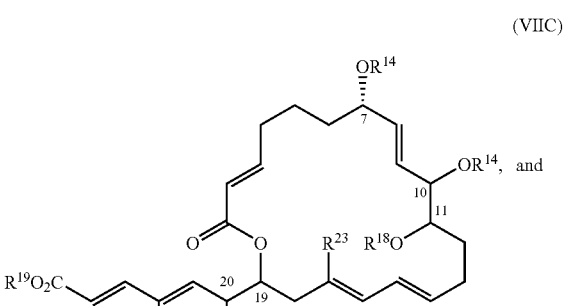

(VIIC)

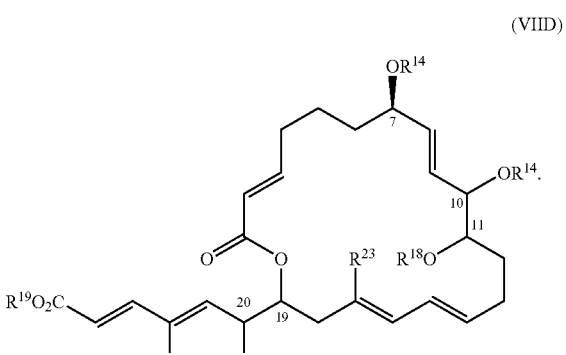

(VIID)

The stereospecific reducing agent can be (S)-2-methyl-CBS-oxazaborolidine or (R)-2-methyl-CBS-oxazaborolidine, but is not so restricted. As will be recognized by those of skill in the art, the compound of Formula VI has at least four stereoisomers at carbon atoms labeled 10, 11, 19, and 20. Such stereoisomers have their relative stereochemical orientations preserved upon reduction by the stereo specific reducing agent. In some embodiments, the compound of Formula VI is provided, and can include the various stereochemical configurations according to those listed in Table 1 for the carbon atoms at positions 10, 11, 19, and 20. For example, and without limitation, the compound of Formula VI can be represented as the compounds of Formula VIA, VIB, or ent-VIB, respectively,

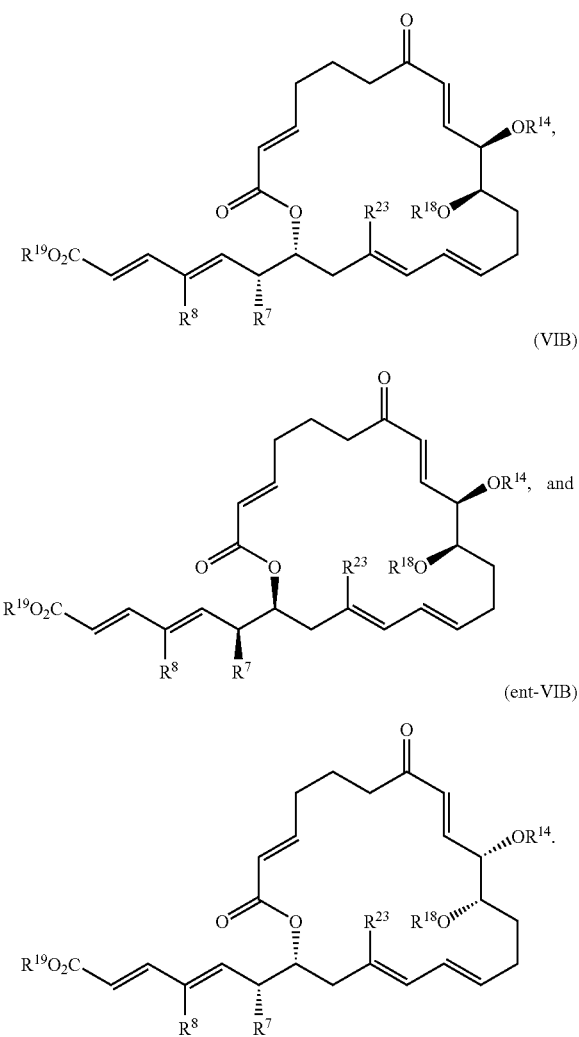

(VIA)

(VIB)

(ent-VIB)

In other embodiments the process of preparing the embodied compounds includes the compound of Formula VIII, a tautomer thereof, or a pharmaceutically acceptable salt of either:

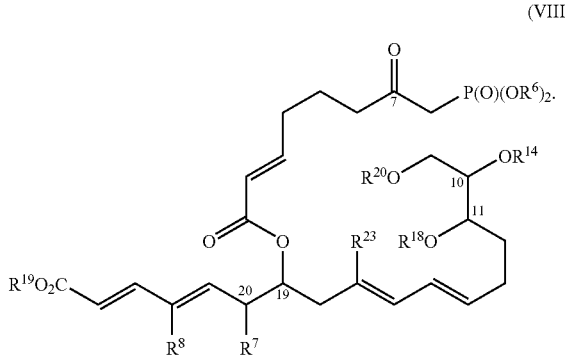

(VIII)

In such embodiments, $R^7$ and $R^8$ are independently H, OH, SH, CN, F, Cl, Br, I, $OR^{14}$ $SR^{15}$, substituted or unsubstituted $C_{1-8}$ alkyl, substituted or unsubstituted cycloalkyl, substituted or unsubstituted or cycloalkylalkyl substituted or unsubstituted aryl, substituted or unsubstituted aralkyl, substituted or unsubstituted heterocyclyl, or substituted or unsubstituted heterocyclylalkyl; $R^6$ and $R^{19}$ are independently H or a substituted or unsubstituted $C_{1-4}$ alkyl; and $R^{14}$, $R^{18}$, and $R^{20}$ are independently H or a protecting group.

The compound of Formula VIII has number of possible stereoisomers, including those listed in Table for carbons 10, 11, 19, and 20, as shown in Formula VIII.

In some embodiments, the compound of Formula VIII, $R^{14}$, $R^{18}$, and $R^{20}$ are independently selected from, but are not limited to, H, trimethylsilyl, triethylsilyl, tripropylsilyl, triisopropylsilyl, tributylsilyl, and tert-butyldimethylsilyl; $R^{19}$ is methyl or ethyl; and $R^6$ is methyl or ethyl. Where the compound includes protecting groups at $R^{14}$, $R^{18}$, and $R^{20}$, those protecting groups can be orthogonal protecting groups.

In other embodiments, the processes involve the cyclization of the compound of Formula VIII to prepare the compound of Formula VI. Such cyclization can be effected via a selective oxidation, followed by addition of a base. Such process can involve a Horner-Wadsworth-Emmons-mediated cyclization.

In some embodiments, the process comprises coupling a compound of Formula IX and a compound of Formula X:

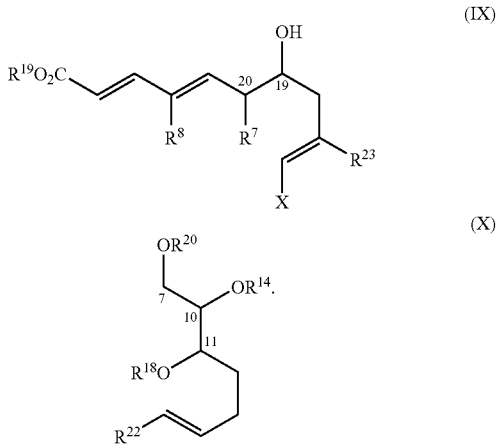

In such embodiments, X may be a group such as, but not limited to F, Cl, Br, or I; $R^{19}$ may be a group such as, but not limited to methyl or ethyl; and $R^{22}$ may be a group such as, but not limited to a boron-based protecting group or an trialkyltin. For example, boron-based protecting groups can include, but are not limited to pinacolboronate, catecholboronate, 9-borabicyclononyl, or dicyclohexylborane. Suitable trialkyltin groups are known to those of skill in the art and can include, but are not limited to, trimethyltin, triethyltin, tripropyltin, triisopropyltin, and tributyltin. The coupling can be done by processes known to those of skill in the art including, but not limited to a Suzuki coupling or Stille coupling. In some cases, Stille coupling can be used where $R^{22}$ is a trialkyltin. The stereochemistry of the compounds of Formulas IX and X at carbon atoms labeled 7, 10, 11, 19, and 20 can be as shown in Table 1.

In another aspect, pharmaceutical compositions of the compounds are provided. Such compositions include, but are not limited to a therapeutically effective amount of the compound of Formula I, a tautomer of the compound, a pharmaceutically acceptable salt of the compound, a pharmaceutically acceptable salt of the tautomer, or a mixture of any two or more thereof, and a pharmaceutically acceptable carrier. Such pharmaceutically acceptable carriers are known to those of skill in the art and include, but are not limited to, diluents, excipients, wetting agents, buffering agents, suspending agents, lubricating agents, adjuvants, emulsifiers, disintegrants, absorbents, preservatives, surfactants, colorants, flavorants, sweeteners, or a mixture of any two or more thereof.

One skilled in the art will readily realize that all ranges and ratios discussed can and do necessarily also describe all subranges and subratios therein for all purposes and that all such subranges and subratios also form part and parcel of this invention. Any listed range or ratio can be easily recognized as sufficiently describing and enabling the same range or ratio being broken down into at least equal halves, thirds, quarters, fifths, tenths, etc. As a non-limiting example, each range or ratio discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

EXPERIMENTAL

Generally

Unless otherwise noted, commercially available materials were used without further purification. All solvents were of HPLC (high performance liquid chromatography) or ACS (American Chemical Society) grade. Solvents used for moisture sensitive operations were dried over molecular sieves (Aldrich, 4 Å), pyridine over solid KOH, anhydrous N,N-dimethylformamide, and CH$_3$CN were purchased from commercial sources. Reactions were performed under an atmosphere of nitrogen with magnetic stirring unless noted otherwise. Flash chromatography (FC) was performed using E Merck silica gel 60 (240-400 mesh) according to the protocol of Still, Kahn, and Mitra (*J. Org. Chem.* 1978, 43, 2923). Thin layer chromatography was performed using precoated plates purchased from E. Merck (silicagel 60 PF254, 0.25 mm) that were visualized using a KMnO$_4$ or Ce (IV) stain.

Nuclear magnetic resonance (NMR) spectra were recorded on a Varian Inova-400 or Mercury-300 spectrometer at operating frequencies of 400/300 MHz ($^1$H NMR) or 100/75 MHz ($^{13}$C NMR). Chemical shifts (δ) are given in ppm relative to residual solvent (usually chloroform δ 7.26 for $^1$H NMR or δ 77.23 for proton decoupled $^{13}$C NMR), and coupling constants (J) in Hz. Multiplicity is tabulated as (s) for singlet, (d) for doublet, (t) for triplet, (q) for quadruplet, and (m) for multiplet, whereby the prefix app is applied in cases where the true multiplicity is unresolved, and br when the signal in question is broadened.

Infrared spectra were recorded on a Perkin-Elmer 11000 series FTIR (Fourier Transform Infrared) with wavenumbers expressed in cm$^{-1}$ using samples prepared as thin films between salt plates. Electrospray ionization mass spectra (ESI-MS) were recorded on a Shimadzu 2010-LCMS. Optical rotations were measured at 20° C. on a Rudolph Research Analytical Autopol® IV polarimeter.

Compound 5 was prepared according to the procedure of Shirokawa et al., *J. Am. Chem. Soc.* 126: 13604-605 (2004). Compound 6 was prepared according to the procedure of Marshall et al., *Org. Lett.* 6: 445-48 (2004). Aldehyde 9 was prepared according to the procedure of Urbansky et al., *Org. Lett.* 6: 135-38 (2004). Pinacol dichloromethylboronate was prepared by the method of Wuts et al., *J. Organometal. Chem.* 234: 137-41 (1982). Aldehyde iv was prepared via the procedure of Govoni et al., *J. Med. Chem.* 49: 2549-57 (2006).

Procedures

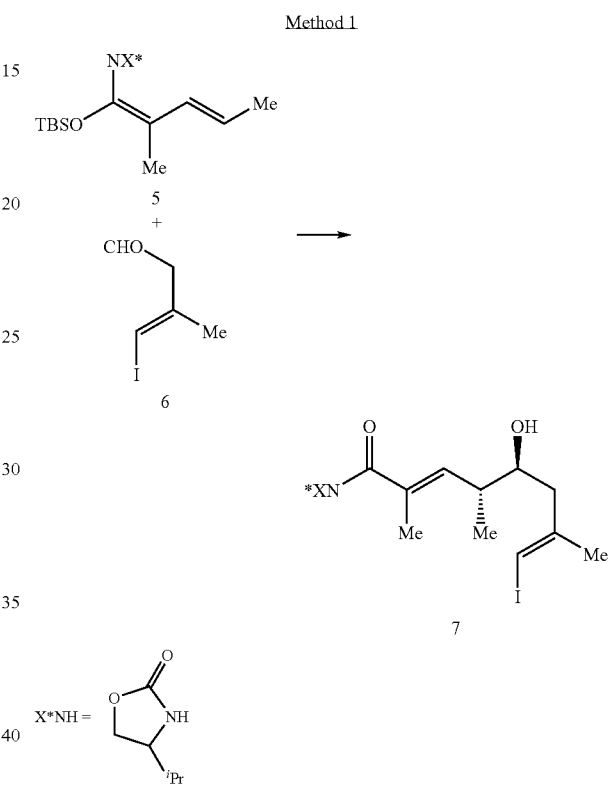

To a solution of compound 5 (1.01 g, 3.00 mmol) and aldehyde 6 (1.20 g, 5.71 mmol) in CH$_2$Cl$_2$ (20 ml) was added TiCl$_4$ (329 μL, 3.00 mmol) at −78° C. under Ar. After stirring at −78° C. for 16 h, aq. Na,K-tartrate (50 mL) and aq. NaHCO$_3$ (50 mL) were added. The mixture was stirred vigorously at rt until the resulting white slurry was completely dissolved. Crude 7 was extracted with CH$_2$Cl$_2$ and the combined organic phases were washed with water and dried over MgSO4, filtered and concentrated. The residue obtained was purified by FC (silica gel, Hexanes/EtOAc 5:1) to afford compound 7 (1.31 g, 80%, 13:1 dr) as a white solid. Mp. 95~96° C. (CH$_2$Cl$_2$/hexanes); [α]$_D$=−40 (CHCl$_3$, c 0.32); $^1$H NMR (400 MHz, CDCl$_3$) δ 0.91 (d, 3H, J=6.8 Hz), 0.92 (d, 3H, J=6.8 Hz), 1.02 (d, 3H, J=6.4 Hz), 1.89 (d, 3H, J=0.8 Hz), 1.92 (d, 3H, J=1.6 Hz), 2.33 (dqq, 1H, J=4.4, 6.8, 6.8 Hz), 2.39 (dd, 1H, J=9.2, 14.0 Hz), 2.47 (dd, 1H, J=2.8, 14.0 Hz), 2.56 (ddq, 1H, J=?, 6.4, 10.4 Hz), 2.98 (d, 1H, J=2.0 Hz), 3.55 (m, 1H), 4.18 (dd, 1H, J=5.6, 9.2 Hz), 4.34 (dd, 1H, J=8.8, 9.2 Hz), 4.57 (ddd, 1H, J=4.8, 5.6, 10.6 Hz), 5.82 (dd, 1H, J=1.6, 10.4 Hz), 6.03 (d, 1H, J=0.8 Hz); $^{13}$C NMR (100 MHz, CDCl$_3$) δ 13.9, 15.1, 16.2, 17.8, 24.1, 28.3, 39.6, 43.8, 58.0, 63.4, 73.1, 131.3, 140.9, 145.1, 154.4, 171.4; IR: 3511, 2965, 2929, 1778, 1738, 1683, 1373, 1242; MS (ES) calc. for C$_{17}$H$_{26}$INO$_4$Na [MNa]$^+$458.1; found 458.1.

Method 2

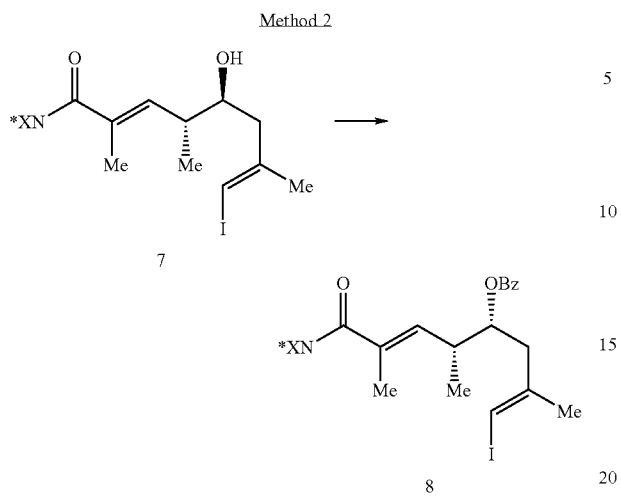

To a clear solution of PPh$_3$ (3.69 g, 14.08 mmol) and benzoic acid (2.58 g, 21.14 mmol) in toluene (50 mL), was added DEAD (2.44 mL, 15.49 mmol) at 0° C. A solution of compound 7 (1.53 g, 3.52 mmol) in toluene (10 mL) was then added over 10 min. After stirring at 0° C. for 2 h, the reaction mixture was concentrated and purified by FC (silica gel, CH$_2$Cl$_2$) to give compound 8 (1.25 g, 66%) as a white solid. $[\alpha]_D$=+34.6 (CH$_2$Cl$_2$, c 0.40); $^1$H NMR (400 MHz, CDCl$_3$) δ 0.91 (s, 3H, J=6.8 Hz), 0.93 (d, 3H, J=6.8 Hz), 1.07 (d, 3H, J=6.4 Hz), 1.88 (s, 3H), 1.92 (d, 3H, J=1.6 Hz), 2.37 (dqq, 1H, J=4.4, 6.8, 6.8 Hz), 2.62 (dd, 1H, J=8.8, 14.0 Hz), 2.72 (dd, 1H, J=2.8, 14.0 Hz), 2.90 (m, 1H), 4.19 (dd, 1H, J=5.6, 8.8 Hz), 4.33 (dd, 1H, J=8.8, 9.2 Hz), 4.53 (m, 1H), 5.19 (ddd, 1H, J=2.8, 8.0, 8.8 Hz), 5.85 (dd, 1H, J=1.6, 10.0 Hz), 6.01 (bs, 1H), 7.45 (dd, 2H, J=7.6, 8.4 Hz), 7.57 (t, 1H, J=7.6 Hz), 8.03 (d, 2H, J=8.8 Hz); $^{13}$C NMR (100 MHz, CDCl$_3$) δ 13.9, 15.0, 16.0, 17.7, 24.1, 28.1, 36.9, 41.8, 58.0, 63.3, 75.0, 78.1, 128.3, 129.4, 129.9, 131.8, 132.9, 138.3, 143.9, 153.4, 165.8, 171.3; IR: 2965, 1783, 1715, 1683, 1450, 1372, 1270, 1110; MS (ES) calc. for C$_{24}$H$_{30}$INO$_5$Na [MNa]$^+$562.1, found 562.1.

Method 3

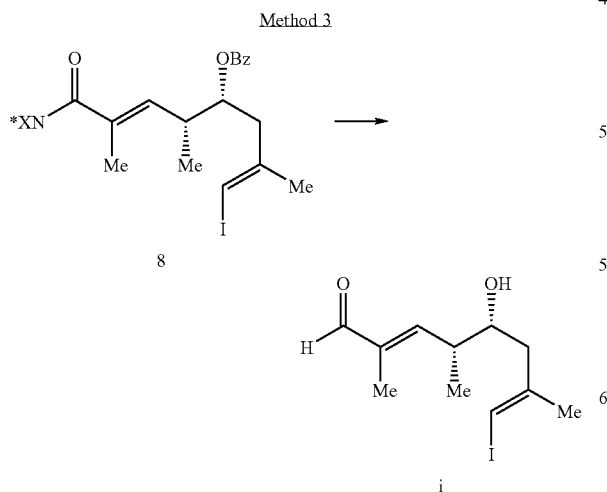

DIBAL-H (1M in toluene, 6.90 mL, 6.90 mmol) was added dropwise to a solution of compound 8 (1.00 g, 2.30 mmol) in CH$_2$Cl$_2$ (30 mL) at −78° C. under N$_2$. After stirring for 2 h, MeOH (1 mL) was added followed by aq. Na,K-tartrate (20 mL) and the reaction mixture was warmed to rt and stirred for 2 h. Crude i was extracted with CH$_2$Cl$_2$ and the combined organic phases were dried over Na$_2$SO$_4$, filtered and concentrated. The residue obtained was purified by FC (silica gel, Hexanes/Ether 2:1 to 1:1) to afford aldehyde i (529 mg, 93%) as a viscous oil. $^1$H NMR (400 MHz, CDCl$_3$) δ 1.15 (d, 3H, J=6.8 Hz), 1.78 (d, 3H, J=1.2 Hz), 1.88 (d, 3H, J=0.8 Hz), 2.32 (dd, 1H, J=9.2, 14.0 Hz), 2.38 (dd, 1H, J=2.8, 14.0 Hz), 2.76 (ddq, 1H, J=6.4, 6.8, 10.0 Hz), 3.69 (ddd, 1H, J=3.6, 6.4, 9.6 Hz), 6.05 (bs, 1H), 6.38 (dd, 1H, J=1.2, 10.0 Hz), 9.40 (s, 1H); $^{13}$C NMR (100 MHz, CDCl$_3$) δ 9.6, 14.9, 23.9, 39.3, 45.2, 71.5, 77.9, 139.2, 144.4, 155.5, 195.3.

Method 4

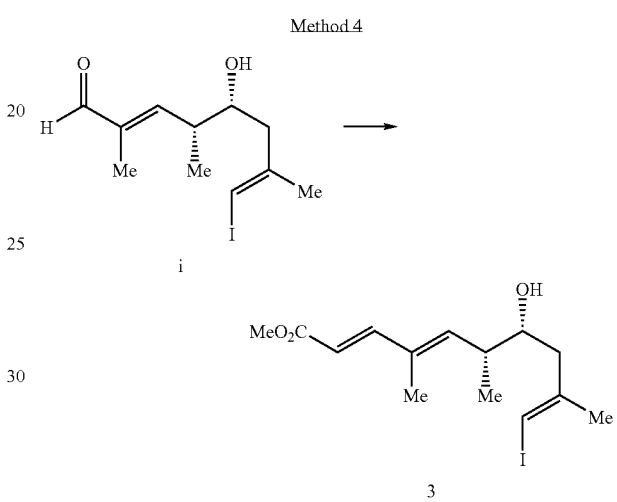

A solution of aldehyde i (520 mg, 1.69 mmol) and methyl (triphenylphosphoranylidene)acetate (1.69 g, 5.06 mmol) in benzene (25 mL) was refluxed for 5 h under N$_2$. After concentration, the residue was purified by FC (silica gel, Hexanes/EtOAc 8:1) to afford compound 3 (590 mg, 97%) as a viscous oil. $[\alpha]_D$=+33.0 (CH$_2$Cl$_2$, c 0.23); $^1$H NMR (400 MHz, CDCl$_3$) δ 1.08 (d, 3H, J=6.4 Hz), 1.80 (d, 3H, J=1.2 Hz), 1.86 (d, 3H, J=0.8 Hz), 2.24 (dd, 1H, J=10.0, 14.0 Hz), 2.38 (dd, 1H, J=bd, 1H, J=14.0 Hz), 2.60 (ddq, 1H, J=6.0, 6.4, 10.0 Hz), 3.57 (m, 1H), 3.75 (d, 1H, J=10.0 Hz), 5.73 (d, 1H, J=10.0 Hz), 5.83 (d, 1H, J=16.0 Hz), 6.01 (bs, 1H), 7.31 (d, 1H, J=16.0 Hz); $^{13}$C NMR (75 MHz, CDCl$_3$) δ 12.6, 16.0, 23.9, 39.3, 45.3, 51.5, 72.4, 77.4, 116.1, 133.1, 143.2, 144.9, 149.4, 167.8; IR: 3437, 2949, 1713, 1623, 1435, 1314, 1276, 1172, 1016; MS (ES) calc. for C$_{14}$H$_{22}$IO$_3$ [MH]$^+$ 365.1, found 365.1.

Method 5

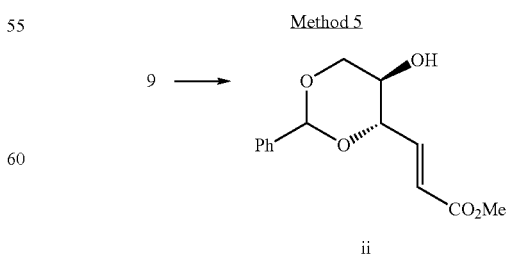

A solution of dimethoxyphosphoryl-acetic acid methyl ester (16.5 mL, 102 mmol) was added to a slurry of NaH (60% suspension in mineral oil, 4.07 g, 102 mmol) in THF (25 mL) at −20° C. After 30 min, a solution of aldehyde 9 (5.3 g, 25.5 mmol) in THF (25 mL) was added and stirring was continued for 30 min at −20° C. and 30 min at rt. The reaction was quenched by the addition of aq. NH$_4$Cl (50 mL). The aqueous layer was extracted with EtOAc (3×30 mL) followed by drying and concentration of the combined organic layers. The residue was purified by FC (silica gel, Hexanes/EtOAc 3:1 to 2:1) to afford ii (6.7 g, 99%). [α]$_D$=−49.7 (CHCl$_3$, c 0.82); $^1$H NMR (400 MHz, CDCl$_3$) δ 2.66 (d, 1H, J=11.2 Hz), 3.70 (m, 1H), 3.76 (s, 3H), 4.15 (dd, 1H, J=1.2, 12.0 Hz), 4.28 (dd, 1H, J=1.6, 12.0 Hz), 4.68 (ddd, 1H, J=1.6, 1.6, 3.6 Hz), 5.67 (s, 1H), 6.22 (dd, 1H, J=2.0, 15.6 Hz), 6.97 (dd, 1H, J=3.6, 15.6 Hz), 7.38-7.42 (m, 3H), 7.52-7.54 (m, 2H); $^{13}$C NMR (100 MHz, CDCl$_3$) δ 51.9, 65.6, 72.6, 78.7, 101.4, 122.7, 126.1, 128.5, 129.4, 137.5, 143.6, 166.6; IR: 3514, 1723, 1703, 1664, 1317, 1153, 1003; MS (ES) calc. for C$_{14}$H$_{17}$O$_5$ [MH]$^+$ 265.1, found 264.9.

Method 6

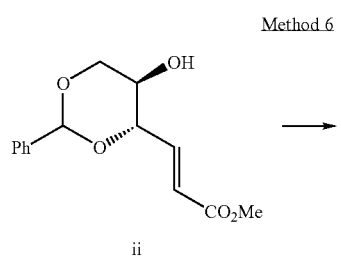

ii

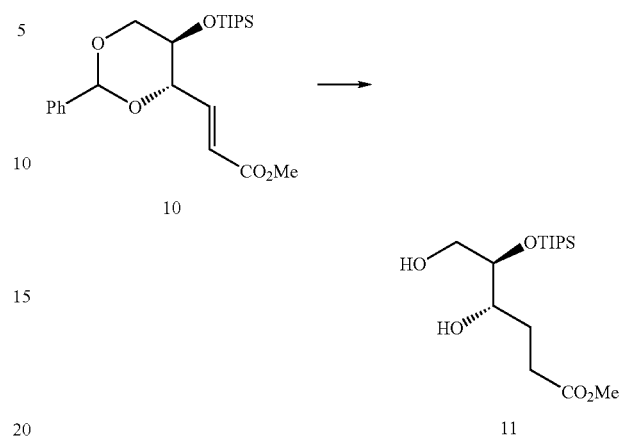

10

10% Pd/C (200 mg) catalyst was added to a solution of compound 10 (910 mg, 2.17 mmol) in EtOAc (20 mL) and hydrogenated (1 atm H$_2$) for 40 min. The catalyst was removed by filtration through a pad of silica gel and the filtrate was concentrated to give compound 11 (720 mg, 99%). [α]$_D$=+6.8 (CHCl$_3$, c 0.88); $^1$H NMR (400 MHz, CDCl$_3$) δ 1.06 (m, 21H), 1.76-1.93 (m, 2H), 2.43-2.57 (m, 2H), 2.62 (dd, 1H, J=5.2, 6.0 Hz), 2.78 (d, 1H, J=6.8 Hz), 3.66 (s, 3H), 3.64-3.76 (m, 3H), 3.82 (m, 1H); $^{13}$C NMR (100 MHz, CDCl$_3$) δ 12.5, 18.0, 18.0, 28.1, 30.8, 51.6, 63.8, 72.2, 74.3, 174.6; IR: 3436, 2945, 2868, 1741, 1464, 1119, 1067; MS (ES) calc. for C$_{16}$H$_{34}$O$_5$SiNa [MNa]$^+$ 357.2, found 357.1.

Method 8

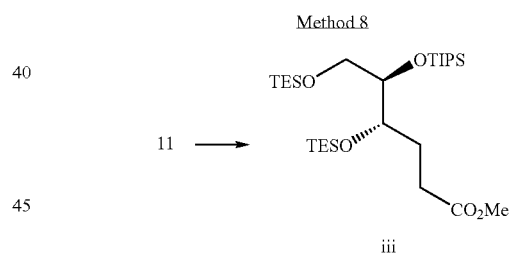

iii

10

To a solution of compound ii (600 mg, 2.27 mmol) in CH$_2$Cl$_2$ (20 mL) was added 2,6-lutidine (0.66 mL, 5.68 mmol) and TIPSOTf (1.22 mL, 4.55 mmol) at 0° C. under N$_2$. After stirring at 0° C. for 20 h, aq. NaHCO$_3$ was added followed by an extraction with ether. The combined organic extracts were washed with 1 N HCl and aq. NaHCO$_3$, dried and concentrated. The crude was purified by FC (silica gel, Hexanes/EtOAc 20:1) to give compound 10 (910 mg, 95%). [α]$_D$=−34.4 (CHCl$_3$, c 0.86); $^1$H NMR (400 MHz, CDCl$_3$) δ 1.08 (m, 21H), 3.73 (s, 3H), 3.91 (dd, 1H, J=1.6, 2.0 Hz), 4.07 (dd, 1H, J=1.6, 12.0 Hz), 4.23 (dd, 1H, J=2.0, 12.0 Hz), 4.56 (ddd, 1H, J=1.6, 2.0, 4.8 Hz), 5.60 (s, 1H), 6.16 (dd, 1H, J=1.6, 15.6 Hz), 7.00 (dd, 1H, J=4.8, 15.6 Hz), 7.35-7.40 (m, 3H), 7.52-7.54 (m, 2H); $^{13}$C NMR (100 MHz, CDCl$_3$) δ 12.7, 18.0, 18.1, 51.5, 66.7, 72.4, 79.2, 101.4, 122.0, 126.5, 128.3, 129.1, 138.3, 144.8, 166.5; IR: 2922, 1727, 1662, 1450, 1026; MS (ES) calc. for C$_{23}$H$_{36}$O$_5$SiNa [MNa]$^+$ 443.2, found 443.1.

Imidazole (718 mg, 10.55 mmol) and TESCl (1.42 mL, 8.46 mmol) were added to a solution of compound 11 (700 mg, 2.11 mmol) in DMF (8 mL) at rt. After stirring for 1 h, aq. NaHCO$_3$ was added and an extraction was performed with ether. The combined organic extracts were washed with water, dried and concentrated. The crude was purified by FC (silica gel, Hexanes/EtOAc 20:1) to give compound iii (1.10 g, 93%). [α]$_D$=+44.5 (CHCl$_3$, c 0.44); $^1$H NMR (400 MHz, CDCl$_3$) δ 0.59 (m, 12H), 0.95 (m, 18H), 1.06 (m, 21H), 1.53 (m, 1H), 2.05 (dddd, 1H, J=3.2, 6.4, 10.0, 13.6 Hz), 2.27 (ddd, 1H, J=6.4, 10.0, 16.0 Hz), 2.47 (ddd, 1H, J=5.2, 10.4, 16.0 Hz), 3.52 (dd, 1H, J=8.0, 10.0 Hz), 3.66 (s, 3H), 3.69 (ddd, 1H, J=3.2, 4.4, 10.0 Hz), 3.86 (m, 2H); $^{13}$C NMR (100 MHz, CDCl$_3$) δ 4.2, 5.1, 6.8, 6.9, 12.6, 18.1, 26.4, 31.3, 51.4, 63.6, 73.5, 77.2, 174.2; IR: 2955, 2877, 1745, 1462, 1242, 1131, 1104, 1088, 1005; MS (ES) calc. for C$_{28}$H$_{62}$O$_5$Si$_3$Na [MNa]$^+$ 585.4, found 585.4.

Method 9

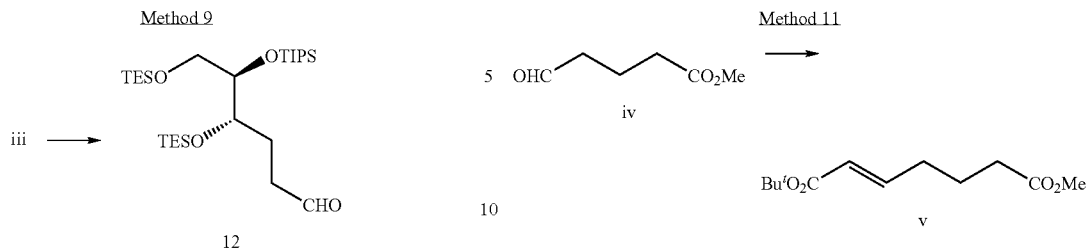

To a solution of iii (1.225 g, 2.18 mmol) in $CH_2Cl_2$ (30 mL) was added DIBAL-H (1.0 M in toluene, 2.6 ml, 2.6 mmol) at −78° C. under Ar. After 15 min, 0.3 ml of MeOH was added at −78° C., followed by the addition of aq. Na,K-tartrate (20 mL). The mixture was warmed to rt and stirred until the two layers separated. The aqueous layer was extracted with ethyl acetate. After drying and concentration of the combined organic layers, the obtained colorless oil was used directly for the next step without further purification. Spectral data of an analytical sample: $^1$H NMR (400 MHz, $CDCl_3$) δ 0.59 (m, 12H), 0.95 (m, 18H), 1.06 (m, 21H), 1.57 (m, 1H), 2.06 (m, 1H), 2.40 (m, 1H), 2.54 (m, 1H), 3.55 (dd, 1H, J=7.6, 10.4 Hz), 3.70 (ddd, 1H, J=3.2, 4.0, 9.6 Hz), 3.87 (m, 2H), 9.76 (t, 1H, J=1.6 Hz); $^{13}$C NMR (100 MHz, $CDCl_3$) δ 4.2, 5.0, 6.7, 6.8, 12.6, 18.1, 23.7, 41.4, 63.5, 73.7, 77.1, 202.6.

Method 10

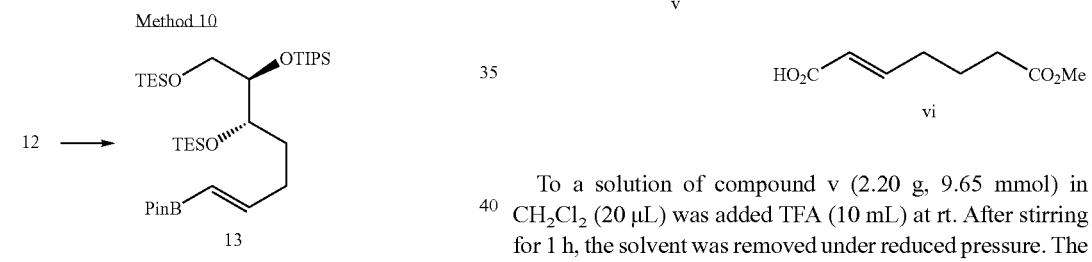

To a suspension of anhydrous $CrCl_2$ (3.75 g, 30.5 mmol) in THF (8 mL) at rt was added rapidly a solution of 12 (1.16 g, 2.18 mmol) and pinacol dichloromethylboronate (1.6 g, 7.58 mmol) in THF (60 mL), followed by the dropwise addition of a solution of anhydrous LiI (2.04 g, 1.52 mmol) in THF (30 mL). The reaction flask was then covered with foil to exclude light, and stirred vigorously for 20 h. The reaction mixture was dilute with hexanes (500 mL) and filtered through a pad of celite. The filtrate was washed with 10% aq. $Na_2S_2O_3$ and water, dried and concentrated. The residue was purified by FC (silica gel, Hexanes/EtOAc 10:1) to give compound 13 (1.2 g, 84% for two steps). $[α]_D$=+28.9 ($CHCl_3$, c 0.45); $^1$H NMR (400 MHz, $CDCl_3$) δ 0.58 (m, 12H), 0.94 (m, 18H), 1.06 (m, 21H), 1.26 (s, 12H), 1.29 (m, 1H), 1.85 (m, 1H), 2.06 (m, 1H), 2.31 (m, 1H), 3.47 (dd, 1H, J=8.0, 10.4 Hz), 3.64 (ddd, 1H, J=2.8, 4.0, 9.6 Hz), 3.83 (m, 2H), 5.44 (d, 1H, J=18.0 Hz), 6.65 (ddd, 1H, J=6.0, 6.4, 18.0 Hz); $^{13}$C NMR (100 MHz, $CDCl_3$) δ 4.2, 5.1, 6.8, 6.9, 12.6, 18.2, 24.7, 29.7, 33.2, 63.7, 74.1, 77.3, 82.9, 154.6; IR: 2955, 2876, 1639, 1461, 1363, 1320, 1239, 1145, 1101; MS (ES) calc. for $C_{34}H_{73}BO_5Si_3Na$ $[MNa]^+$679.5, found 679.4.

Method 11

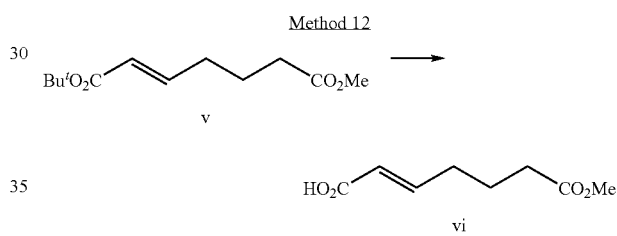

A solution of aldehyde iv (1.46 g, 11.23 mmol) and (tert-butoxycarbonylmethylene)triphenylphosphorane (5.50 g, 14.63 mmol) in benzene (25 mL) was refluxed for 12 h under $N_2$. After concentration, the residue was purified by FC (silica gel, Hexanes/EtOAc 10:1) to afford compound v (2.20 g, 86%) as a viscous oil. $^1$H NMR (300 MHz, $CDCl_3$) δ 1.44 (s, 9H), 1.77 (m, 2H), 2.20 (m, 2H), 2.32 (t, 2H, J=7.2 Hz), 3.65 (s, 3H), 5.73 (dt, 1H, J=1.5, 15.6 Hz), 6.79 (dt, 1H, J=6.9, 15.6 Hz); $^{13}$C NMR (75 MHz, $CDCl_3$) δ 23.2, 28.1, 31.2, 33.2, 51.5, 80.1, 123.8, 146.4, 165.8, 173.6; IR: 2979, 1740, 1714, 1654, 1438, 1368, 1163; MS (ES) calc. for $C_{12}H_{20}O_4Na$ $[MNa]^+$251.1; found 251.1.

Method 12

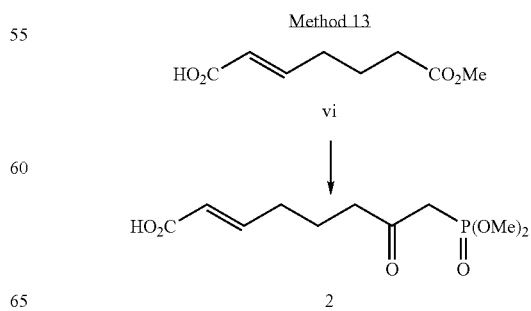

To a solution of compound v (2.20 g, 9.65 mmol) in $CH_2Cl_2$ (20 μL) was added TFA (10 mL) at rt. After stirring for 1 h, the solvent was removed under reduced pressure. The crude residue was azeotropically concentrated from benzene (3×50 mL) to yield a residue that was used without further purification. $^1$H NMR (300 MHz, $CDCl_3$) δ 1.83 (tt, 2H, J=7.2, 7.5 Hz), 2.30 (m, 2H), 2.38 (t, 2H, J=7.5 Hz), 3.70 (s, 3H), 5.86 (d, 1H, J=15.6 Hz), 7.09 (dt, 1H, J=6.9, 15.6 Hz), 10.81 (bs, 1H); $^{13}$C NMR (75 MHz, $CDCl_3$) δ 22.9, 31.5, 33.2, 52.0, 121.0, 151.8, 172.1, 174.4; IR: 3500-2500, 2954, 1737, 1697, 1653, 1438, 1422, 1287, 1212; MS (ES) calc. for $C_8H_{12}O_4Na$ $[MNa]^+$195.1, found 195.0.

Method 13

To a solution of dimethyl methylphosphonate (4.79 g, 38.60 mmol) in THF (30 mL) at −78° C. was added n-BuLi (2.5 M in hexanes, 15.4 mL, 38.50 mmol) to afford a white slurry. After stirring for 15 min, a solution of ester vi (1.90 g, 11.05 mmol) in THF (10 mL) was added dropwise. After stirring at −78° C. for 30 min and 0° C. for 1 h, 1 N HCl (50 mL) was added. The crude was extracted with EtOAc and the combined extracts were dried and concentrated. Excess dimethyl methylphosphonate was removed by distillation (100° C. oil bath, 2 mmHg) and the residue was purified by FC (silica gel, CH$_2$Cl$_2$/MeOH 50:1 to 20:1) to afford compound 2 (2.42 g, 95% from v) as a viscous oil. $^1$H NMR (300 MHz, CDCl$_3$) δ 1.73 (tt, 2H, J=7.5, 7.5 Hz), 2.20 (m, 2H), 2.62 (t, 2H, J=7.2 Hz), 3.09 (d, 2H, J$_{PH}$=23.1 Hz), 3.74 (s, 3H), 3.78 (s, 3H), 5.79 (dt, 1H, J=1.5, 15.9 Hz), 6.94 (dt, 1H, J=7.2, 15.9 Hz); $^{13}$C NMR (100 Hz, CDCl$_3$) δ 21.3, 31.0, 41.2 (d, J=129 Hz), 42.9, 53.2 (d, J=6.1 Hz), 121.7, 149.7, 170.3, 201.1 (d, J=7.7 Hz); IR: 3500-2500, 2959, 1713, 1655, 1402, 1232, 1033; MS (ES) calc. for C$_{10}$H$_{17}$O$_6$PNa [MNa]$^+$287.1, found 287.0.

Method 14

3
+
13

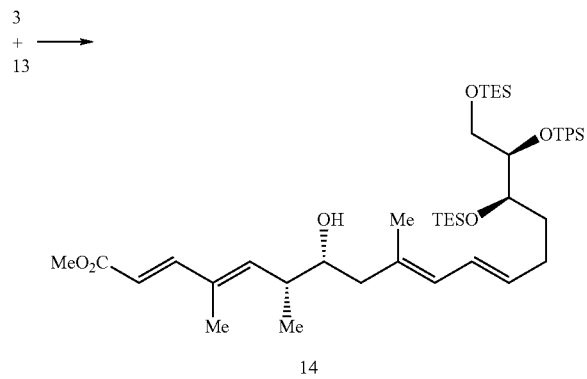

14

A mixture of 3 (271 mg, 0.74 mmol) and 13 (522 mg, 0.80 mmol) in THF (16 mL) and water (4 mL) was degassed by passing N$_2$ through the solution for 20 min. Pd(PPh$_3$)$_4$ (85.5 mg, 0.074 mmol) and Tl$_2$CO$_3$ (694 mg, 1.48 mmol) were added to the above solution to yield a green suspension that was stirred at rt for 5 hours. Aq. NH$_4$Cl was added to quench the reaction. The aqueous layer was extracted with ethyl acetate and the combined organic layers were dried and concentrated to yield a residue that was purified by FC (silica gel, Hexanes/EtOAc 8:1). Compound 14 (448 mg, 79%) was obtained as a colorless oil. $^1$H NMR (400 MHz, CDCl$_3$) δ 0.59 (m, 12H), 0.95 (m, 18H), 1.06-1.10 (m, 24H), 1.26 (m, 1H), 1.71 (m, 1H), 1.74 (s, 3H), 1.81 (s, 3H), 1.97 (dd, 1H, J=10.0, 13.2 Hz), 2.03 (m, 1H), 2.25 (m, 2H), 2.61 (m, 1H), 3.48 (dd, 1H, J=8.0, 10.0 Hz), 3.55 (m, 1H), 3.67 (m, 1H), 3.75 (s, 3H), 3.84 (m, 2H), 5.63 (ddd, 1H, J=6.8, 7.6, 15.2 Hz), 5.77 (d, 1H, J=10.0 Hz), 5.83 (d, 1H, J=16.0 Hz), 5.86 (d, 1H, J=10.4 Hz), 6.24 (dd, 1H, J=10.8, 14.8 Hz), 7.34 (d, 1H, J=15.6 Hz); $^{13}$C NMR (100 MHz, CDCl$_3$) δ 4.2, 5.1, 6.8, 6.9, 12.6, 16.1, 16.4, 18.2, 30.1, 30.8, 39.4, 45.8, 51.5, 63.6, 72.3, 73.9, 77.2, 115.8, 126.2, 128.5, 132.1, 132.7, 134.0, 144.0, 149.7, 167.9; IR: 3583, 2943, 1679, 1445, 1377, 1040.

Method 15

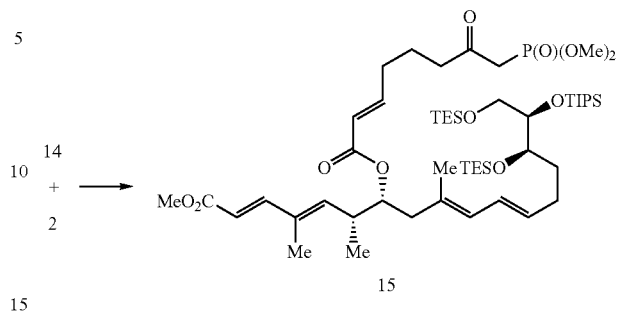

14
+
2

15

A mixture of compound 2 (160 mg, 0.61 mmol), 2,4,6-trichlorobenzoyl chloride (95 μL, 0.61 mmol) and Et$_3$N (168 μL, 1.22 mmol) in toluene (5.0 mL) was stirred at rt for 2 h to give solution A. To a solution of compound 14 (88 mg, 0.12 mmol) and DMAP (70 mg, 0.58 mmol) in toluene (4 mL) was added solution A (1.0 mL, ~1 eq.) at rt After stirring for 30 min, another portion of solution A (0.8 mL) was added. After stirring for 30 min at rt, aq. NaHCO$_3$ was added and the mixture was extracted with EtOAc. The combined extracts were washed with water, 1 N HCl and aq. NaHCO$_3$. The combined organic layers were dried and concentrated to afford a residue that was purified by FC (silica gel, Hexanes/EtOAc 1:2 to CH$_2$Cl$_2$/MeOH 20:1 to 10:1) to give compound 15 (81 mg, 69%). [α]$_D$=+29.7 (CH$_2$Cl$_2$, c 0.18); $^1$H NMR (CDCl$_3$) δ0.58 (m, 12H), 0.94 (m, 18H), 1.02 (d, 3H, J=6.8 Hz), 1.04-1.07 (m, 21H), 1.24 (m, 1H), 1.73 (s, 3H), 1.76 (m, 3H), 1.76 (s, 3H), 1.98 (m, 1H), 2.19-2.31 (m, 5H), 2.66 (t, 2H, J=7.2 Hz), 2.81 (m, 1H), 3.09 (d, 2H, J$_{PH}$=22.8 Hz), 3.47 (dd, 1H, J=8.0, 10.4 Hz), 3.65 (m, 1H), 3.75 (s, 3H), 3.78 (s, 3H), 3.81 (s, 3H), 3.83 (m, 2H), 5.02 (m, 1H), 5.55 (ddd, 1H, J=7.6, 7.6, 14.8 Hz), 5.72 (d, 1H, J=9.2 Hz), 5.77 (d, 1H, J=8.8 Hz), 5.80 (d, 1H, J=15.6 Hz), 5.82 (d, 1H, J=15.6 Hz), 6.18 (dd, 1H, J=10.8, 15.2 Hz), 6.89 (ddd, 1H, J=6.8, 6.8, 15.6 Hz), 7.31 (d, 1H, J=15.6 Hz); $^{13}$C NMR (100 MHz, CDCl$_3$) δ 4.2, 5.0, 6.7, 6.9, 12.5, 12.5, 15.7, 16.6, 18.1, 21.5, 30.2, 30.8, 31.0, 36.6, 40.7, 41.6 (d, J=128 Hz), 42.2, 43.0, 51.4, 53.0 (d, J=6.1 Hz), 63.6, 74.0, 74.9, 77.2, 116.1, 121.8, 126.4, 128.0, 131.3, 133.0, 133.2, 142.7, 148.1, 149.5, 165.9, 167.7, 201.1 (d, J=6.0 Hz); IR: 2927, 1717, 1664, 1629, 1453, 1036; MS (ES) calc. for C$_{52}$H$_{97}$O$_{11}$PSi$_3$Na [MNa]$^+$1035.6; found 1035.7.

Method 16

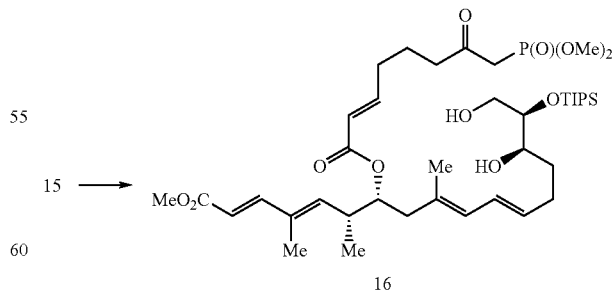

15

16

To a solution compound 15 (130 mg, 0.13 mmol) in CH$_2$Cl$_2$/MeOH (5 mL, 3/1) was added PPTS (4×130 mg, 4×0.52 mmol) every 30 min at 0° C. After the reaction was completed (2 h), NaHCO$_3$ (1 g) was added and the mixture was stirred at room temperature for 10 min. The precipitate was filtered and the filtrate was concentrated. The crude obtained was purified by FC (silica gel, CH$_2$Cl$_2$/MeOH 50:1 to 20:1) to give compound 16 (95 mg, 95%). $^1$H NMR (400 MHz, CDCl$_3$) δ 1.02 (d, 3H, J=6.8 Hz), 1.04-1.11 (m, 21H), 1.60 (m, 2H), 1.72 (s, 3H), 1.76 (m, 2H), 1.77 (s, 3H), 2.17-2.38 (m, 6H), 2.65 (t, 2H, J=7.0 Hz), 2.81 (m, 1H), 3.09 (d, 2H, J$_{PH}$=22.5 Hz), 3.65-3.82 (m, 4H), 3.76 (s, 3H), 3.78 (s, 3H), 3.80 (s, 3H), 5.01 (m, 1H), 5.58 (ddd, 1H, J=6.8, 7.6, 15.2 Hz), 5.72 (d, 1H, J=8.8 Hz), 5.74 (d, 1H, J=9.2 Hz), 5.79 (d, 1H, J=15.6 Hz), 5.83 (d, 1H, J=15.6 Hz), 6.21 (dd, 1H, J=10.8, 15.2 Hz), 6.88 (ddd, 1H, J=6.8, 6.8, 16.0 Hz), 7.31 (d, 1H, J=16.0 Hz); $^{13}$C NMR (75 MHz, CDCl$_3$) δ 12.5, 12.5, 15.9, 16.6, 18.0, 18.0, 21.5, 29.2, 31.0, 32.8, 36.9, 41.4 (J=128 Hz), 42.4, 43.0, 51.4, 53.0 (d, J=5.5 Hz), 63.9, 72.0, 74.6, 74.8, 116.1, 121.7, 126.7, 128.0, 131.6, 132.5, 133.0, 142.5, 148.1, 149.4, 165.9, 167.7, 201.1 (d, J=8.1 Hz); IR: 3403, 2926, 1717, 1624, 1459, 1261, 1033; MS (ES) calc. for C$_{40}$H$_{70}$O$_{11}$PSi [MH]$^+$ 785.4; found 785.3.

Method 17

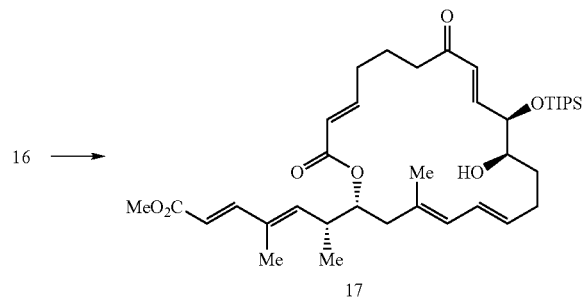

16 →

17

IPh(OAc)$_2$ (322 mg, 1.00 mmol) and TEMPO (1-oxyl-2,2,6,6-tetramethylpiperidine, 16 mg, 0.10 mmol) were dissolved in CH$_2$Cl$_2$ (3 mL, containing 0.1% water) to give a pink solution A. Compound 16 (95 mg, 0.12 mmol) was dissolved in CH$_2$Cl$_2$ (15 mL) and solution A (400 µL, 0.13 mmol) was added. After stirring at rt for 1 h, solution A (400 µL, 0.13 mmol) was added again. The reaction was completed after stirring for another 1 h. 10% Na$_2$S$_2$O$_3$ was added and the product was extracted with CH$_2$Cl$_2$. The combined extracts were washed with NaHCO$_3$ solution and water. After drying with Na$_2$SO$_4$, the solvent was removed and the crude aldehyde thus obtained was used in the next step without further purification.

A mixture of grounded K$_2$CO$_3$ (900 mg, 6.52 mmol), 18-crown-6 (1.16 g, 4.39 mmol) in toluene (160 mL) was heated at 60° C. for 1 h and cooled down. A solution of the crude aldehyde obtained above in toluene (20 mL) was added. After the reaction mixture was heated at 60° C. for another 1 h, it was filtered through a pad of silica gel. Elution with Hexanes/EtOAc (4:1, 200 mL) and concentration of the combined filtrates provided a residue that was purified by FC (silica gel, Hexanes/EtOAc 6:1 to 4:1) to give compound 17 (55 mg, 70% from 16). [α]$_D$=−48.9 (CH$_2$Cl$_2$, c 0.23); $^1$H NMR (400 MHz, CDCl$_3$) δ 1.02 (d, 3H, J=6.8 Hz), 1.04-1.11 (m, 21H), 1.31 (m, 1H), 1.45 (m, 1H), 1.70 (s, 3H), 1.72 (m, 1H), 1.79 (d, 3H, J=0.8 Hz), 1.81 (m, 1H), 2.08-2.25 (m, 4H), 2.29 (m, 1H), 2.45 (ddd, 1H, J=6.0, 8.4, 14.8 Hz), 2.56-2.64 (m, 2H), 2.82 (m, 1H), 3.42 (m, 1H), 3.76 (s, 3H), 4.11 (m, 1H), 5.04 (ddd, 1H, J=7.2, 7.2 Hz), 5.04 (ddd, 1H, J=2.0, 10.8 Hz), 5.40 (ddd, 1H, J=4.8, 9.6, 14.8 Hz), 5.69 (d, 1H, J=10.8 Hz), 5.71 (d, 1H, J=10.8 Hz), 5.75 (d, 1H, J=15.6 Hz), 5.83 (d, 1H, J=15.6 Hz), 6.14 (d, 1H, J=16.0 Hz), 6.15 (d, 1H, J=10.8, 14.8 Hz), 6.60 (dd, 1H, J=7.2, 16.0 Hz), 6.82 (ddd, 1H, J=6.8, 7.6, 15.6 Hz), 7.32 (d, 1H, J=16.0 Hz); $^{13}$C NMR (100 MHz, CDCl$_3$) δ 12.3, 12.6, 16.2, 16.6, 17.9, 18.0, 23.1, 28.9, 31.2, 32.7, 37.9, 38.9, 43.0, 51.5, 73.4, 73.9, 77.0, 116.3, 122.0, 127.5, 128.1, 130.7, 131.6, 132.2, 133.4, 142.1, 145.9, 148.0, 149.4, 165.9, 167.7, 200.0; IR: 3403, 2943, 1719, 1626, 1438, 1169, 1070, 1018; MS (ES) calc. for C$_{38}$H$_{60}$O$_7$SiNa [MNa]$^+$ 679.4; found 679.3.

Method 18

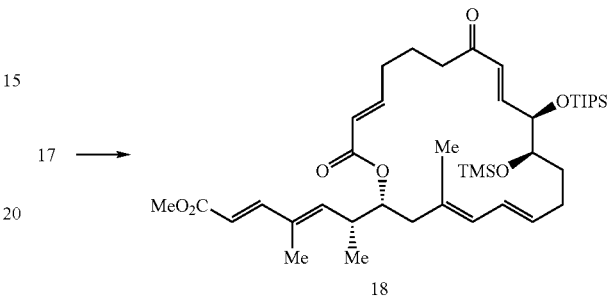

17 →

18

To a solution of compound 17 (50 mg, 0.076 mmol) in CH$_2$Cl$_2$ (3 mL) was added Et$_3$N (64 µL, 0.45 mmol), TMSCl (29 µL, 0.23 mmol) and DMAP (2 mg) at 0° C. After the mixture was stirred at rt for 1 h, NaHCO$_3$ solution was added. The mixture was extracted with CH$_2$Cl$_2$ and the combined extracts were dried and concentrated. The crude obtained was purified by FC (silica gel, Hexanes/EtOAc 10:1) to give compound 18 (52 mg, 91%). [α]$_D$=+37.1 (CH$_2$Cl$_2$, c 0.7); $^1$H NMR (400 MHz, CDCl$_3$) δ 0.14 (s, 9H), 1.02 (d, 3H, J=6.8 Hz), 1.06-1.10 (m, 21H), 1.26 (m, 1H), 1.55 (m, 1H), 1.68 (s, 3H), 1.73 (m, 1H), 1.80 (m, 1H), 1.80 (d, 3H, J=1.2 Hz), 1.95 (m, 1H), 2.05-2.22 (m, 5H), 2.44 (ddd, 1H, J=7.2, 7.6, 14.8 Hz), 2.59 (ddd, 1H, J=6.8, 7.6, 14.4 Hz), 2.80 (m, 1H), 3.74 (m, 1H), 3.76 (s, 3H), 4.45 (m, 1H), 4.98 (ddd, 1H, J=2.4, 7.6, 10.4 Hz), 5.48 (ddd, 1H, J=5.6, 9.2, 14.8 Hz), 5.63 (d, 1H, J=10.8 Hz), 5.72 (d, 1H, J=8.8 Hz), 5.74 (d, 1H, J=15.6 Hz), 5.84 (d, 1H, J=16.0 Hz), 6.05 (dd, 1H, J=10.8, 15.2 Hz), 6.49 (dd, 1H, J=2.0, 16.0 Hz), 6.80 (ddd, 1H, J=6.8, 7.2, 16.0 Hz), 6.94 (dd, 1H, J=3.2, 16.0 Hz), 7.32 (d, 1H, J=15.6 Hz); $^{13}$C NMR (75 MHz, CDCl$_3$) δ 0.4, 12.2, 12.6, 16.4, 16.7, 18.0, 23.8, 29.0, 31.3, 32.6, 37.9, 41.4, 43.3, 51.5, 74.0, 74.9, 75.2, 116.2, 121.5, 126.1, 128.1, 128.8, 130.7, 133.3, 133.8, 142.3, 146.5, 147.8, 149.4, 166.1, 167.8, 200.3; IR: 2947, 1721, 1628, 1437, 1167, 1021; MS (ES) calc. for C$_{41}$H$_{68}$O$_7$Si$_2$Na [MNa]$^+$ 751.5; found 751.3.

Method 19

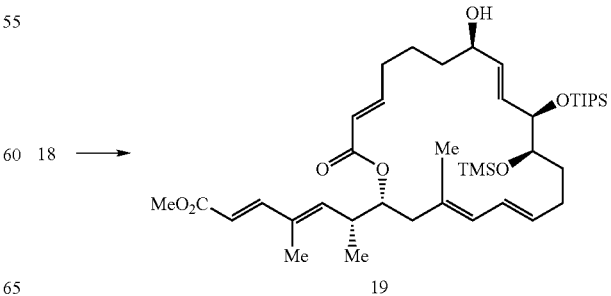

18 →

19

(S)-(−)-2-Methyl-CBS-oxazaborolidine (1.0 M in toluene, 102 μL, 0.10 mmol) was added to the solution of compound 18 (25 mg, 0.034 mmol) in THF (3 mL) at −40° C. After the mixture was stirred for 10 min, BH$_3$-THF (1.0 M in THF, 68 μL, 0.068 mmol) was added dropwise and stirred at −40° C. for 40 min. MeOH (0.1 mL in 5 mL ether) was added followed by aq. NaHCO$_3$. The mixture was extracted with CH$_2$Cl$_2$ and the combined extracts were dried and concentrated. The crude obtained was purified by FC (silica gel, CH$_2$Cl$_2$/EtOAc 20:1) to give compound 19 and its epimer C7-epi-19 (25 mg, 100%) in a ratio of ~4:1. These two isomers were further separated by HPLC (silica gel, CH$_2$Cl$_2$/EtOAc 20:1). Compound 19: [α]$_D$=+30.9 (CH$_2$Cl$_2$, c 0.5); $^1$H NMR (400 MHz, CDCl$_3$) δ 0.13 (s, 9H), 1.02 (d, 3H, J=6.8 Hz), 1.07-1.10 (m, 21H), 1.24-1.39 (m, 3H), 1.46-1.60 (m, 3H), 1.64 (m, 1H), 1.68 (s, 3H), 1.80 (d, 3H, J=0.8 Hz), 1.93 (m, 1H), 2.05-2.19 (m, 5H), 2.80 (m, 1H), 3.63 (ddd, 1H, J=2.4, 4.4, 9.2 Hz), 3.76 (s, 3H), 4.18 (m, 1H), 4.29 (m, 1H), 4.97 (ddd, 1H, J=2.4, 8.0, 10.4 Hz), 5.46 (ddd, 1H, J=5.6, 9.2, 14.8 Hz), 5.64 (d, 1H, J=9.2 Hz), 5.63-5.78 (m, 4H), 5.84 (d, 1H, J=15.6 Hz), 6.07 (dd, 1H, J=10.8, 15.2 Hz), 6.82 (ddd, 1H, J=7.6, 7.6, 15.6 Hz), 7.32 (d, 1H, J=16.0 Hz); $^{13}$C NMR (75 MHz, CDCl$_3$) δ 0.5, 12.4, 12.6, 16.6, 16.8, 18.1, 24.0, 29.3, 32.5, 32.9, 37.1, 37.8, 43.0, 51.5, 72.9, 74.0, 74.7, 75.4, 116.2, 121.2, 126.1, 128.6, 130.6, 131.8, 132.8, 133.3, 133.8, 142.5, 148.7, 149.4, 166.2, 167.8; IR: 3465, 2945, 1720, 1624, 1251, 1168; MS (ES) calc. for C$_{41}$H$_{70}$O$_7$Si$_2$Na [MNa]$^+$753.5; found 753.3.

C7-epi-19: [α]$_D$=+7.1 (CH$_2$Cl$_2$, c 0.85); $^1$H NMR (400 MHz, CDCl$_3$) δ 0.13 (s, 9H), 1.02 (d, 3H, J=6.8 Hz), 1.04-1.13 (m, 21H), 1.20-1.63 (m, 7H), 1.68 (s, 3H), 1.80 (d, 3H, J=0.8 Hz), 1.96-2.26 (m, 6H), 2.79 (m, 1H), 3.60 (ddd, 1H, J=2.4, 5.2, 8.4 Hz), 3.76 (s, 3H), 4.11-4.19 (m, 2H), 4.98 (ddd, 1H, J=2.4, 7.6, 10.4 Hz), 5.29 (ddd, 1H, J=5.2, 9.2, 14.8 Hz), 5.63-5.75 (m, 5H), 5.84 (d, 1H, J=15.6 Hz), 6.06 (dd, 1H, J=10.8, 15.2 Hz), 6.82 (ddd, 1H, J=5.6, 9.2, 15.2 Hz), 7.32 (d, 1H, J=16.0 Hz); $^{13}$C NMR (100 MHz, CDCl$_3$) δ 0.6, 12.5, 12.6, 16.5, 16.7, 18.1, 18.2, 23.9, 29.7, 32.4, 32.8, 37.2, 37.9, 43.4, 51.5, 72.5, 73.9, 76.2, 76.4, 116.2, 121.2, 126.0, 128.6, 130.4, 130.7, 133.3, 133.8, 142.5, 148.9, 149.4, 166.2, 167.8; IR ν$_{max}$ 3495, 2946, 1722, 1624, 1250, 1170 cm$^{-1}$.

(R)-MTPA ester of 19: $^1$H NMR (400 MHz, CDCl$_3$) δ 0.13 (s, 9H), 1.02 (d, 3H, J=6.8 Hz), 1.06 (m, 21H), 1.29-1.32 (m, 2H), 1.49 (m, 1H), 1.63 (m, 1H), 1.67 (s, 3H), 1.70 (m, 1H), 1.80 (d, 3H, J=0.8 Hz), 1.91 (m, 2H), 2.04-2.19 (m, 5H), 2.80 (m, 1H), 3.54 (s, 3H), 3.64 (ddd, 1H, J=2.4, 4.4, 9.2 Hz), 3.76 (s, 3H), 4.35 (ddd, 1H, J=1.6, 2.0, 4.4 Hz), 4.96 (ddd, 1H, J=2.4, 8.0, 10.4 Hz), 5.44 (ddd, 1H, J=5.6, 9.2, 14.8 Hz), 5.52 (ddd, 1H, J=6.4, 8.0, 8.4 Hz), 5.63 (d, 1H, J=10.8 Hz), 5.70 (d, 1H, J=15.6 Hz), 5.71 (d, 1H, J=10.8 Hz), 5.76 (ddd, 1H, J=2.0, 8.8, 15.2 Hz), 5.84 (d, 1H, J=15.6 Hz), 6.02 (dd, 1H, J=2.8, 15.2 Hz), 6.06 (dd, 1H, J=10.8, 15.2 Hz), 6.74 (ddd, 1H, J=6.4, 8.4, 14.8 Hz), 7.32 (d, 1H, J=16.0 Hz), 7.39 (m, 3H), 7.52 (m, 2H).

(S)-MTPA ester of 19: $^1$H NMR (400 MHz, CDCl$_3$) δ 0.13 (s, 9H), 1.00 (d, 3H, J=6.8 Hz), 1.03 (m, 21H), 1.32-1.36 (m, 2H), 1.50 (m, 1H), 1.68 (s, 3H), 1.69 (m, 1H), 1.75 (m, 1H), 1.80 (d, 3H, J=0.8 Hz), 1.90 (m, 2H), 2.06-2.20 (m, 5H), 2.81 (m, 1H), 3.50 (s, 3H), 3.62 (ddd, 1H, J=2.0, 4.4, 9.2 Hz), 3.76 (s, 3H), 4.32 (ddd, 1H, J=2.4, 2.4, 4.4 Hz), 4.96 (ddd, 1H, J=2.4, 8.0, 10.4 Hz), 5.44 (ddd, 1H, J=5.6, 9.2, 14.8 Hz), 5.53 (ddd, 1H, J=5.6, 8.4, 8.4 Hz), 5.63 (d, 1H, J=10.8 Hz), 5.72 (d, 1H, J=10.4 Hz), 5.73 (d, 1H, J=15.6 Hz), 5.73 (ddd, 1H, J=2.0, 8.8, 15.2 Hz), 5.84 (d, 1H, J=15.6 Hz), 6.00 (dd, 1H, J=2.8, 15.6 Hz), 6.07 (dd, 1H, J=10.8, 15.2 Hz), 6.78 (ddd, 1H, J=6.0, 8.0, 14.8 Hz), 7.33 (d, 1H, J=15.6 Hz), 7.39 (m, 3H), 7.52 (m, 2H).

Method 20

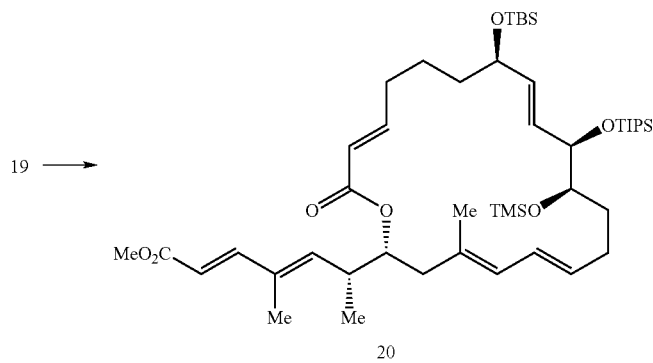

19 →

20

| | H-2 | H-3 | H-4 | H-5 | H-6a | H-6b | H-8 | H-9 | H-10 | H-11 |
|---|---|---|---|---|---|---|---|---|---|---|
| (R)-MTPA ester | 5.703 | 6.744 | 2.120 | 1.288~1.322 | 1.704 | 1.630 | 5.755 | 6.023 | 4.348 | 3.637 |
| (S)-MTPA ester | 5.726 | 6.783 | 2.130 | 1.320~1.360 | 1.752 | 1.694 | 5.728 | 6.002 | 4.320 | 3.624 |
| δ$_R$-δ$_S$ (ppm) | −0.023 | −0.039 | −0.010 | −0.032~−0.038 | −0.048 | −0.064 | +0.027 | +0.021 | +0.028 | +0.013 |

To a solution of compound 19 (23 mg, 0.032 mmol) in $CH_2Cl_2$ (5 mL) was added 2,6-lutidine (22 μL, 0.19 mmol) and TBSOTf (22 μL, 0.096 mmol) at −78° C. After the mixture was stirred for 30 min, aq. $NaHCO_3$ was added and the mixture was warmed to rt. After stirring for 5 min, the mixture was extracted with $CH_2Cl_2$. The combined extracts was dried and concentrated. The crude obtained was purified by FC (silica gel, hexanes/EtOAc 20:1) to give compound 20 (25 mg, 94%). $[α]_D$=+10.7 ($CH_2Cl_2$, c 0.50); $^1$H NMR (400 MHz, $CDCl_3$) δ 0.00 (s, 3H), 0.04 (s, 3H), 0.13 (s, 9H), 0.88 (s, 9H), 1.02 (d, 3H, J=6.8 Hz), 1.06-1.10 (m, 21H), 1.22-1.38 (m, 3H), 1.46-1.58 (m, 3H), 1.68 (s, 3H), 1.80 (d, 3H, J=0.8 Hz), 1.96 (m, 1H), 2.04-2.18 (m, 5H), 2.80 (m, 1H), 3.61 (ddd, 1H, J=2.8, 4.4, 9.2 Hz), 3.76 (s, 3H), 4.21 (dd, 1H, J=6.0, 11.6 Hz), 4.26 (dd, 1H, J=3.6, 3.6 Hz), 4.97 (ddd, 1H, J=2.4, 7.6, 10.4 Hz), 5.48 (ddd, 1H, J=5.6, 9.2, 14.8 Hz), 5.57-5.73 (m, 5H), 5.83 (d, 1H, J=16.0 Hz), 6.07 (dd, 1H, J=10.8, 14.8 Hz), 6.83 (ddd, 1H, J=6.4, 8.0, 14.8 Hz), 7.33 (d, 1H, J=15.6 Hz); $^{13}$C NMR (75 MHz, $CDCl_3$) δ −4.8, −4.6, 0.5, 12.5, 12.6, 16.5, 16.8, 18.2, 23.4, 25.8, 29.6, 32.4, 33.1, 37.9, 38.6, 43.1, 51.5, 73.0, 73.9, 74.9, 75.9, 116.2, 121.0, 126.1, 128.8 (2×C), 130.5, 133.3, 133.9, 133.9, 142.5, 149.2, 149.5, 166.2, 167.8; IR: 2947, 2865, 1722, 1625, 1462, 1253, 1168; MS (ES) calc. for $C_{41}H_{70}O_7Si_2Na$ [M—$C_6H_{14}Si$+Na]$^+$753.5, found 753.4.

Method 21

20 ⟶

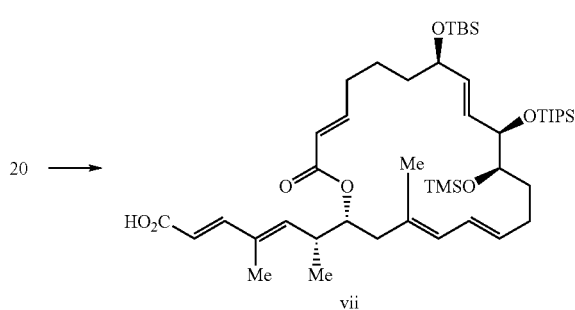

vii $(Bu_3Sn)_2O$ (150 μL, 0.30 mmol) was added to a solution of compound 20 (25 mg, 0.030 mmol) in toluene (0.5 mL). After the mixture was heated at 80° C. for 36 h, it was directly purified by FC (silica gel, $CH_2Cl_2$/EtOAc 2:1) to give acid vii (20 mg, 81%). $[α]_D$=+16.5 ($CH_2Cl_2$, c 0.41); $^1$H NMR (400 MHz, $CDCl_3$) δ 0.01 (s, 3H), 0.04 (s, 3H), 0.13 (s, 9H), 0.88 (s, 9H), 1.03 (d, 3H, J=6.4 Hz), 1.06-1.10 (m, 21H), 1.22-1.42 (m, 3H), 1.46-1.60 (m, 3H), 1.68 (s, 3H), 1.82 (s, 3H), 1.96 (m, 1H), 2.06-2.20 (m, 5H), 2.82 (m, 1H), 3.61 (ddd, 1H, J=2.8, 4.4, 9.2 Hz), 4.20 (dd, 1H, J=6.0, 11.6 Hz), 4.26 (dd, 1H, J=3.2, 3.6 Hz), 4.98 (ddd, 1H, J=2.4, 8.0, 10.8 Hz), 5.48 (ddd, 1H, J=5.6, 9.2, 14.8 Hz), 5.57-5.68 (m, 3H), 5.71 (d, 1H, J=15.6 Hz), 5.77 (d, 1H, J=10.0 Hz), 5.84 (d, 1H, J=15.6 Hz), 6.07 (dd, 1H, J=10.8, 15.2 Hz), 6.83 (ddd, 1H, J=6.4, 8.0, 14.8 Hz), 7.39 (d, 1H, J=16.0 Hz); $^{13}$C NMR (75 MHz, $CDCl_3$) δ −4.8, −4.6, 0.5, 12.5, 12.6, 16.5, 16.7, 18.2, 23.4, 25.8, 29.6, 29.7, 32.4, 33.1, 37.9, 38.6, 43.1, 73.0, 73.9, 74.9, 75.9, 116.0, 120.9, 126.1, 128.8 (2×C), 130.4, 133.3, 133.9 (2×C), 142.5, 149.2, 151.3, 166.2, 172.4; IR: 3584-2500, 2945, 1721, 1689, 1620, 1463, 1252, 1098.

Method 22 vii ⟶

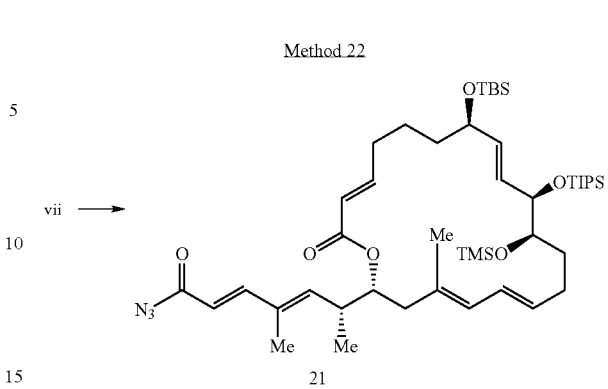

21

$Et_3N$ (66 μL, 0.47 mmol) and DPPA (22 μL, 0.10 mmol) was added to a solution of acid vii (20 mg, 0.024 mmol) in benzene (5 mL) at rt. After stirring for 5 h, the mixture was directly purified by FC (silica gel, hexanes/EtOAc 20:1) to give azide 21 (19 mg, 92%). $[α]_D$=+45.3 ($CH_2Cl_2$, c 0.33); $^1$H NMR (400 MHz, $CDCl_3$) δ 0.00 (s, 3H), 0.04 (s, 3H), 0.13 (s, 9H), 0.87 (s, 9H), 1.03 (d, 3H, J=6.8 Hz), 1.06-1.10 (m, 21H), 1.22-1.42 (m, 3H), 1.46-1.60 (m, 3H), 1.68 (s, 3H), 1.80 (d, 3H, J=0.8 Hz), 1.96 (m, 1H), 2.06-2.20 (m, 5H), 2.82 (m, 1H), 3.61 (ddd, 1H, J=2.8, 4.4, 8.8 Hz), 4.20 (dd, 1H, J=6.0, 11.6 Hz), 4.26 (dd, 1H, J=3.6, 3.6 Hz), 4.98 (ddd, 1H, J=2.8, 7.6, 10.4 Hz), 5.48 (ddd, 1H, J=5.2, 8.8, 14.8 Hz), 5.57-5.68 (m, 3H), 5.71 (d, 1H, J=15.6 Hz), 5.82 (d, 1H, J=15.2 Hz), 5.82 (d, 1H, J=12.0 Hz), 6.06 (dd, 1H, J=10.8, 14.8 Hz), 6.83 (ddd, 1H, J=6.4, 8.0, 14.8 Hz), 7.37 (d, 1H, J=15.2 Hz); $^{13}$C NMR (100 MHz, $CDCl_3$) δ −4.8, −4.6, 0.5, 12.5, 12.6, 16.6, 16.6, 18.2, 23.4, 25.8, 29.6, 32.4, 33.1, 38.0, 38.6, 43.1, 73.0, 73.7, 74.9, 75.9, 117.7, 120.9, 126.0, 128.8, 128.9, 130.3, 133.4, 133.9, 134.0, 145.1, 149.3, 151.4, 166.2, 172.3; IR: 2946, 2866, 2139, 1722, 1689, 1612, 1251.

Method 23

21 ⟶

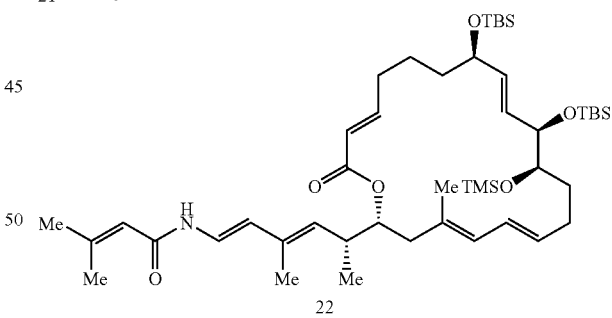

22

A solution of azide 21 (19 mg, 0.022 mmol) in benzene (5 mL) was refluxed for 4.5 h and the solvent was removed with a steady stream of $N_2$. The residue was dissolved in THF (4 mL) and added dropwise to a solution of 2-methyl-1-propenylmagnesium bromide (0.5 M in THF, 400 μL, 0.20 mmol) in THF (1 mL) at −78° C. over 20 min. After stirring for 30 min, ether (cooled to −78° C., 15 mL) was added followed by aq. $NH_4Cl$ (2 mL). The mixture was extracted with EtOAc and the combined extracts were dried and concentrated. The residue was purified by FC [silica gel (washed with 0.5% $Et_3N$ in hexanes), Hexanes/EtOAc 6:1] to give compound 22 (15 mg, 76%). $[α]_D$=−10.7 (EtOAc, c 0.26); $^1$H NMR (400

MHz, C$_6$D$_6$) δ 0.09 (s, 3H), 0.13 (s, 3H), 0.20 (s, 9H), 1.01 (s, 9H), 1.11 (d, 3H, J=6.4 Hz), 1.18 (m, 21H), 1.22-1.55 (m, 4H), 1.51 (s, 3H), 1.61 (s, 3H), 1.76 (s, 3H), 1.86-1.92 (m, 4H), 2.01 (m, 2H), 2.30-2.40 (m, 2H), 2.25 (s, 3H), 2.75 (m, 1H), 3.87 (m, 1H), 4.17 (dd, 1H, J=6.0, 11.2 Hz), 4.51 (dd, 1H, J=3.6, 4.0 Hz), 5.08 (bs, 1H), 5.21 (d, 1H, J=10.0 Hz), 5.28 (ddd, 1H, J=2.4, 8.4, 10.8 Hz), 5.60 (d, 1H, J=14.8 Hz), 5.73 (ddd, 1H, J=5.6, 8.4, 14.8 Hz), 5.84 (ddd, 1H, J=0.8, 6.4, 15.6 Hz), 5.90 (d, 1H, J=15.6 Hz), 5.96 (dd, 1H, J=4.4, 15.6 Hz), 5.98 (d, 1H, J=10.4 Hz), 6.34 (dd, 1H, J=10.8, 15.2 Hz), 6.53 (d, 1H, J=10.8 Hz), 7.02 (ddd, 1H, J=6.8, 8.0, 14.8 Hz), 7.41 (dd, 1H, J=11.2, 14.8 Hz); $^{13}$C NMR (100 MHz, C$_6$D$_6$) δ −4.2, −4.0, 1.1, 13.3, 13.4, 17.2, 18.1, 18.8, 20.4, 24.2, 26.4, 27.5, 30.6, 33.5, 33.6, 37.2, 38.3, 39.2, 44.5, 73.7, 75.1, 76.4, 77.0, 117.4, 118.6, 122.3, 122.7, 127.5, 129.5, 129.9, 131.0, 132.1, 133.9, 133.9, 134.9, 149.0, 153.6, 163.4, 166.5; IR: 3348, 2930, 1721, 1642, 1516, 1464, 1252, 1070; MS (ES) calc. for C$_{50}$H$_{88}$NO$_6$Si$_3$ [M-1]$^-$ 882.6; found 882.3.

Method 24

22 →

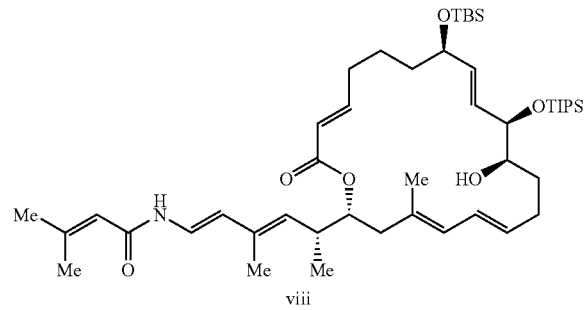

viii

A buffered HF-pyridine solution was made by mixing HF-pyridine (70%, 2.15 mL) and pyridine (10.75 mL) in THF (29 mL). 200 μL of this solution was added to a solution of compound 22 (15 mg, 0.017 mmol) in THF (3 mL) every 1.5 h until all of the starting material was consumed. The reaction mixture was diluted with EtOAc and washed with aq. NaHCO$_3$, aq. CuSO$_4$ and water. After drying and concentration of the organic phase, the residue was purified by FC [silica gel (washed with 0.5% Et$_3$N in hexanes), hexanes/EtOAc 6:1] to give compound viii (13 mg, 95%).

Method 25 vii →

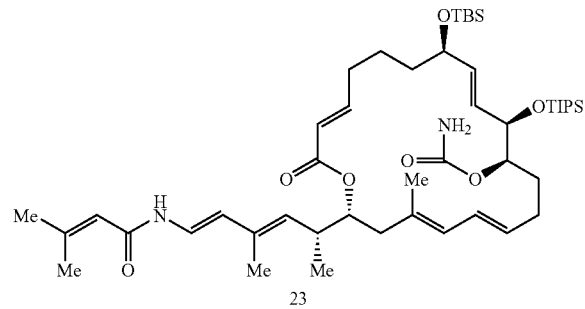

23

A solution of alcohol viii (13 mg, 0.016 mmol) in CH$_2$Cl$_2$ (2 mL) was treated with trichloroacetyl isocyanate (4.0 μL, 0.033 mmol) at 0° C. for 30 min. The reaction mixture was applied to a 1 inch pad of basic Al$_2$O$_3$, followed by rinsing with CH$_2$Cl$_2$ (1 mL). After 2 h, the column was eluted with EtOAc (20 mL). Concentration and purification by FC [silica gel (washed with 0.5% Et$_3$N in hexanes), hexanes/EtOAc 3:1] provided compound 23 (13 mg, 95%). [α]$_D$=−32.5 (EtOAc, c 0.28); $^1$H NMR (400 MHz, DMSO-d$^6$) δ 0.01 (s, 3H), 0.05 (s, 3H), 0.88 (s, 9H), 0.90 (d, 3H, J=6.8 Hz), 0.98-1.06 (m, 21H), 1.18 (m, 1H), 1.61 (s, 3H), 1.70 (s, 3H), 1.83 (s, 3H), 1.34-1.50 (m, 4H), 1.55 (m, 1H), 1.60 (m, 1H), 1.76 (m, 1H), 1.88-2.20 (m, 4H), 2.12 (s, 3H), 2.69 (m, 1H), 4.23 (dd, 1H, J=6.4, 6.4 Hz), 4.29 (dd, 1H, J=4.8, 9.2 Hz), 4.55 (ddd, 1H, J=2.4, 6.8, 9.6 Hz), 4.84 (ddd, 1H, J=1.6, 8.4, 10.0 Hz), 5.15 (d, 1H, J=9.6 Hz), 5.37 (ddd, 1H, J=4.8, 8.8, 14.4 Hz), 5.49 (dd, 1H, J=6.8, 15.6 Hz), 5.59 (d, 1H, J=10.8 Hz), 5.65 (dd, 1H, J=4.8, 15.6 Hz), 5.69 (bs, 1H), 5.76 (d, 1H, J=15.2 Hz), 5.84 (d, 1H, J=14.8 Hz), 6.09 (dd, 1H, J=10.8, 14.8 Hz), 6.39 (bs, 2H), 6.69 (ddd, 1H, J=6.4, 8.4, 15.2 Hz), 6.85 (dd, 1H, J=10.4, 14.8 Hz), 9.85 (d, 1H, J=10.4 Hz); $^{13}$CNMR (100 MHz, DMSO-d$^6$) δ −5.0, −4.7, 11.9, 12.7, 16.3, 17.2, 17.8, 18.0, 18.0, 19.6, 24.3, 25.7, 27.1, 28.7, 31.0, 32.3, 36.2, 36.7, 42.9, 71.1, 74.0, 74.5, 75.0, 116.4, 118.1, 120.9, 122.2, 126.5, 127.8, 128.0, 129.8, 131.4, 132.2, 132.6, 135.4, 148.9, 151.9, 156.5, 163.1, 166.3; IR: 3344, 2929, 1722, 1641, 1462, 1383, 1259, 1079; MS (ES) calc. for C$_{48}$H$_{82}$N$_2$O$_7$Si$_2$Na [MNa]$^+$ 877.6; found 877.4.

Method 26

23 →

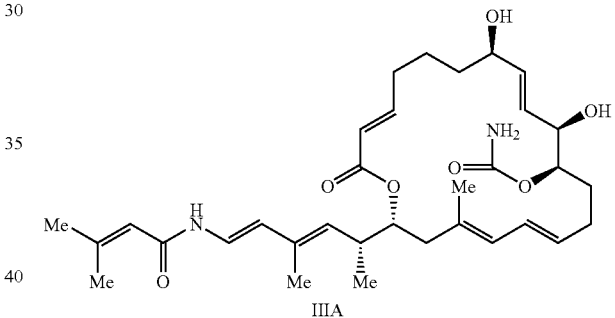

IIIA

TBAF (1.0 M in THF, 300 μL, 0.3 mmol) was added to a solution of compound 23 (12 mg, 0.014 mmol) in THF (4 mL) at 0° C. After 12 h, TBAF (1.0 M in THF, 300 μL, 0.3 mmol) was added again. After stirring for 24 h at 0° C., the mixture was diluted with EtOAc (20 mL) and washed with water. The organic phase was dried and concentrated to provide a residue that was purified by FC [silica gel (washed with 0.5% Et$_3$N in CH$_2$Cl$_2$), CH$_2$Cl$_2$/MeOH 20:1 to 10:1] to provide compound IIIA (3.4 mg, 41%). [α]$_D$=+40 (CH$_2$Cl$_2$, c 0.10); $^1$H NMR (400 MHz, DMSO-d$^6$) δ 0.90 (d, 3H, J=6.4 Hz), 1.18-1.27 (m, 3H), 1.29-1.40 (m, 4H), 1.90 (m, 1H), 1.99-2.19 (m, 4H), 1.62 (s, 3H), 1.83 (s, 3H), 2.12 (s, 3H), 2.69 (m, 1H), 1.70 (s, 3H), 3.89 (m, 1H), 4.04 (bs, 1H), 4.48 (ddd, 1H, J=2.4, 7.2, 9.6 Hz), 4.85 (ddd, 1H, J=1.3, 8.0, 10.4 Hz), 4.74 (d, 1H, J=3.6 Hz), 4.92 (d, 1H, J=3.6 Hz), 5.14 (d, 1H, J=10.0 Hz), 5.39 (ddd, 1H, J=5.2, 9.2, 14.8 Hz), 5.49 (dd, 1H, J=6.4, 15.6 Hz), 5.58 (dd, 1H, J=4.0, 15.6 Hz), 5.60 (d, 1H, J=9.6 Hz), 5.69 (bs, 1H), 5.76 (d, 1H, J=15.2 Hz), 5.85 (d, 1H, J=14.4 Hz), 6.10 (dd, 1H, J=10.8, 14.4 Hz), 6.49 (bs, 2H), 6.72 (ddd, 1H, J=6.4, 8.4, 15.2 Hz), 6.85 (dd, 1H, J=10.4, 14.8 Hz), 9.91 (d, 1H, J=10.4 Hz); $^{13}$C NMR (75 MHz, DMSO-d$^6$) δ 12.7, 16.2, 17.2, 19.6, 23.5, 27.0, 28.6, 31.5, 32.2, 36.7, 36.9, 42.9, 69.5, 73.2, 73.9, 75.4, 116.4, 118.1, 120.9, 122.2, 126.4, 127.9, 128.0, 129.8, 131.3, 132.3, 132.6, 135.7, 149.4, 151.8, 156.9, 163.2, 165.3; IR: 3367, 2921, 1712, 1640, 1447, 1387, 1266, 1194, 1026; MS (ES) calc. for $C_{33}H_{49}N_2O_7$ [MH]$^+$ 585.4; found, 585.3.

Method 27 ent-3 + 23 →

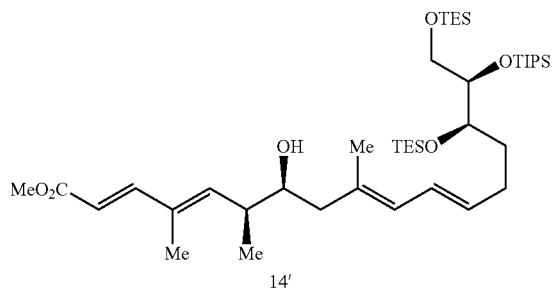

14'

Reaction of ent-3 (258 mg, 0.71 mmol) and 13 (465 mg, 0.71 mmol) according to the procedure described for compound 14 yielded compound 14' (440 mg, 81%) as colorless oil. $[\alpha]_D$=−28.2 (CHCl$_3$, c 0.39); $^1$H NMR (400 MHz, CDCl$_3$) δ 7.34 (1H, d, J=15.5), 6.24 (1H, dd, J=15.0, 10.8), 5.86 (1H, 10.1), 5.83 (1H, d, J=15.5), 5.78 (1H, d, J=10.1), 5.63 (1H, dt, J=15.0, 7.1), 3.85 (2H, br d, J=8.4), 3.76 (3H, s), 3.66 (1H, m), 3.56 (1H, m), 3.49 (1H, dd, J=10.3, 8.2), 2.62 (1H, m), 2.26 (2H, br d, J=13.9), 1.95-2.01 (2H, m), 1.82 (3H, s), 1.81 (3H, s), 1.22-1.36 (1H, m), 1.00-1.18 (3H, m), 1.10 (3H, d, J=6.8), 1.07 (18H, d, J=4.0), 1.00 (1H, m), 0.97 (9H, t, J=7.9), 0.94 (9H, t, J=7.9), 0.60 (6H, q, J=7.9), 0.58 (6H, q, J=8.0); $^{13}$C NMR (100 MHz, CDCl$_3$) δ 168.1, 149.9, 144.3, 134.2, 132.9, 132.3, 128.7, 126.4, 116.0, 77.4, 74.1, 72.5, 63.8, 51.6, 46.0, 39.5, 31.0, 30.3, 18.4, 16.6, 16.3, 12.8, 12.7, 7.1, 7.0, 5.3, 4.4; IR: 3489, 2954, 2876, 1723, 1624, 1169, 1131, 1015, 984, 741.

Method 28

14' + 2 →

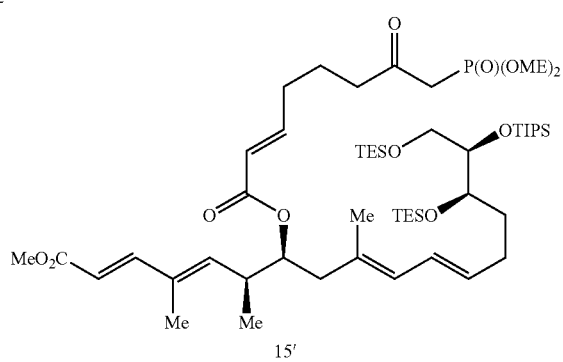

15'

Compound 15' was prepared according to the procedure described for the preparation of 15. Starting from compound 2 (280 mg, 1.06 mmol), and compound 14' (440 mg, 0.57 mmol) compound 15' (398 mg, 69%) was obtained as colorless oil after purification by FC (silica gel, Hexanes/EtOAc 2:1 to EtOAc). $[\alpha]_D$=−17.5 (CHCl$_3$, c 0.28); $^1$H NMR (400 MHz, CDCl$_3$) δ7.31 (1H, d, J=15.7), 6.89 (1H, dt, J=15.7, 6.8), 6.19 (1H, dd, J=15.0, 10.8), 5.83 (1H, d, J=15.5), 5.80 (1H, d, J=15.5), 5.74 (1H, d, J=10.6), 5.73 (1H, d, J=9.7), 5.53 (1H, dt, J=15.0, 7.0), 5.02 (1H, br. q, J=6.1), 3.81-3.86 (2H, m), 3.81 (3H, s), 3.78 (3H, s), 3.76 (3H, s), 3.63-3.68 (1H, m), 3.47 (1H, dd, J=10.2, 8.2), 3.09 (2H, d, 2J$_{PH}$=27), 2.77-2.86 (1H, m), 2.66 (2H, t, J=7.0), 2.19-2.34 (5H, m), 1.92-2.08 (1H, m), 1.70-1.83 (2H, m), 1.77 (3H, s), 1.74 (3H, s), 1.20-1.32 (1H, m), 1.02-1.16 (4H, m), 1.07 (18H, d, J=4.0), 1.03 (3H, d, J=6.8), 0.96 (9H, t, J=7.9), 0.94 (9H, t, J=7.9), 0.60 (6H, q, J=7.9), 0.58 (6H, q, J=8.0); $^{13}$C NMR (100 MHz, CDCl$_3$) δ 201.1, 167.9, 166.0, 149.6, 148.3, 142.8, 133.3, 133.2, 131.4, 128.2, 126.7, 121.9, 116.2, 77.3, 63.8, 53.1 (2C), 51.5, 43.1, 42.4, 42.1, 40.9, 36.7, 31.2, 30.9, 30.2, 21.6, 18.2, 16.7, 15.9, 12.7, 12.6, 7.0, 6.9, 5.2, 4.3; IR: 2954, 2876, 1720, 1653, 1624, 1460, 1265, 1170, 1132, 1100, 1017, 741; MS (MALDI) calc. for $C_{52}H_{97}O_{11}PSi_3Na$ [MNa]$^+$1035.6; found 1035.6.

Method 29

15' →

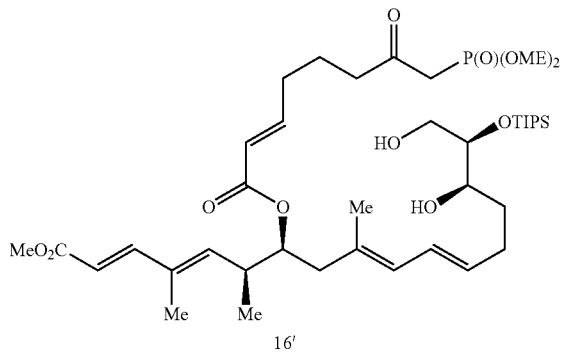

16'

Compound 16' was prepared according to the procedure described for the preparation of 16. Starting from compound 15' (391 mg, 0.39 mmol), compound 16' (287 mg, 95%) was obtained as colorless oil after purification by FC (silica gel, CH$_2$Cl$_2$/MeOH 50:1 to 20:1). $[\alpha]_D$=−40.4 (CHCl$_3$, c 0.48); $^1$HNMR (400 MHz, CDCl$_3$) δ 7.31 (1H, d, J=15.7), 6.88 (1H, dt, J=15.5, 6.9), 6.20 (1H, dd, J=15.0, 10.8), 5.83 (1H, d, J=15.7), 5.79 (1H, d, J=15.7), 5.74 (1H, d, J=7.9), 5.72 (1H, d, J=9.1), 5.56 (1H, dt, J=15.0, 7.0), 4.99-5.03 (1H, m), 3.60-3.81 (4H, m), 3.80 (3H, s), 3.78 (3H, s), 3.76 (3H, s), 3.09 (2H, d, 2J$_{PH}$=22.7), 2.77-2.86 (1H, m), 2.65 (2H, t, J=7.0), 2.46-2.56 (2H, m), 2.12-2.39 (6H, m), 1.92-2.08 (1H, m), 1.70-1.83 (2H, m), 1.78 (3H, s), 1.73 (3H, s), 1.50-1.68 (2H, m), 1.20-1.28 (2H, m), 1.04-1.16 (3H, m), 1.09 (18H, d, J=4.2), 1.02 (3H, d, J=6.6); $^{13}$C NMR (100 MHz, CDCl$_3$) δ201.3, 168.0, 166.1, 149.7, 148.4, 142.8, 133.3, 132.8, 131.9, 128.2, 127.1, 122.0, 116.4, 75.1, 74.9, 72.4, 64.3, 53.3, 53.2, 51.7, 43.3, 42.8, 42.4, 40.7, 37.2, 33.1, 31.3, 29.9, 29.6, 21.8, 18.3, 16.9, 16.3, 12.8; IR: 3421, 2944, 2866, 1717, 1652, 1624, 1313, 1262, 1172, 1035, 984; MS (ES) calc. for $C_{40}H_{69}O_{11}PSiNa$ [MNa]$^+$807.4; found 807.2.

Method 30

16' ⟶

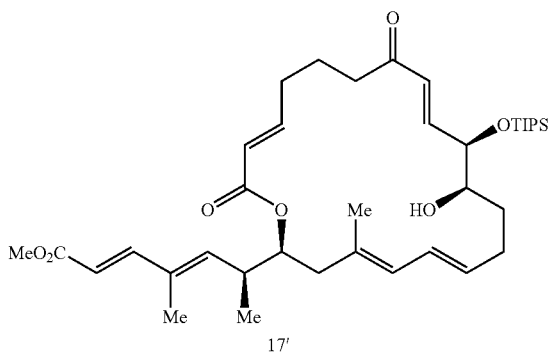

17'

Compound 17' was prepared according to the procedure described for the preparation of 17. Starting from compound 16' (287 mg, 0.37 mmol), compound 17' (139 mg, 58%) was obtained after purification by FC (silica gel, Hexanes/EtOAc 6:1 to 4:1). $[\alpha]_D=-8.3$ (CHCl$_3$, c 0.24); $^1$H NMR (400 MHz, CDCl$_3$) δ 7.32 (1H, d, J=15.7), 6.79-6.87 (1H, m), 6.59 (1H, dd, J=16.4, 6.8), 6.19 (1H, m), 6.15 (1H, d, J=16.4), 5.84 (1H, d, J=15.6), 5.77 (1H, d, J=16.0), 5.72 (1H, d, J=9.2), 5.69 (1H, d, J=10.0), 5.53-5.60 (1H, m), 5.07 (1H, br t, J=8.0), 4.16 (1H, t, J=7.2), 3.76 (3H, s), 3.58 (1H, m), 2.77-2.86 (1H, m), 2.54 (2H, d, J=7.6), 2.10-2.37 (6H, m), 1.65-1.84 (2H, m), 1.80 (3H, s), 1.70 (3H, s), 1.60 (3H, d, J=5.6), 1.36-1.44 (2H, m), 1.25-1.28 (2H, m), 1.04-1.12 (3H, m), 1.07 (18H, d, J=1.6), 1.02 (3H, d, J=6.8); $^{13}$C NMR (100 MHz, CDCl$_3$) δ 200.2, 167.9, 166.1, 149.5, 148.6, 145.8, 142.4, 133.5, 131.9, 131.7, 131.4, 128.0, 127.5, 121.9, 116.4, 76.7, 73.9, 73.3, 51.7, 43.4, 38.6, 38.0, 32.9, 31.3, 29.8, 28.5, 23.2, 18.1, 16.7, 16.4, 12.8, 12.4; IR: 3453, 2944, 2867, 1719, 1656, 1625, 1313, 1277, 1170.

Method 31

17' ⟶

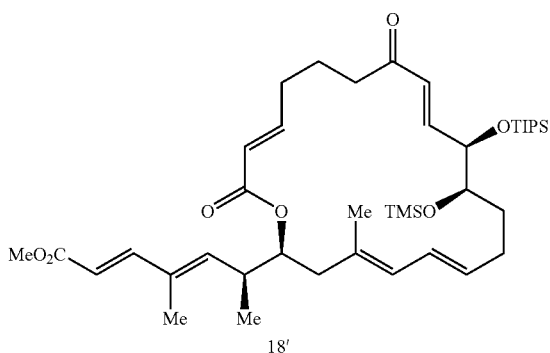

18'

Compound 18' was prepared according to the procedure described for the preparation of 18. Starting from compound 17' (139 mg, 0.21 mmol), compound 18' (130 mg, 85%) was obtained as a colorless oil after purification by FC (silica gel, Hexanes/EtOAc 10:1). $[\alpha]_D=+112.4$ (CHCl$_3$, c 0.29); $^1$H NMR (400 MHz, CDCl$_3$) δ 7.32 (1H, d, J=15.6), 6.79-6.87 (1H, m), 6.81 (1H, dd, J=16.0, 3.6), 6.30 (1H, dd, J=16.0, 1.6), 6.10 (1H, dd, J=14.8, 11.2), 5.84 (1H, d, J=16.0), 5.74 (1H, d, J=14.8), 5.71 (1H, d, J=10.4), 5.68 (1H, d, J=12.0), 5.47 (1H, ddd, J=14.4, 10.4, 4.0), 5.04 (1H, ddd, J=10.8, 8.4, 2.4), 4.41-4.44 (1H, m), 3.76 (3H, s), 3.69-3.73 (1H, m), 2.74-2.82 (1H, m), 2.60-2.68 (1H, m), 2.46-2.54 (1H, m), 2.05-2.29 (6H, m), 1.83-1.92 (1H, m), 1.80 (3H, s), 1.62-1.74 (1H, m), 1.69 (3H, s), 1.22-1.29 (2H, m), 1.00-1.15 (3H, m), 1.07 (18H, d, J=1.6), 1.02 (3H, d, J=6.8), 0.16 (9H, s); $^{13}$C NMR (100 MHz, CDCl$_3$) δ 201.3, 167.9, 166.4, 149.6, 149.0, 146.9, 142.5, 133.5, 133.1, 131.4, 129.9, 129.0, 126.6, 121.4, 116.4, 75.3, 74.8, 73.8, 51.7, 44.0, 40.1, 38.1, 33.1, 31.7, 30.1, 29.8, 24.8, 18.2, 16.8, 16.3, 12.8, 12.4, 0.57; IR: 2947, 2867, 1721, 1671, 1626, 1313, 1252, 1169, 1108, 1015, 985, 843.

Method 32

18' ⟶

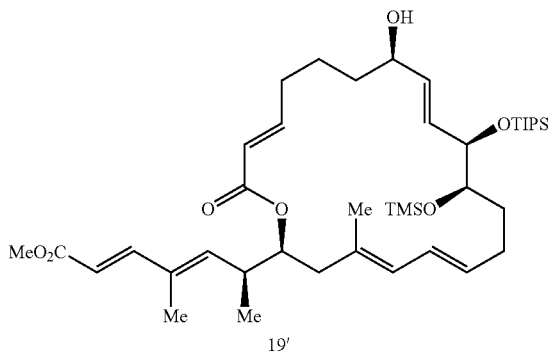

19'

Reduction of enone 18' (91 mg, 0.13 mmol) with (S)-(−)-2-Methyl-CBS-oxazaborolidine according to the procedure described for the reduction of enone 18 provided allylic alcohol 19' (21 mg, 23%) and its epimer (68 mg, 75%) in a ratio of 1:3 after purification by FC (silica gel, hexanes/EtOAc 8:1. This reduction was a mismatched case and reduction with NaBH$_4$ provided a 1:10 mixture favoring the undesired C7-epimer of 19'. 19': $[\alpha]_D=+98.5$ (CHCl$_3$, c 0.26); $^1$H NMR (400 MHz, CDCl$_3$) δ 0.15 (9H, s), 1.02 (3H, d, J=6.8), 1.08 (18H, d, J=3.3), 1.00-1.15 (3H, m), 1.22-1.29 (2H, m), 1.50-1.66 (3H, m), 1.71 (3H, s), 1.81 (3H, s), 1.76-1.89 (1H, m), 2.01-2.22 (6H, m), 2.73-2.80 (1H, m), 3.63 (1H, dd, J=8.9, 4.9), 3.76 (3H, s), 4.03-4.08 (1H, m), 4.33 (1H, m), 5.00 (1H, br. t, J=9.0), 5.46 (1H, ddd, J=15.0, 10.6, 4.2), 5.65 (1H, d, J=11.1), 5.67 (1H, d, J=9.3), 5.71 (1H, d, J=9.1), 5.75 (1H, d, J=15.2), 5.81 (1H, dd, J=15.2, 2.4), 5.85 (1H, d, J=12.1), 6.12 (1H, dd, J=15.5, 10.7), 6.84 (1H, ddd, J=15.3, 10.2, 4.8), 7.33 (1H, d, J=10.1); $^{13}$C NMR (100 MHz, CDCl$_3$) δ 0.7, 12.6, 12.9, 16.6, 16.9, 18.3, 25.6, 30.9, 32.0, 33.4, 37.5, 38.1, 44.2, 51.8, 73.8, 73.9, 74.6, 75.8, 116.4, 120.9, 126.7, 128.7, 131.5, 132.5, 133.1, 133.5, 142.8, 149.7 (2C), 166.4, 168.0; IR: 3499, 2945, 2866, 1721, 1656, 1624, 1313, 1252, 1170, 1105, 1016, 979, 842; MS (ES) calc. for C$_{41}$H$_{70}$O$_7$Si$_2$Na [MNa]$^+$ 753.5; found 753.3.

C7-epi-19': $^1$H NMR (400 MHz, CDCl$_3$) δ 0.15 (9H, s), 1.02 (3H, d, J=6.8), 1.08 (18H, d, J=3.3), 1.00-1.15 (3H, m), 1.22-1.29 (2H, m), 1.50-1.66 (3H, m), 1.71 (3H, s), 1.81 (3H, s), 1.76-1.89 (1H, m), 2.01-2.22 (6H, m), 2.73-2.80 (1H, m), 3.63 (1H, dd, J=8.9, 4.9), 3.76 (3H, s), 4.03-4.08 (1H, m), 4.33 (1H, m), 5.00 (1H, br. t, J=9.0), 5.46 (1H, ddd, J=15.0, 10.6, 4.2), 5.65 (1H, d, J=11.1), 5.67 (1H, d, J=9.3), 5.71 (1H, d, J=9.1), 5.75 (1H, d, J=15.2), 5.81 (1H, dd, J=15.2, 2.4), 5.85 (1H, d, J=12.1), 6.12 (1H, dd, J=15.5, 10.7), 6.84 (1H, ddd, J=15.3, 10.2, 4.8), 7.33 (1H, d, J=10.1); $^{13}$C NMR (100 MHz, CDCl$_3$) δ 0.7, 12.6, 12.9, 16.6, 16.9, 18.3, 25.6, 30.9, 32.0, 33.4, 37.5, 38.1, 44.2, 51.8, 73.8, 73.9, 74.6, 75.8, 116.4, 120.9, 126.7, 128.7, 131.5, 132.5, 133.1, 133.5, 142.8, 149.7 (2C), 166.4, 168.0; MS (ES) calc. for C$_{41}$H$_{70}$O$_7$Si$_2$Na [MNa]$^+$, 753.5; found 753.3.

(R)-MTPA ester of 19': $^1$H NMR (400 MHz, CDCl$_3$) δ 0.18 (9H, s), 1.02 (3H, d, J=6.8 Hz), 1.05 (21H, m), 1.17-1.43 (3H, m), 1.57-1.68 (2H, m), 1.72 (3H, s), 1.80 (3H, s), 1.86-1.96 (2H, m), 2.01-2.19 (4H, m), 2.78 (1H, m), 3.54 (3H, s), 3.63 (1H, dd, J=10.0, 4.3 Hz), 3.76 (3H, s), 4.37 (1H, ddd, J=1.6, 2.0, 4.4 Hz), 5.00 (1H, brt, J=9.6 Hz), 5.38-5.48 (2H, m), 5.64 (1H, d, J=11.2 Hz), 5.69-5.76 (3H, m), 5.84 (1H, d, J=15.6 Hz), 6.08 (1H, dd, J=2.8, 15.6 Hz), 6.11 (1H, ddd, J=10.8, 15.2 Hz), 6.81 (1H, ddd, J=4.4, 10.4, 14.8 Hz), 7.32 (1H, d, J=15.2 Hz), 7.39 (3H, m), 7.52 (2H, m).

(S)-MTPA ester of 19': $^1$HNMR (400 MHz, CDCl$_3$) δ 0.18 (9H, s), 1.02 (3H, d, J=6.8 Hz), 1.05 (21H, m), 1.17-1.43 (3H, m), 1.68-1.78 (2H, m), 1.72 (3H, s), 1.81 (3H, s), 1.86-1.96 (2H, m), 2.01-2.19 (4H, m), 2.78 (1H, m), 3.51 (3H, s), 3.63 (1H, dd, J=10.0, 4.3 Hz), 3.77 (3H, s), 4.34 (1H, ddd, J=1.6, 2.0, 4.4 Hz), 5.00 (1H, brt, J=8.4 Hz), 5.38-5.48 (2H, m), 5.64 (1H, d, J=11.2 Hz), 5.68-5.72 (2H, m), 5.76 (1H, d, J=15.6 Hz), 5.84 (1H, d, J=15.6), 6.05 (1H, dd, J=2.8, 15.6 Hz), 6.13 (1H, ddd, J=10.8, 15.2 Hz), 6.83 (1H, ddd, J=4.4, 10.4, 14.8 Hz), 7.33 (1H, d, J=15.6 Hz), 7.39 (3H, m), 7.52 (2H, m).

Method 33

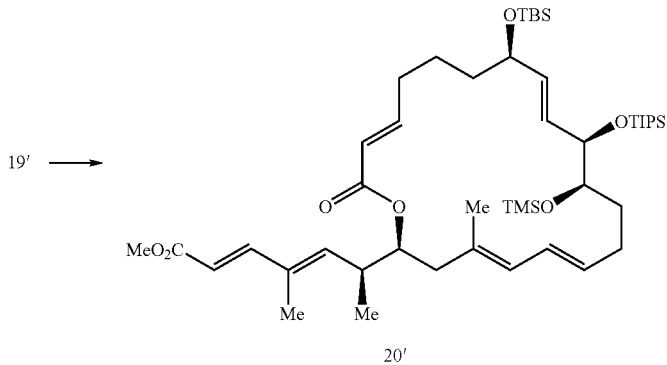

| | H-2 | H-3 | H-4 | H-5 | H-6a | H-6b | H-8 | H-9 | H-10 | H-11 |
|---|---|---|---|---|---|---|---|---|---|---|
| (R)-MTPA ester | 5.708 | 6.810 | 2.120 | 1.288~1.322 | 1.704 | 1.630 | 5.732 | 6.080 | 4.365 | 3.631 |
| (S)-MTPA ester | 5.709 | 6.829 | 2.130 | 1.320~1.360 | 1.752 | 1.694 | 5.701 | 6.050 | 4.338 | 3.630 |
| δ$_R$-δ$_S$ (ppm) | −0.001 | −0.019 | −0.010 | −0.032~−0.038 | −0.048 | −0.064 | +0.031 | +0.030 | +0.027 | +0.001 |

Silylation of allylic alcohol 19' (15.1 mg, 0.02 mmol) according to the procedure described for the preparation of 20 yielded silyl ether 20' (16.8 mg, 96%) after purification by FC (silica gel, hexanes/EtOAc 20:1). [α]$_D$=+66.5 (CHCl$_3$, c 0.34); $^1$H NMR (400 MHz, CDCl$_3$) δ 0.01 (3H, s), 0.05 (3H, s), 0.15 (9H, s), 0.87 (9H, s), 1.02 (3H, d, J=6.8), 1.08 (18H, d, J=3.3), 1.00-1.15 (3H, m), 1.22-1.29 (2H, m), 1.50-1.66 (3H, m), 1.71 (3H, s), 1.81 (3H, s), 1.85-1.94 (1H, m), 2.01-2.22 (6H, m), 2.73-2.80 (1H, m), 3.61 (1H, dd, J=9.2, 4.4), 3.76 (3H, s), 3.98-4.03 (1H, m), 4.30 (1H, br. d, J=4.4), 4.99 (1H, t, J=9.6), 5.46 (1H, ddd, J=14.8, 10.6, 4.2), 5.61-5.64 (2H, m), 5.68 (1H, d, J=15.6), 5.71 (1H, d, J=12.0), 5.75 (1H, d, J=16.8), 5.84 (1H, d, J=12.1), 6.11 (1H, dd, J=14.8, 11.2), 6.83 (1H, ddd, J=15.3, 10.2, 4.8), 7.33 (1H, d, J=15.9); $^{13}$C NMR (100 MHz, CDCl$_3$) δ −4.6, −4.2, 0.71, 12.6, 12.9, 16.6, 16.9, 18.3, 18.4, 25.3, 26.0, 31.0, 32.0, 33.5, 36.8, 38.1, 44.2, 51.8, 73.8, 74.0, 75.2, 75.9, 116.4, 120.9, 126.6, 128.6, 129.5, 131.4, 133.2, 133.5, 142.8, 149.7, 150.0, 166.5, 168.0; IR: 2948, 2865, 1723, 1657, 1625, 1312, 1252, 1168, 1104, 1061, 839.

Method 34

20' →

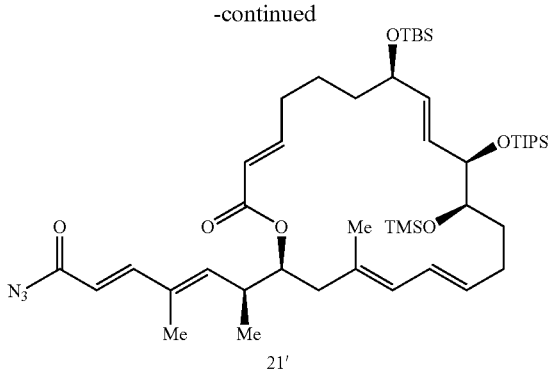

21'

(Bu₃Sn)₂O (101 μL, 0.20 mmol) was added to a solution of compound 20' (16.8 mg, 20 μmol) in toluene (0.5 mL). After the mixture was heated at 80° C. for 48 hours, it was directly filtered through a short pad of silica gel. After evaporation of the solvent, a colorless oil was obtained which was used directly for the next step. To a solution of this crude carboxylic acid in benzene (3 mL) was added Et₃N (50 μL, 0.36 mmol) and (PhO)₂P(O)N₃ (18 μL, 80 μmol) at rt. After stirring for 5 hours, the mixture was directly purified by FC (silica gel, hexanes/EtOAc 20:1) to give azide 21' (8 mg, 50% for 2 steps).

Method 35

21' ⟶

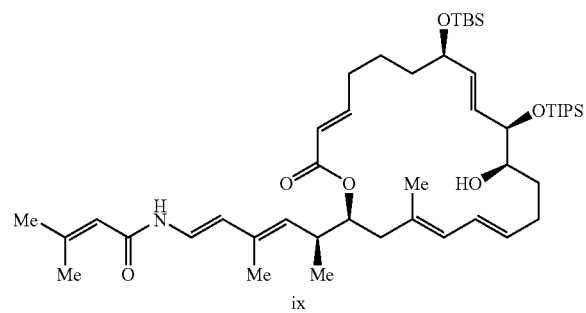

ix

A solution of azide 21' (8 mg, 9 μmol) in benzene (2 mL) was refluxed for 5 h and the solvent was removed via a steady stream of N₂. The residue was dissolved in THF (1 mL) and added dropwise to a solution of 2-methyl-1-propenylmagnesium bromide (0.5 M in THF, 300 μL, 0.15 mmol) in THF (1 mL) at −78° C. over 20 min. After stirring for 30 min, ether (cooled to −78° C., 15 mL) was added followed by aq. NH₄Cl (2 mL). The mixture was extracted with EtOAc and the combined extracts were dried and concentrated. The residue was dissolved in dry THF (2 mL) and treated with buffered HF-pyridine [0.2 mL of a solution prepared by mixing HF-pyridine (70%, 2.15 mL) and pyridine (10.75 mL) in THF (29 mL)]. After 3 h, the reaction mixture was diluted with EtOAc (20 mL) and washed with aq. NaHCO₃, aq. CuSO₄ and water. The organic phase was dried and concentrated. The residue was purified by FC [silica gel (washed with 0.5% Et₃N in hexanes), hexanes/EtOAc 6:1] to give compound ix (4 mg, 50% for three steps from 21'). ¹H NMR (400 MHz, C₆D₆) δ 0.04 (3H, s), 0.07 (3H, s), 0.972 (9H, s), 1.06 (3H, d, J=6.8), 1.07-1.12 (21H, m), 1.20-1.40 (6H, m), 1.44 (3H, s), 1.55 (3H, s), 1.76 (3H, s), 1.80-1.88 (2H, m), 2.10-2.31 (4H, m), 2.19 (3H, s), 2.67 (1H, m), 3.55 (1H, br. t, J=6.8), 3.92 (1H, m), 4.24 (1H, br. d, J=6.4), 4.92 (1H, br. s), 5.17 (1H, d, J=10.0), 5.29 (1H, ddd, J=10.1, 8.8, 4.8), 5.46 (1H, d, J=14.4), 5.61 (1H, m), 5.70 (1H, br. s), 5.82 (1H, d, J=14.8), 5.89 (1H, d, J=10.8), 6.12 (1H, br. d, J=10.8), 6.32 (1H, dd, J=15.2, 10.8), 6.96 (1H, ddd, J=15.2, 8.8, 6.0), 7.35 (1H, dd, J=14.8, 11.2).

Method 36 ix ⟶ 23' R' = TBS; R'' = TIPS vii ⟶ Formula IIIB; R' =

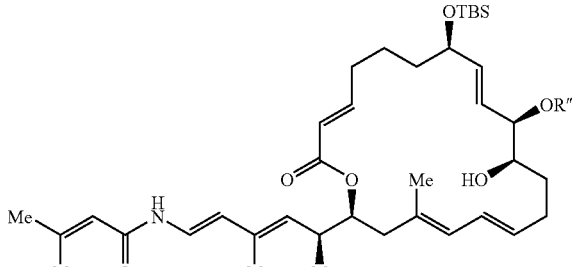

R'' = H

A solution of alcohol ix (4 mg, 4.9 μmol) in CH₂Cl₂ (1 mL) was treated with trichloroacetyl isocyanate (1.3 μL, 10 μmol) at 0° C. for 15 min. The reaction mixture was applied to a 1 inch pad of basic Al₂O₃, followed by rinsing with CH₂Cl₂ (1 mL). After 2 h, the material was eluted with EtOAc (20 mL). Concentration and purification by FC [silica gel (rinced with 0.5% Et₃N in hexanes), hex/EtOAc 3:1] provided compound 23'(1.5 mg, 38%). TBAF (1.0 M in THF, 30 μL, 30 μmol) was added to the solution of compound 23' (1.3 mg, 1.5 μmol) in THF (0.8 mL) at 0° C. After 48 hours, EtOAc (20 mL) was added. It was washed with water, dried and concentrated. The crude was purified by FC [silica gel (washed with 0.5% Et₃N in CH₂Cl₂), CH₂Cl₂/MeOH 20:1 to 5:1] to provide palmerolide A (24) (0.5 mg, 56%), together with 0.1 mg of recovered 23'.

IIIB: ¹H NMR (400 MHz, DMSO-d₆) δ 0.87 (3H, d, J=6.5), 0.95 (1H, m), 1.02 (1H, m), 1.25 (2H, m), 1.47 (1H, m), 1.56 (1H, m), 1.58 (3H, s), 1.68 (3H, s), 1.80 (3H, s), 2.09 (3H, s), 1.94 (2H, m), 1.89-2.18 (6H, m), 2.66 (1H, m), 3.79 (1H, m), 4.11 (1H, br. s), 4.45 (1H, dd, J=10.5, 4.8), 4.67 (1H, d, J=4.0), 4.81 (1H, br. t, J=8.4), 5.11 (1H, d, J=9.6), 5.16 (1H, d, J=4.8), 5.39 (1H, m), 5.44 (1H, d, J=15.6), 5.51 (1H, dd, J=15.6, 7.6), 5.57 (1H, d, J=10.4), 5.66 (1H, br s), 5.74 (1H, d, J=15.2), 5.81 (1H, d, J=14.4), 6.02 (1H, dd, J=12.6, 11.2), 6.46 (2H, br), 6.69 (1H, ddd, J=15.2, 10.0, 4.8), 6.82 (1H, dd, J=14.4, 10.8), 9.83 (1H, d, J=10.0). MS (MALDI) calc. for C₃₃H₄₈N₂O₇Na [MNa]⁺607.3; found 607.5.

We claim:

1. A compound of Formula VIII, a tautomer of the compound of Formula VIII, a pharmaceutically acceptable salt of the compound of Formula VIII; or a pharmaceutically acceptable salt of the tautomer of the compound of Formula VIII:

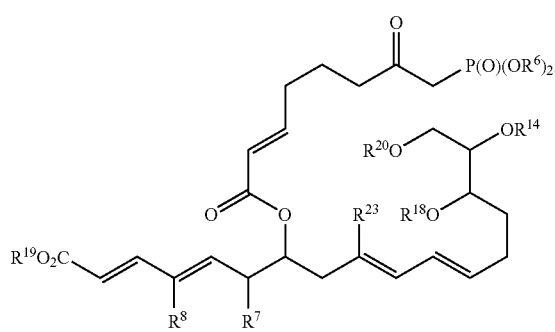

(VIII)

wherein $R^7$ and $R^8$ are independently H, F, substituted or unsubstituted $C_{1-3}$ alkyl;

$R^6$ and $R^{19}$ are independently H or a substituted or unsubstituted $C_{1-4}$ alkyl; and $R^{14}$, $R^{18}$, and $R^{20}$ are independently H or a protecting group.

2. The compound according to claim 1, wherein: $R^{14}$, $R^{18}$, and $R^{20}$ are each independently H, trimethylsilyl, triethylsilyl, tripropylsilyl, triisopropylsilyl, tributylsilyl, tert-butyldimethylsilyl, or tert-butyldiphenylsilyl; $R^{19}$ is methyl or ethyl; and $R^6$ is methyl or ethyl.

* * * * *